(12) United States Patent
DiPerna

(10) Patent No.: US 8,448,824 B2
(45) Date of Patent: May 28, 2013

(54) SLIDEABLE FLOW METERING DEVICES AND RELATED METHODS

(75) Inventor: Paul M. DiPerna, San Clemente, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 973 days.

(21) Appl. No.: 12/393,973

(22) Filed: Feb. 26, 2009

(65) Prior Publication Data
US 2010/0065579 A1 Mar. 18, 2010

Related U.S. Application Data

(60) Provisional application No. 61/097,492, filed on Sep. 16, 2008.

(51) Int. Cl.
B65D 37/00 (2006.01)

(52) U.S. Cl.
USPC ............... 222/207; 222/1; 222/55; 222/63; 222/214; 222/447

(58) Field of Classification Search
USPC ............ 222/1, 52, 55, 12, 630–632, 386.5, 222/63, 504, 450, 447, 453, 207; 604/141, 604/152–153, 500, 151
See application file for complete search history.

(56) References Cited

U.S. PATENT DOCUMENTS

| | | |
|---|---|---|
| 318,856 A | 5/1885 | Bilz |
| 329,881 A | 11/1885 | Benton |
| 332,402 A | 12/1885 | Leadley |
| 596,062 A | 12/1897 | Firey |
| 818,938 A | 4/1906 | Crane |
| 926,092 A | 6/1909 | Bright |
| 1,304,036 A | 5/1919 | Eshelby |
| 1,643,021 A | 9/1927 | Luyties |
| 1,657,663 A | 6/1928 | Devereux |
| 1,910,032 A | 5/1933 | Mills |
| 2,018,316 A | 10/1935 | Ownings |
| 2,029,630 A | 2/1936 | McMichael |
| 2,147,164 A | 2/1939 | Kent |
| 2,412,397 A * | 12/1946 | Harper ..................... 417/474 |
| 2,444,677 A | 7/1948 | Rosenblum |

(Continued)

FOREIGN PATENT DOCUMENTS

| | | |
|---|---|---|
| CN | 1229347 A | 9/1999 |
| CN | 2668155 Y | 1/2005 |

(Continued)

OTHER PUBLICATIONS

U.S. Appl. No. 60/789,243, filed Apr. 5, 2006, Beavis.

(Continued)

Primary Examiner — Frederick C. Nicolas
(74) Attorney, Agent, or Firm — Patterson Thuente Pedersen, P.A.

(57) ABSTRACT

A novel enhanced flow metering device is disclosed, as well as related methods, that safely controls and meters the flow of a flow material. A pump fills a flow metering device with a flow material, which then dispenses the flow material to a target. The flow material charges the device by moving into at least one chamber when an actuation shaft is in a charging position. Flow materials are dispensed from the chambers of the flow metering device when the actuation shaft is moved into at least one dispensing positions.

18 Claims, 15 Drawing Sheets

U.S. PATENT DOCUMENTS

| | | | |
|---|---|---|---|
| 2,454,929 A | 11/1948 | Kempton | |
| 2,495,693 A | 1/1950 | Byrd, Jr. et al. | |
| 2,497,020 A | 2/1950 | Singer | |
| 2,568,519 A | 9/1951 | Smith | |
| 2,599,325 A | 6/1952 | Fritzberg | |
| 2,629,402 A | 2/1953 | Cook | |
| 2,667,900 A | 2/1954 | Cantalupo | |
| 2,674,262 A | 4/1954 | Bradshaw | |
| 2,679,954 A | 6/1954 | Barnes | |
| 2,701,583 A | 2/1955 | Rux | |
| 2,706,612 A | 4/1955 | Ratelband | |
| 2,728,355 A | 12/1955 | Dahl | |
| 2,735,642 A | 2/1956 | Norman | |
| 2,746,709 A | 5/1956 | Minor | |
| 2,764,183 A | 9/1956 | Gollehon | |
| 2,781,058 A | 2/1957 | Warhus | |
| 2,834,379 A | 5/1958 | Fields | |
| 2,841,237 A | 7/1958 | Slayter | |
| 2,852,033 A | 9/1958 | Orser | |
| 2,878,836 A | 3/1959 | Binks | |
| 2,891,578 A | 6/1959 | Dahl et al. | |
| 2,898,078 A | 8/1959 | Stephenson et al. | |
| 2,898,088 A | 8/1959 | Alder | |
| 2,899,979 A | 8/1959 | Dahl et al. | |
| 2,936,788 A | 5/1960 | Dahl et al. | |
| 2,939,487 A | 6/1960 | Fraser et al. | |
| 2,960,109 A | 11/1960 | Wilson | |
| 2,968,318 A | 1/1961 | Bauman | |
| 2,989,086 A | 6/1961 | Dahl | |
| 3,017,903 A | 1/1962 | Steffens | |
| 3,035,613 A | 5/1962 | Beatty | |
| 3,060,966 A | 10/1962 | Ratelband | |
| 3,061,039 A | 10/1962 | Peters | |
| 3,070,132 A | 12/1962 | Sheridan | |
| 3,072,151 A | 1/1963 | Quercia | |
| 3,095,120 A | 6/1963 | Steiner et al. | |
| 3,095,175 A | 6/1963 | Iketani | |
| 3,118,646 A | 1/1964 | Markey | |
| 3,077,903 A | 2/1964 | Honsinger | |
| 3,121,445 A | 2/1964 | Wisniewski | |
| 3,123,900 A | 3/1964 | Millar | |
| 3,143,861 A | 8/1964 | Dumas | |
| 3,174,694 A | 3/1965 | Kitabayshi | |
| 3,189,125 A | 6/1965 | Windsor et al. | |
| 3,195,586 A | 7/1965 | Vogt | |
| 3,203,662 A | 8/1965 | Lau | |
| 3,214,903 A | 11/1965 | Cochran | |
| 3,216,451 A | 11/1965 | Smallpeice | |
| 3,298,394 A | 1/1967 | Chorkey | |
| 3,338,049 A | 8/1967 | Fernberger | |
| 3,376,625 A | 4/1968 | McCulloch | |
| 3,409,050 A | 11/1968 | Weese | |
| 3,428,223 A | 2/1969 | Lewiecki et al. | |
| 3,430,659 A | 3/1969 | Henderson | |
| 3,479,002 A | 11/1969 | Hirs | |
| 3,493,496 A | 2/1970 | Bray et al. | |
| 3,508,587 A | 4/1970 | Mauch | |
| 3,532,125 A | 10/1970 | Everett et al. | |
| 3,556,159 A | 1/1971 | Bleasdale | |
| 3,568,847 A | 3/1971 | Carr | |
| 3,586,040 A | 6/1971 | Urback | |
| 3,620,500 A | 11/1971 | Santomieri | |
| 3,621,882 A | 11/1971 | Kuplec | |
| 3,665,967 A | 5/1972 | Kachnik | |
| 3,674,183 A | 7/1972 | Venable et al. | |
| 3,675,672 A | 7/1972 | Freeman | |
| 3,693,484 A | 9/1972 | Sanderson, Jr. | |
| 3,696,958 A | 10/1972 | Lee | |
| 3,699,812 A | 10/1972 | Masnik | |
| 3,717,174 A | 2/1973 | Dewall | |
| 3,756,459 A | 9/1973 | Bannister et al. | |
| 3,833,019 A | 9/1974 | Diggs | |
| 3,836,113 A | 9/1974 | Johnson | |
| 3,837,363 A | 9/1974 | Meronek | |
| 3,847,178 A | 11/1974 | Keppel | |
| 3,860,353 A | 1/1975 | Lukasik et al. | |
| 3,894,538 A | 7/1975 | Richter | |
| 3,899,135 A | 8/1975 | O'Brian | |
| 3,918,674 A | 11/1975 | Sutter | |
| 3,946,761 A | 3/1976 | Thompson et al. | |
| RE28,890 E | 7/1976 | Ingram et al. | |
| 3,970,105 A | 7/1976 | Pelton et al. | |
| 3,991,972 A | 11/1976 | Eaton | |
| 4,000,857 A | 1/1977 | Moen | |
| 4,003,398 A | 1/1977 | Duveau | |
| 4,023,772 A | 5/1977 | Ratelband | |
| 4,032,265 A | 6/1977 | Miller | |
| 4,042,153 A * | 8/1977 | Callahan et al. | 222/207 |
| 4,076,872 A | 2/1978 | Lewicki et al. | |
| 4,087,301 A | 5/1978 | Steadman | |
| 4,103,689 A | 8/1978 | Leighton | |
| 4,105,050 A | 8/1978 | Hendrickson et al. | |
| 4,106,510 A | 8/1978 | Hakim et al. | |
| 4,111,391 A | 9/1978 | Pilolla | |
| 4,156,127 A | 5/1979 | Sako et al. | |
| 4,178,938 A | 12/1979 | Au | |
| 4,191,184 A | 3/1980 | Carlisle | |
| 4,191,204 A | 3/1980 | Nehring | |
| 4,191,358 A | 3/1980 | Ferri | |
| 4,193,552 A | 3/1980 | Ishikawa | |
| 4,195,810 A | 4/1980 | Lavin | |
| 4,215,726 A | 8/1980 | Tagami | |
| 4,228,956 A | 10/1980 | Varner | |
| 4,248,270 A | 2/1981 | Ostrowski | |
| 4,250,872 A | 2/1981 | Tamari | |
| 4,254,791 A | 3/1981 | Bron | |
| 4,265,241 A | 5/1981 | Portner et al. | |
| 4,275,727 A | 6/1981 | Keeri-Szanto | |
| 4,314,621 A | 2/1982 | Hansen | |
| 4,330,071 A * | 5/1982 | Ohlson | 222/207 |
| 4,344,459 A | 8/1982 | Nelson | |
| 4,356,935 A | 11/1982 | Kamin | |
| 4,367,786 A | 1/1983 | Hafner et al. | |
| 4,382,453 A | 5/1983 | Bujan et al. | |
| 4,406,656 A | 9/1983 | Hattler et al. | |
| 4,432,468 A | 2/1984 | Siff et al. | |
| 4,440,154 A | 4/1984 | Bellows | |
| 4,440,323 A * | 4/1984 | Benson | 222/209 |
| 4,443,218 A | 4/1984 | DeCant, Jr. et al. | |
| 4,448,538 A | 5/1984 | Mantel | |
| 4,457,343 A | 7/1984 | Zukausky | |
| 4,469,481 A | 9/1984 | Kobayashi | |
| 4,492,339 A | 1/1985 | Kreitzberg | |
| 4,498,843 A | 2/1985 | Schneider et al. | |
| 4,508,144 A | 4/1985 | Bernett | |
| 4,515,536 A | 5/1985 | van Os | |
| 4,520,948 A * | 6/1985 | Hampel et al. | 222/103 |
| 4,527,595 A | 7/1985 | Jorgensen et al. | |
| 4,529,106 A * | 7/1985 | Broadfoot et al. | 222/207 |
| 4,529,401 A | 7/1985 | Leslie et al. | |
| 4,557,726 A | 12/1985 | Reinicke | |
| 4,559,036 A | 12/1985 | Wunsch | |
| 4,562,960 A | 1/1986 | Marty et al. | |
| 4,570,745 A | 2/1986 | Sparks et al. | |
| 4,592,390 A | 6/1986 | Boyd | |
| 4,609,014 A | 9/1986 | Jurevic et al. | |
| 4,620,648 A | 11/1986 | Schwartzman | |
| 4,624,661 A | 11/1986 | Arimond | |
| 4,627,573 A | 12/1986 | Havens et al. | |
| 4,628,928 A | 12/1986 | Lowell | |
| 4,636,226 A | 1/1987 | Canfora | |
| 4,646,945 A | 3/1987 | Steiner et al. | |
| 4,649,959 A | 3/1987 | Wadleigh | |
| 4,650,471 A | 3/1987 | Tamari | |
| 4,651,781 A | 3/1987 | Kandelman | |
| 4,657,486 A | 4/1987 | Stempfle et al. | |
| 4,666,430 A | 5/1987 | Brown et al. | |
| 4,667,700 A | 5/1987 | Buzzi | |
| 4,673,415 A | 6/1987 | Stanford | |
| 4,684,364 A | 8/1987 | Sawyer et al. | |
| 4,684,367 A | 8/1987 | Schaffer et al. | |
| 4,687,423 A | 8/1987 | Maget | |
| 4,713,063 A | 12/1987 | Krumme | |
| 4,718,893 A | 1/1988 | Dorman et al. | |
| 4,724,870 A | 2/1988 | Molb k et al. | |
| 4,770,211 A | 9/1988 | Olsson | |
| 4,773,448 A | 9/1988 | Francis | |

| | | | | | | |
|---|---|---|---|---|---|---|
| 4,776,842 A | 10/1988 | Franetzki et al. | | 5,207,666 A | 5/1993 | Idriss et al. |
| 4,778,451 A | 10/1988 | Kamen | | 5,209,265 A | 5/1993 | Taguri et al. |
| 4,787,408 A | 11/1988 | Twerdochlib | | 5,215,450 A | 6/1993 | Tamari |
| 4,823,844 A | 4/1989 | Bartholomew | | 5,217,440 A | 6/1993 | Frassica |
| 4,826,482 A | 5/1989 | Kamen | | 5,218,987 A | 6/1993 | Heil |
| 4,840,191 A | 6/1989 | Gausman et al. | | 5,220,515 A | 6/1993 | Freerks et al. |
| 4,869,431 A | 9/1989 | Jubert et al. | | 5,224,796 A | 7/1993 | Zeman |
| 4,871,093 A | 10/1989 | Burshtain et al. | | 5,226,446 A | 7/1993 | Cooper |
| 4,883,093 A | 11/1989 | Miles et al. | | 5,228,291 A | 7/1993 | Meyering |
| 4,886,514 A | 12/1989 | Maget | | 5,228,842 A | 7/1993 | Guebeli et al. |
| 4,893,966 A * | 1/1990 | Roehl ............................ 406/127 | | 5,232,437 A | 8/1993 | Lysaght et al. |
| 4,897,906 A | 2/1990 | Bartholomew | | 5,232,449 A | 8/1993 | Stern et al. |
| 4,902,278 A | 2/1990 | Maget | | 5,240,603 A | 8/1993 | Frank et al. |
| 4,931,050 A | 6/1990 | Idriss | | 5,241,935 A | 9/1993 | Beck et al. |
| 4,938,259 A | 7/1990 | Schmidt | | 5,242,406 A | 9/1993 | Gross et al. |
| 4,955,860 A | 9/1990 | Ruano | | 5,242,408 A | 9/1993 | Jhuboo et al. |
| 4,969,884 A | 11/1990 | Yum | | 5,243,983 A | 9/1993 | Tarr et al. |
| 4,973,402 A | 11/1990 | Johnson et al. | | 5,246,147 A | 9/1993 | Gross |
| 4,976,162 A | 12/1990 | Kamen | | 5,254,096 A | 10/1993 | Rondelet et al. |
| 4,985,015 A | 1/1991 | Oberman et al. | | 5,257,971 A | 11/1993 | Lord et al. |
| 4,986,312 A | 1/1991 | Gute | | 5,259,399 A | 11/1993 | Brown |
| 4,989,456 A | 2/1991 | Stupecky | | 5,259,732 A | 11/1993 | Stern |
| 4,995,258 A | 2/1991 | Frank | | 5,261,459 A | 11/1993 | Atkinson et al. |
| 5,000,739 A | 3/1991 | Kulisz et al. | | 5,261,884 A | 11/1993 | Stern et al. |
| 5,002,527 A | 3/1991 | Reller et al. | | 5,266,265 A | 11/1993 | Raible |
| 5,006,997 A | 4/1991 | Reich | | 5,270,005 A | 12/1993 | Raible |
| 5,011,477 A | 4/1991 | Winchell et al. | | 5,271,724 A | 12/1993 | vanLintel |
| 5,027,861 A | 7/1991 | Gute | | 5,272,294 A | 12/1993 | Charboneau et al. |
| 5,035,865 A | 7/1991 | Inaba et al. | | 5,272,909 A | 12/1993 | Nguyen et al. |
| 5,038,821 A | 8/1991 | Maget | | 5,273,406 A | 12/1993 | Feygin |
| 5,044,900 A | 9/1991 | Cavallaro | | 5,273,518 A | 12/1993 | Lee et al. |
| 5,047,044 A | 9/1991 | Smith et al. | | 5,278,142 A | 1/1994 | Chiou |
| 5,049,141 A | 9/1991 | Olive | | 5,279,543 A | 1/1994 | Glickfeld et al. |
| 5,050,612 A | 9/1991 | Matsumura | | 5,279,586 A | 1/1994 | Balkwell |
| 5,053,001 A | 10/1991 | Reller et al. | | 5,290,684 A | 3/1994 | Kelly |
| 5,053,189 A | 10/1991 | Chrise et al. | | 5,295,966 A | 3/1994 | Stern et al. |
| 5,059,182 A | 10/1991 | Laing | | 5,295,967 A | 3/1994 | Rondelet et al. |
| 5,062,834 A | 11/1991 | Gross et al. | | 5,303,843 A | 4/1994 | Zink et al. |
| 5,062,841 A | 11/1991 | Siegel | | 5,304,126 A | 4/1994 | Epstein et al. |
| 5,076,911 A | 12/1991 | Brown et al. | | 5,304,163 A | 4/1994 | Bonnici et al. |
| 5,078,683 A | 1/1992 | Sancoff et al. | | 5,312,233 A | 5/1994 | Tanny et al. |
| 5,082,240 A | 1/1992 | Richmond | | 5,320,250 A | 6/1994 | La et al. |
| 5,082,503 A | 1/1992 | Sluga et al. | | 5,321,392 A | 6/1994 | Skakoon et al. |
| 5,083,908 A | 1/1992 | Gagnebin et al. | | 5,322,418 A | 6/1994 | Comer |
| 5,084,021 A | 1/1992 | Baldwin | | 5,322,620 A | 6/1994 | Brown et al. |
| 5,085,644 A | 2/1992 | Watson et al. | | 5,322,626 A | 6/1994 | Frank et al. |
| 5,087,245 A | 2/1992 | Doan | | 5,327,777 A | 7/1994 | Kaye et al. |
| 5,090,963 A | 2/1992 | Gross et al. | | 5,334,162 A | 8/1994 | Harris |
| 5,091,091 A | 2/1992 | Terman | | 5,335,852 A | 8/1994 | Muntean et al. |
| 5,091,094 A | 2/1992 | Veech | | 5,336,051 A | 8/1994 | Tamari |
| 5,103,211 A | 4/1992 | Daoud et al. | | 5,338,157 A | 8/1994 | Blomquist |
| 5,104,526 A | 4/1992 | Brown et al. | | 5,339,865 A | 8/1994 | Asghar et al. |
| 5,108,363 A | 4/1992 | Tuttle et al. | | 5,341,783 A | 8/1994 | Beck et al. |
| 5,125,781 A | 6/1992 | Breunig et al. | | 5,345,488 A | 9/1994 | Skipper et al. |
| 5,126,324 A | 6/1992 | Clark et al. | | 5,348,197 A | 9/1994 | Mizzi et al. |
| 5,127,258 A | 7/1992 | Brown et al. | | 5,349,933 A | 9/1994 | Hasegawa et al. |
| 5,128,145 A | 7/1992 | Edgren et al. | | 5,350,224 A | 9/1994 | Nell et al. |
| 5,135,491 A | 8/1992 | Baldwin | | 5,352,201 A | 10/1994 | Jemmott |
| 5,135,498 A | 8/1992 | Kam et al. | | 5,354,273 A | 10/1994 | Hagen |
| 5,135,499 A | 8/1992 | Tafani et al. | | 5,356,375 A | 10/1994 | Higley et al. |
| 5,149,413 A | 9/1992 | Maget | | 5,356,378 A | 10/1994 | Doan |
| 5,154,712 A | 10/1992 | Herwick et al. | | 5,356,632 A | 10/1994 | Gross et al. |
| 5,156,591 A | 10/1992 | Gross et al. | | 5,358,635 A | 10/1994 | Frank et al. |
| 5,156,598 A | 10/1992 | Skakoon et al. | | 5,360,062 A | 11/1994 | White |
| 5,157,960 A | 10/1992 | Brehm et al. | | 5,360,734 A | 11/1994 | Chapman et al. |
| 5,158,230 A | 10/1992 | Curran | | 5,362,307 A | 11/1994 | Guy et al. |
| 5,173,302 A | 12/1992 | Holmblad et al. | | 5,366,904 A | 11/1994 | Qureshi et al. |
| 5,176,502 A | 1/1993 | Sanderson et al. | | 5,367,910 A | 11/1994 | Woodward |
| 5,178,603 A | 1/1993 | Prince | | 5,368,555 A | 11/1994 | Sussman et al. |
| 5,182,258 A | 1/1993 | Chiou | | 5,369,976 A | 12/1994 | Ratton |
| 5,184,359 A | 2/1993 | Tsukamura et al. | | 5,370,622 A | 12/1994 | Livingston et al. |
| 5,186,431 A | 2/1993 | Tamari | | 5,370,870 A | 12/1994 | Wong |
| 5,186,805 A | 2/1993 | Gross et al. | | 5,373,865 A | 12/1994 | Jung et al. |
| 5,190,522 A | 3/1993 | Wojcicki et al. | | 5,381,823 A | 1/1995 | DiBartolo |
| 5,191,719 A | 3/1993 | Kitt | | 5,384,709 A | 1/1995 | Seder et al. |
| 5,192,264 A | 3/1993 | Fossel | | 5,387,327 A | 2/1995 | Khan |
| 5,203,506 A | 4/1993 | Gross et al. | | 5,388,453 A | 2/1995 | Ratton et al. |
| 5,207,642 A | 5/1993 | Orkin et al. | | 5,389,078 A | 2/1995 | Zalesky et al. |
| 5,207,645 A | 5/1993 | Ross et al. | | 5,389,091 A | 2/1995 | Moorehead |

| | | | | | | |
|---|---|---|---|---|---|---|
| 5,395,324 | A | 3/1995 | Hinrichs | 5,566,865 | A | 10/1996 | Jouillat et al. |
| 5,399,166 | A | 3/1995 | Laing | 5,567,287 | A | 10/1996 | Joshi et al. |
| 5,403,551 | A | 4/1995 | Galloway et al. | 5,568,038 | A | 10/1996 | Tatsumi |
| 5,407,444 | A | 4/1995 | Kroll | 5,568,884 | A | 10/1996 | Bruna |
| 5,410,908 | A | 5/1995 | Erichsen | 5,575,310 | A | 11/1996 | Kamen et al. |
| 5,411,685 | A | 5/1995 | Burgis | 5,575,632 | A | 11/1996 | Morris et al. |
| 5,415,024 | A | 5/1995 | Proffitt et al. | 5,575,770 | A | 11/1996 | Melsky et al. |
| 5,418,154 | A | 5/1995 | Aebischer et al. | 5,578,005 | A | 11/1996 | Sancoff et al. |
| 5,421,208 | A | 6/1995 | Packard et al. | 5,578,832 | A | 11/1996 | Trulson et al. |
| 5,423,743 | A | 6/1995 | Buttrefield | 5,582,168 | A | 12/1996 | Samuels et al. |
| 5,425,374 | A | 6/1995 | Ueda et al. | 5,590,648 | A | 1/1997 | Mitchell et al. |
| 5,425,706 | A | 6/1995 | Gross et al. | 5,593,552 | A | 1/1997 | Joshi et al. |
| 5,425,742 | A | 6/1995 | Joy | 5,602,040 | A | 2/1997 | May et al. |
| 5,427,870 | A | 6/1995 | Joshi et al. | 5,603,729 | A | 2/1997 | Brown et al. |
| 5,429,483 | A | 7/1995 | Tamari | 5,605,701 | A | 2/1997 | Bymaster et al. |
| 5,429,601 | A | 7/1995 | Conley et al. | 5,607,418 | A | 3/1997 | Arzbaecher |
| 5,431,171 | A | 7/1995 | Harrison et al. | 5,615,671 | A | 4/1997 | Schoonen et al. |
| 5,433,710 | A | 7/1995 | VanAntwerp et al. | 5,616,123 | A | 4/1997 | Cheikh |
| 5,435,465 | A | 7/1995 | El-Amin | 5,616,132 | A | 4/1997 | Newman |
| 5,435,697 | A | 7/1995 | Guebeli et al. | 5,617,650 | A | 4/1997 | Grim |
| 5,435,797 | A | 7/1995 | Harris | RE35,501 | E | 5/1997 | Ross et al. |
| 5,438,510 | A | 8/1995 | Bryant et al. | 5,628,349 | A | 5/1997 | Diggins et al. |
| 5,441,027 | A | 8/1995 | Buchanon et al. | 5,628,624 | A | 5/1997 | Nelson, II |
| 5,442,948 | A | 8/1995 | Cowing | 5,634,491 | A | 6/1997 | Benedict |
| 5,442,950 | A | 8/1995 | Unalmiser et al. | 5,634,779 | A | 6/1997 | Eysymontt |
| 5,443,450 | A | 8/1995 | Kratoska | 5,637,092 | A | 6/1997 | Shaw |
| 5,445,616 | A | 8/1995 | Kratoska et al. | 5,637,095 | A | 6/1997 | Nason et al. |
| 5,447,509 | A | 9/1995 | Mills et al. | 5,639,220 | A | 6/1997 | Hayakawa |
| 5,447,863 | A | 9/1995 | Langley | 5,639,441 | A | 6/1997 | Sievers et al. |
| 5,448,034 | A | 9/1995 | Skipper et al. | 5,639,473 | A | 6/1997 | Grinstaff et al. |
| 5,448,978 | A | 9/1995 | Hasegawa et al. | 5,641,405 | A | 6/1997 | Keshaviah et al. |
| 5,450,750 | A | 9/1995 | Abler | 5,643,773 | A | 7/1997 | Aebischer et al. |
| 5,454,922 | A | 10/1995 | Joshi et al. | 5,645,526 | A | 7/1997 | Flower |
| 5,458,469 | A | 10/1995 | Hauser | 5,651,980 | A | 7/1997 | Lanza et al. |
| 5,460,030 | A | 10/1995 | Blosxom et al. | 5,656,032 | A | 8/1997 | Kriesel et al. |
| 5,460,605 | A | 10/1995 | tuttle et al. | 5,656,501 | A | 8/1997 | Yedgar et al. |
| 5,460,945 | A | 10/1995 | Springer et al. | 5,656,503 | A | 8/1997 | May et al. |
| 5,462,525 | A | 10/1995 | Srisathapat et al. | 5,658,250 | A | 8/1997 | Blomquist |
| 5,462,535 | A | 10/1995 | Bonnichsen et al. | 5,659,126 | A | 8/1997 | Farber |
| 5,464,392 | A | 11/1995 | Epstein et al. | 5,660,150 | A | 8/1997 | Andersen et al. |
| 5,464,398 | A | 11/1995 | Haindl | 5,665,065 | A | 9/1997 | Colman et al. |
| 5,466,218 | A | 11/1995 | Srisathapat et al. | 5,665,070 | A | 9/1997 | McPhee |
| 5,466,229 | A | 11/1995 | Elson et al. | 5,669,877 | A | 9/1997 | Blomquist |
| 5,469,846 | A | 11/1995 | Khan | 5,671,874 | A | 9/1997 | Behar et al. |
| 5,470,318 | A | 11/1995 | Griffith, III et al. | 5,676,651 | A | 10/1997 | Larson, Jr. et al. |
| 5,472,577 | A | 12/1995 | Porter et al. | 5,681,435 | A | 10/1997 | Joshi et al. |
| 5,476,444 | A | 12/1995 | Keeling et al. | 5,688,113 | A | 11/1997 | Bareiss et al. |
| 5,476,449 | A | 12/1995 | Richmond | 5,688,225 | A | 11/1997 | Walker |
| 5,478,751 | A | 12/1995 | Oosta et al. | 5,688,232 | A | 11/1997 | Flower |
| 5,480,381 | A | 1/1996 | Weston | 5,693,018 | A | 12/1997 | Kriesel et al. |
| 5,482,745 | A | 1/1996 | Cuellar et al. | 5,694,961 | A | 12/1997 | Begemann et al. |
| 5,483,930 | A | 1/1996 | Moriya et al. | 5,695,464 | A | 12/1997 | Viallet |
| 5,485,408 | A | 1/1996 | Blomquist | 5,702,384 | A | 12/1997 | Umeyama et al. |
| 5,487,528 | A | 1/1996 | Richmond | 5,704,520 | A * | 1/1998 | Gross .......................... 222/334 |
| 5,489,265 | A | 2/1996 | Montalvo et al. | 5,707,212 | A | 1/1998 | Matthews |
| 5,492,534 | A | 2/1996 | Athayde et al. | 5,707,361 | A | 1/1998 | Slettenmark |
| 5,494,578 | A | 2/1996 | Brown et al. | 5,711,989 | A | 1/1998 | Ciardella et al. |
| 5,498,421 | A | 3/1996 | Grinstaff et al. | 5,712,795 | A | 1/1998 | Layman et al. |
| 5,503,538 | A | 4/1996 | Wiernicki et al. | 5,713,856 | A | 2/1998 | Eggers et al. |
| 5,505,709 | A | 4/1996 | Funderburk et al. | 5,713,858 | A | 2/1998 | Heruth et al. |
| 5,505,777 | A | 4/1996 | Ciardella et al. | 5,718,562 | A | 2/1998 | Lawless et al. |
| 5,509,294 | A | 4/1996 | Gowing | 5,719,761 | A | 2/1998 | Gatti et al. |
| 5,510,336 | A | 4/1996 | Saven et al. | 5,720,241 | A | 2/1998 | Gail |
| 5,518,730 | A | 5/1996 | Fuisz | 5,720,921 | A | 2/1998 | Mesrol |
| 5,526,675 | A | 6/1996 | Ratton | 5,722,367 | A | 3/1998 | Izadorek |
| 5,527,288 | A | 6/1996 | Gross et al. | 5,728,396 | A | 3/1998 | Peery et al. |
| 5,527,307 | A | 6/1996 | Srisathapat et al. | 5,730,149 | A | 3/1998 | Nakayama et al. |
| 5,527,704 | A | 6/1996 | Wolf, Jr. et al. | 5,730,723 | A | 3/1998 | Castellano et al. |
| 5,533,876 | A | 7/1996 | Nelson, II | 5,735,818 | A | 4/1998 | Kriesel et al. |
| 5,538,043 | A | 7/1996 | Salazar | 5,738,650 | A | 4/1998 | Gregg |
| 5,540,562 | A | 7/1996 | Giter | 5,740,718 | A | 4/1998 | Rathweg |
| 5,544,519 | A | 8/1996 | Hammarberg et al. | 5,741,211 | A | 4/1998 | Renirie |
| 5,545,252 | A | 8/1996 | Hinshaw et al. | 5,741,242 | A | 4/1998 | Kriesel et al. |
| 5,551,391 | A | 9/1996 | Beck et al. | 5,743,291 | A | 4/1998 | Nehm et al. |
| 5,554,177 | A | 9/1996 | Kieval et al. | 5,755,683 | A | 5/1998 | Houle et al. |
| 5,556,421 | A | 9/1996 | Prutchi et al. | 5,759,018 | A | 6/1998 | Thanscheidt |
| 5,558,638 | A | 9/1996 | Evers et al. | 5,763,267 | A | 6/1998 | Kurjan et al. |
| 5,562,079 | A | 10/1996 | Gray, Jr. | 5,763,398 | A | 6/1998 | Bengtsson |
| 5,563,347 | A | 10/1996 | Martin et al. | 5,765,464 | A | 6/1998 | Morita |

| | | | | | | |
|---|---|---|---|---|---|---|
| 5,765,729 A | 6/1998 | Miller et al. | | 5,919,209 A | 7/1999 | Schouten |
| 5,769,615 A | 6/1998 | Giter | | 5,919,216 A | 7/1999 | Houben et al. |
| 5,770,149 A | 6/1998 | Raible | | 5,924,456 A | 7/1999 | Simon |
| 5,770,160 A | 6/1998 | Smith et al. | | 5,925,629 A | 7/1999 | Place |
| 5,771,770 A | 6/1998 | Muller | | 5,928,194 A | 7/1999 | Maget |
| 5,782,931 A | 7/1998 | Yang et al. | | 5,928,281 A | 7/1999 | Huynh et al. |
| 5,785,688 A * | 7/1998 | Joshi et al. ............... 604/141 | | 5,931,814 A | 8/1999 | Alex et al. |
| 5,788,671 A | 8/1998 | Johnson | | 5,933,287 A | 8/1999 | Muller |
| 5,788,682 A | 8/1998 | Maget | | 5,935,099 A | 8/1999 | Peeterson et al. |
| 5,792,603 A | 8/1998 | Dunkelman et al. | | 5,935,168 A | 8/1999 | Yang et al. |
| 5,794,505 A | 8/1998 | Fischer et al. | | 5,935,598 A | 8/1999 | Sage et al. |
| 5,794,515 A | 8/1998 | Bethke | | 5,938,636 A | 8/1999 | Kramer et al. |
| 5,797,867 A | 8/1998 | Guerrera et al. | | 5,938,640 A | 8/1999 | Maget |
| 5,800,387 A | 9/1998 | Duffy et al. | | 5,941,846 A | 8/1999 | Duffy et al. |
| 5,800,420 A | 9/1998 | Gross et al. | | 5,950,879 A | 9/1999 | Ritsche |
| 5,803,319 A | 9/1998 | Smith et al. | | 5,951,523 A | 9/1999 | Osterlund et al. |
| 5,803,917 A | 9/1998 | Butterfield et al. | | 5,954,697 A | 9/1999 | Srisathapat et al. |
| 5,807,315 A | 9/1998 | Van Antwerp et al. | | 5,954,752 A | 9/1999 | Mongeon et al. |
| 5,807,375 A | 9/1998 | Gross et al. | | 5,957,861 A | 9/1999 | Combs et al. |
| 5,810,737 A | 9/1998 | Dardik | | 5,957,885 A | 9/1999 | Bollish et al. |
| 5,810,771 A | 9/1998 | Blomquist | | 5,957,889 A | 9/1999 | Poulson et al. |
| 5,814,020 A | 9/1998 | Gross | | 5,957,895 A | 9/1999 | Sage et al. |
| 5,814,100 A | 9/1998 | Carpentier et al. | | 5,958,760 A | 9/1999 | Freeman |
| 5,820,587 A | 10/1998 | Place | | 5,961,305 A * | 10/1999 | Eek et al. ............... 417/566 |
| 5,820,589 A | 10/1998 | Torgerson et al. | | 5,961,483 A | 10/1999 | Sage et al. |
| 5,820,622 A | 10/1998 | Gross et al. | | 5,962,566 A | 10/1999 | Grandfilis et al. |
| 5,823,388 A | 10/1998 | Green | | 5,964,724 A | 10/1999 | Rivera et al. |
| 5,823,746 A | 10/1998 | Johnson | | 5,973,012 A | 10/1999 | Behrmann et al. |
| 5,826,621 A | 10/1998 | Jemmott | | 5,980,596 A | 11/1999 | Hershkowitz et al. |
| 5,830,175 A | 11/1998 | Flower | | 5,983,976 A | 11/1999 | Kono |
| 5,837,220 A | 11/1998 | Blake et al. | | 5,984,894 A | 11/1999 | Poulsen et al. |
| 5,837,444 A | 11/1998 | Shah | | 5,984,897 A | 11/1999 | Peterson et al. |
| 5,840,071 A | 11/1998 | Kriesel et al. | | 5,984,906 A | 11/1999 | Bonnichsen et al. |
| 5,840,770 A | 11/1998 | Hill | | 5,985,305 A | 11/1999 | Peery et al. |
| 5,848,880 A | 12/1998 | Helmig | | 5,988,165 A | 11/1999 | Richey et al. |
| 5,848,990 A | 12/1998 | Cirelli et al. | | 5,988,998 A | 11/1999 | Glover |
| 5,848,991 A | 12/1998 | Gross et al. | | 5,989,238 A | 11/1999 | Ginsburg |
| 5,849,031 A | 12/1998 | Martinez et al. | | 5,992,695 A | 11/1999 | Start |
| 5,849,737 A | 12/1998 | Chaplan et al. | | 5,997,501 A | 12/1999 | Gross et al. |
| 5,851,198 A | 12/1998 | Castellano et al. | | 5,997,518 A | 12/1999 | Laibovitz et al. |
| 5,851,549 A | 12/1998 | Svec | | 6,001,585 A | 12/1999 | Gramer |
| 5,851,985 A | 12/1998 | Tepic et al. | | 6,003,736 A | 12/1999 | Ljunggren |
| 5,854,074 A | 12/1998 | Charlton et al. | | 6,006,800 A | 12/1999 | Nakano |
| 5,858,001 A | 1/1999 | Tsals et al. | | 6,007,314 A | 12/1999 | Nelson, II |
| 5,858,201 A | 1/1999 | Atsuka et al. | | 6,012,492 A | 1/2000 | Kozyuk |
| 5,858,388 A | 1/1999 | Grossman et al. | | 6,013,020 A | 1/2000 | Meloul et al. |
| 5,858,393 A | 1/1999 | Bymaster et al. | | 6,016,044 A | 1/2000 | Holdaway |
| 5,859,365 A | 1/1999 | Kataoka et al. | | 6,017,318 A | 1/2000 | Gauthier |
| 5,860,957 A | 1/1999 | Jacobson et al. | | 6,017,545 A | 1/2000 | Modi |
| 5,863,187 A | 1/1999 | Bensley et al. | | 6,023,641 A | 2/2000 | Thompson |
| 5,865,603 A | 2/1999 | Francart, Jr. | | 6,024,009 A | 2/2000 | Morita |
| 5,871,125 A | 2/1999 | Gross | | 6,024,539 A | 2/2000 | Blomquist |
| 5,871,515 A | 2/1999 | Wiklund et al. | | 6,030,358 A | 2/2000 | Odland |
| 5,873,857 A | 2/1999 | Kriesel | | 6,033,377 A | 3/2000 | Rasmussen et al. |
| 5,876,189 A | 3/1999 | Lukas et al. | | 6,034,054 A | 3/2000 | DeFelippis et al. |
| 5,876,368 A | 3/1999 | Flower | | 6,035,639 A | 3/2000 | Kolmanovsky |
| 5,876,370 A | 3/1999 | Blomquist | | 6,037,346 A | 3/2000 | Doherty, Jr. et al. |
| 5,877,146 A | 3/1999 | McKenzie et al. | | 6,038,960 A | 3/2000 | Fukushima et al. |
| 5,877,216 A | 3/1999 | Place et al. | | 6,042,561 A | 3/2000 | Ash et al. |
| 5,878,992 A | 3/1999 | Edwards et al. | | 6,048,337 A | 4/2000 | Svedman |
| 5,880,101 A | 3/1999 | Stankov | | 6,051,256 A | 4/2000 | Platz et al. |
| 5,882,494 A | 3/1999 | Van Antwerp et al. | | 6,056,522 A | 5/2000 | Johnson |
| 5,883,138 A | 3/1999 | Hershkowitz et al. | | 6,059,507 A | 5/2000 | Adams |
| 5,885,211 A | 3/1999 | Eppstein et al. | | 6,059,753 A | 5/2000 | Faust et al. |
| 5,885,250 A | 3/1999 | Kriesel et al. | | 6,062,022 A | 5/2000 | Folsom et al. |
| 5,885,614 A | 3/1999 | Hirsch | | 6,062,531 A | 5/2000 | Rapp et al. |
| 5,886,056 A | 3/1999 | Hershkowitz et al. | | 6,063,053 A | 5/2000 | Castellano et al. |
| 5,887,793 A | 3/1999 | Kieffer | | 6,065,279 A | 5/2000 | Kuromitsu et al. |
| 5,890,413 A | 4/1999 | Bayer et al. | | 6,065,289 A | 5/2000 | Phillips |
| 5,891,097 A | 4/1999 | Saito et al. | | 6,065,941 A | 5/2000 | Gray et al. |
| 5,893,708 A | 4/1999 | Nelson, II | | 6,071,423 A | 6/2000 | Brown et al. |
| 5,894,992 A | 4/1999 | Liu et al. | | 6,073,048 A | 6/2000 | Kieval et al. |
| 5,895,369 A | 4/1999 | Flower | | 6,074,359 A | 6/2000 | Keshaviah et al. |
| 5,897,530 A | 4/1999 | Jackson | | 6,077,246 A | 6/2000 | Kullas et al. |
| 5,902,336 A | 5/1999 | Mishkin | | 6,080,130 A | 6/2000 | Castellano et al. |
| 5,903,710 A | 5/1999 | Wefler et al. | | 6,083,602 A | 7/2000 | Caldwell et al. |
| 5,912,005 A | 6/1999 | Lanza et al. | | 6,083,710 A | 7/2000 | Heller et al. |
| 5,916,191 A | 6/1999 | Plunkett et al. | | 6,086,562 A | 7/2000 | Jacobson et al. |
| 5,919,156 A | 7/1999 | Stropkay et al. | | 6,093,167 A | 7/2000 | Houben et al. |

| | | | | | | |
|---|---|---|---|---|---|---|
| 6,093,312 | A | 7/2000 | Boulter | 6,254,355 B1 | 7/2001 | Gharib |
| 6,095,134 | A | 8/2000 | Sievers et al. | 6,256,533 B1 | 7/2001 | Yuzhakov et al. |
| 6,096,216 | A | 8/2000 | Shanbrom et al. | 6,257,178 B1 | 7/2001 | Laimbock |
| 6,099,293 | A | 8/2000 | Kern et al. | 6,257,191 B1 | 7/2001 | Kutlucinar |
| 6,099,495 | A | 8/2000 | Kinghorn et al. | 6,261,272 B1 | 7/2001 | Gross et al. |
| 6,099,504 | A | 8/2000 | Gross et al. | 6,261,280 B1 | 7/2001 | Houben et al. |
| 6,102,127 | A | 8/2000 | Pierce | 6,264,439 B1 | 7/2001 | Falk et al. |
| 6,103,033 | A | 8/2000 | Say et al. | 6,264,680 B1 | 7/2001 | Ash et al. |
| 6,103,275 | A | 8/2000 | Seitz et al. | 6,266,564 B1 | 7/2001 | Hill et al. |
| 6,106,477 | A | 8/2000 | Miesel et al. | 6,270,478 B1 | 8/2001 | Mernoe |
| 6,109,896 | A | 8/2000 | Schuller et al. | 6,275,717 B1 | 8/2001 | Gross et al. |
| 6,110,148 | A | 8/2000 | Brown et al. | 6,276,434 B1 | 8/2001 | Kono |
| 6,110,152 | A | 8/2000 | Kovelman | 6,277,819 B1 | 8/2001 | Efendic |
| 6,110,427 | A | 8/2000 | Uffenheimer | 6,280,408 B1 | 8/2001 | Sipin |
| RE36,871 | E | 9/2000 | Epstein et al. | 6,280,416 B1 | 8/2001 | Van Antwerp et al. |
| 6,113,782 | A | 9/2000 | Leonard | 6,283,197 B1 | 9/2001 | Kono |
| 6,120,460 | A | 9/2000 | Abreu | 6,283,680 B1 * | 9/2001 | Vidal ............................ 406/128 |
| 6,122,536 | A | 9/2000 | Sun et al. | 6,283,944 B1 | 9/2001 | McMullen et al. |
| 6,123,175 | A | 9/2000 | Fett | 6,283,949 B1 | 9/2001 | Roorda |
| 6,123,686 | A | 9/2000 | Olsen et al. | 6,284,725 B1 | 9/2001 | Coolidge et al. |
| 6,126,956 | A | 10/2000 | Grossman et al. | 6,288,518 B1 | 9/2001 | Yang et al. |
| 6,127,363 | A | 10/2000 | Doherty, Jr. et al. | 6,293,242 B1 | 9/2001 | Kutlucinar |
| 6,132,686 | A | 10/2000 | Gallup et al. | 6,294,550 B1 | 9/2001 | Place et al. |
| 6,135,196 | A | 10/2000 | Kono | 6,296,456 B1 | 10/2001 | Thornelow et al. |
| 6,135,978 | A | 10/2000 | Houben et al. | 6,298,760 B1 | 10/2001 | Danby |
| 6,142,939 | A | 11/2000 | Eppstein et al. | 6,298,941 B1 | 10/2001 | Spadafora |
| 6,143,238 | A | 11/2000 | Konishi et al. | 6,299,415 B1 | 10/2001 | Bahrton |
| 6,143,252 | A | 11/2000 | Haxo, Jr. et al. | 6,302,107 B1 | 10/2001 | Richey et al. |
| 6,144,866 | A | 11/2000 | Miesel et al. | 6,302,653 B1 | 10/2001 | Bryant et al. |
| 6,145,625 | A | 11/2000 | Prokop et al. | 6,302,855 B1 | 10/2001 | Lav et al. |
| 6,147,070 | A | 11/2000 | Facchini | 6,306,420 B1 | 10/2001 | Cheikh |
| 6,147,109 | A | 11/2000 | Liao et al. | 6,306,841 B1 | 10/2001 | Place et al. |
| 6,152,898 | A | 11/2000 | Olsen | 6,310,270 B1 | 10/2001 | Huang et al. |
| 6,155,748 | A | 12/2000 | Allen et al. | 6,312,409 B1 | 11/2001 | Gross |
| 6,156,753 | A | 12/2000 | Doherty, Jr. et al. | 6,314,317 B1 | 11/2001 | Willis |
| 6,158,431 | A | 12/2000 | Poole | 6,315,769 B1 | 11/2001 | Peer et al. |
| 6,158,965 | A | 12/2000 | Butterfield et al. | 6,319,245 B1 | 11/2001 | Berrigan |
| 6,163,721 | A | 12/2000 | Thompson | 6,323,022 B1 | 11/2001 | Chang et al. |
| 6,164,924 | A | 12/2000 | Gruett et al. | 6,325,999 B1 | 12/2001 | Bellgrau et al. |
| 6,165,155 | A | 12/2000 | Jacobson et al. | 6,327,964 B1 | 12/2001 | Schuller et al. |
| 6,167,290 | A | 12/2000 | Yang et al. | 6,328,004 B1 | 12/2001 | Rynhart |
| 6,168,575 | B1 | 1/2001 | Soltanpour | 6,331,172 B1 | 12/2001 | Epstein et al. |
| 6,175,752 | B1 | 1/2001 | Say et al. | 6,334,761 B1 | 1/2002 | Tai et al. |
| 6,176,692 | B1 | 1/2001 | Reinartz et al. | 6,338,942 B2 | 1/2002 | Kraus et al. |
| 6,178,996 | B1 | 1/2001 | Suzuki | 6,340,783 B1 | 1/2002 | Snow |
| 6,179,583 | B1 | 1/2001 | Weston | 6,342,037 B1 | 1/2002 | Roe et al. |
| 6,180,597 | B1 | 1/2001 | Liao et al. | 6,342,484 B1 | 1/2002 | Kulkarni et al. |
| 6,185,460 | B1 | 2/2001 | Thompson | 6,344,457 B1 | 2/2002 | Jeanpetit et al. |
| 6,186,982 | B1 | 2/2001 | Gross et al. | 6,346,095 B1 | 2/2002 | Gross et al. |
| 6,198,383 | B1 | 3/2001 | Sekura et al. | 6,350,589 B1 | 2/2002 | Morris et al. |
| 6,205,961 | B1 | 3/2001 | Bailey et al. | 6,355,030 B1 | 3/2002 | Aldrich et al. |
| 6,210,135 | B1 | 4/2001 | Rassin et al. | 6,358,519 B1 | 3/2002 | Waterman |
| 6,210,361 | B1 | 4/2001 | Kamen et al. | 6,364,865 B1 | 4/2002 | Lavi et al. |
| 6,210,957 | B1 | 4/2001 | Carpentier et al. | 6,365,185 B1 | 4/2002 | Ritchel et al. |
| 6,211,147 | B1 | 4/2001 | Unemori | 6,365,628 B1 | 4/2002 | Berge |
| 6,211,426 | B1 | 4/2001 | Abrams | 6,366,808 B1 | 4/2002 | Schroppel et al. |
| 6,212,948 | B1 | 4/2001 | Ekdahl et al. | 6,368,272 B1 | 4/2002 | Porumbescu |
| 6,217,826 | B1 | 4/2001 | Reeder et al. | 6,371,732 B1 | 4/2002 | Moubayed et al. |
| 6,218,666 | B1 | 4/2001 | Lukica et al. | 6,372,182 B1 | 4/2002 | Mauro et al. |
| 6,221,378 | B1 | 4/2001 | Modi | 6,372,508 B1 | 4/2002 | Shnizer et al. |
| 6,223,080 | B1 | 4/2001 | Thompson | 6,374,683 B1 | 4/2002 | Hunicke-Smith et al. |
| 6,223,703 | B1 | 5/2001 | Galvin | 6,381,493 B1 | 4/2002 | Stadler et al. |
| 6,224,347 | B1 | 5/2001 | Clark et al. | 6,382,923 B1 | 5/2002 | Gray |
| 6,224,352 | B1 | 5/2001 | Hauser et al. | 6,393,893 B1 | 5/2002 | Fetz et al. |
| 6,227,818 | B1 | 5/2001 | Falk et al. | 6,395,292 B2 | 5/2002 | Peery et al. |
| 6,228,044 | B1 | 5/2001 | Jensen et al. | 6,395,536 B2 | 5/2002 | Freeman |
| 6,229,584 | B1 | 5/2001 | Chuo et al. | 6,397,199 B1 | 5/2002 | Goodwin, III |
| 6,231,882 | B1 | 5/2001 | Modi | 6,398,718 B1 | 6/2002 | Yachia et al. |
| 6,236,887 | B1 | 5/2001 | Ben-Haim et al. | 6,398,760 B1 | 6/2002 | Danby |
| 6,238,423 | B1 | 5/2001 | Bardy | 6,399,024 B1 | 6/2002 | Bevirt et al. |
| 6,241,704 | B1 | 6/2001 | Peterson et al. | 6,402,689 B1 | 6/2002 | Scarantino et al. |
| 6,241,743 | B1 | 6/2001 | Levin et al. | 6,406,455 B1 | 6/2002 | Willis et al. |
| 6,245,347 | B1 | 6/2001 | Zhang et al. | 6,409,698 B1 | 6/2002 | Robinson |
| 6,247,493 | B1 | 6/2001 | Henderson | 6,412,273 B1 | 7/2002 | Rohs |
| 6,248,067 | B1 | 6/2001 | Causey, III et al. | 6,413,238 B1 | 7/2002 | Maget et al. |
| 6,248,093 | B1 | 6/2001 | Moberg | 6,413,254 B1 | 7/2002 | Hissong et al. |
| 6,248,280 | B1 | 6/2001 | Kern et al. | 6,415,961 B2 | 7/2002 | Bonningue |
| 6,251,293 | B1 * | 6/2001 | Snodgrass et al. ............ 210/767 | 6,416,215 B1 | 7/2002 | Terentiev |
| 6,251,932 | B1 | 6/2001 | Reicht et al. | 6,416,291 B1 | 7/2002 | Butterfield et al. |

| Patent No. | Date | Inventor(s) | Patent No. | Date | Inventor(s) |
|---|---|---|---|---|---|
| 6,416,293 B1 | 7/2002 | Bouchard et al. | 6,540,996 B1 | 4/2003 | Zwaal et al. |
| 6,420,169 B1 | 7/2002 | Read et al. | 6,541,021 B1 | 4/2003 | Johnson et al. |
| 6,422,256 B1 | 7/2002 | Balazy et al. | 6,542,774 B2 | 4/2003 | Hill et al. |
| 6,423,029 B1 | 7/2002 | Elsberry | 6,542,775 B2 | 4/2003 | Ding et al. |
| 6,423,035 B1 | 7/2002 | Das et al. | 6,550,245 B2 | 4/2003 | Nishii et al. |
| 6,423,344 B1 | 7/2002 | Platz et al. | 6,551,276 B1 | 4/2003 | Mann et al. |
| 6,425,740 B1 | 7/2002 | Jacobsen et al. | 6,551,992 B1 | 4/2003 | DeFelippis et al. |
| 6,427,088 B1 | 7/2002 | Bowman, IV et al. | 6,553,245 B1 | 4/2003 | Grace et al. |
| 6,428,491 B1 | 8/2002 | Weiss | 6,554,798 B1 | 4/2003 | Mann et al. |
| 6,429,197 B1 | 8/2002 | Coolidge et al. | 6,557,454 B2 | 5/2003 | Miyazawa |
| 6,429,230 B1 | 8/2002 | Cavazza | 6,558,320 B1 | 5/2003 | Causey et al. |
| 6,429,232 B1 | 8/2002 | Kinsella et al. | 6,558,345 B1 | 5/2003 | Houben et al. |
| 6,433,040 B1 | 8/2002 | Dellamary et al. | 6,558,351 B1 | 5/2003 | Steil et al. |
| 6,436,072 B1 | 8/2002 | Kullas et al. | 6,558,665 B1 | 5/2003 | Cohen et al. |
| 6,436,078 B1 | 8/2002 | Svedman | 6,558,902 B1 | 5/2003 | Hillenkamp |
| 6,438,408 B1 | 8/2002 | Mulligan et al. | 6,560,478 B1 | 5/2003 | Alfano et al. |
| 6,440,096 B1 | 8/2002 | Lastovich et al. | 6,562,001 B2 | 5/2003 | Lebel et al. |
| 6,441,036 B1 | 8/2002 | Berge | 6,564,093 B1 | 5/2003 | Ostrow et al. |
| 6,443,097 B1 | 9/2002 | Zohar et al. | 6,564,104 B2 | 5/2003 | Nelson et al. |
| 6,443,942 B2 | 9/2002 | Van Antwerp | 6,564,105 B2 | 5/2003 | Starkweather et al. |
| 6,446,513 B1 | 9/2002 | Henderson | 6,565,802 B1 | 5/2003 | Hanley et al. |
| 6,447,443 B1 | 9/2002 | Keogh et al. | 6,565,872 B2 | 5/2003 | Wu et al. |
| 6,447,446 B1 | 9/2002 | Smith et al. | 6,568,898 B2 | 5/2003 | Nishimura et al. |
| 6,447,475 B1 | 9/2002 | Castellano et al. | 6,568,922 B1 | 5/2003 | Winsel |
| 6,447,522 B2 | 9/2002 | Gambale et al. | 6,569,123 B2 | 5/2003 | Alchas et al. |
| 6,450,942 B1 | 9/2002 | Lapanashvili et al. | 6,569,143 B2 | 5/2003 | Alchas et al. |
| 6,454,707 B1 | 9/2002 | Casscells, III | 6,569,456 B2 | 5/2003 | Faour et al. |
| 6,454,785 B2 | 9/2002 | De Hoyos Garza | 6,571,128 B2 | 5/2003 | Lebel et al. |
| 6,457,956 B1 | 10/2002 | Hauser et al. | 6,571,831 B1 | 6/2003 | Hart |
| 6,458,102 B1 | 10/2002 | Mann et al. | 6,572,542 B1 | 6/2003 | Houben et al. |
| 6,458,109 B1 | 10/2002 | Henley et al. | 6,572,566 B2 | 6/2003 | Effenhauser |
| 6,458,256 B1 | 10/2002 | Zhong | 6,577,899 B2 | 6/2003 | Lebel et al. |
| 6,458,762 B1 | 10/2002 | McKenzie et al. | 6,579,496 B1 | 6/2003 | Fausset et al. |
| 6,461,329 B1 | 10/2002 | Van Antwerp et al. | 6,582,366 B1 | 6/2003 | Porumbescu |
| 6,461,331 B1 | 10/2002 | Van Antwerp | 6,582,393 B2 | 6/2003 | Sage, Jr. |
| 6,461,334 B1 | 10/2002 | Buch-Rasmussen et al. | 6,582,418 B1 | 6/2003 | Verbeek et al. |
| 6,461,828 B1 | 10/2002 | Stanton et al. | 6,583,111 B1 | 6/2003 | DiMarchi et al. |
| 6,463,794 B1 | 10/2002 | Moshe et al. | 6,585,644 B2 | 7/2003 | Lebel et al. |
| 6,464,667 B1 | 10/2002 | Kamen et al. | 6,585,707 B2 | 7/2003 | Cabiri et al. |
| 6,467,267 B2 | 10/2002 | Kanazawa et al. | 6,589,158 B2 | 7/2003 | Winkler |
| 6,468,200 B1 | 10/2002 | Fischi | 6,589,229 B1 | 7/2003 | Connelly et al. |
| 6,469,016 B1 | 10/2002 | Place et al. | 6,592,544 B1 | 7/2003 | Mooney et al. |
| 6,471,496 B1 | 10/2002 | Merklein et al. | 6,592,571 B1 | 7/2003 | Verbeek et al. |
| 6,471,689 B1 | 10/2002 | Joseph et al. | 6,592,860 B1 | 7/2003 | Levy et al. |
| 6,471,855 B1 | 10/2002 | Odak et al. | 6,592,904 B2 | 7/2003 | Platz et al. |
| 6,472,434 B1 | 10/2002 | Place et al. | 6,593,313 B2 | 7/2003 | Place et al. |
| 6,474,219 B2 | 11/2002 | Kitmose et al. | 6,595,756 B2 | 7/2003 | Gray et al. |
| 6,475,180 B2 | 11/2002 | Peterson et al. | 6,595,948 B2 | 7/2003 | Suzuki et al. |
| 6,475,750 B1 | 11/2002 | Han et al. | 6,595,956 B1 | 7/2003 | Gross et al. |
| 6,477,774 B1 | 11/2002 | Marando et al. | 6,599,281 B1 | 7/2003 | Struys et al. |
| 6,478,385 B1 | 11/2002 | Nishii et al. | 6,602,241 B2 | 8/2003 | Makower et al. |
| 6,478,771 B1 | 11/2002 | Lavi et al. | 6,604,908 B1 | 8/2003 | Bryant et al. |
| 6,482,186 B1 | 11/2002 | Douglas et al. | 6,605,072 B2 | 8/2003 | Struys et al. |
| 6,484,906 B2 | 11/2002 | Bonningue | 6,607,513 B1 | 8/2003 | Down et al. |
| 6,485,263 B1 | 11/2002 | Bryant et al. | 6,607,658 B1 | 8/2003 | Heller et al. |
| 6,485,452 B1 | 11/2002 | French et al. | 6,607,739 B1 | 8/2003 | Wallo |
| 6,485,461 B1 | 11/2002 | Mason et al. | 6,610,003 B1 | 8/2003 | Meloul et al. |
| 6,488,652 B1 | 12/2002 | Weijand et al. | 6,612,535 B1 | 9/2003 | Tai et al. |
| 6,488,697 B1 | 12/2002 | Ariura et al. | 6,613,019 B2 | 9/2003 | Munk |
| 6,489,346 B1 | 12/2002 | Phillips | 6,616,196 B1 | 9/2003 | Weh et al. |
| 6,490,483 B2 | 12/2002 | Willis | 6,616,627 B2 | 9/2003 | Willis et al. |
| 6,494,865 B1 | 12/2002 | Alchas | 6,618,603 B2 | 9/2003 | Varalli et al. |
| 6,500,150 B1 | 12/2002 | Gross et al. | 6,620,140 B1 | 9/2003 | Metzger |
| 6,505,059 B1 | 1/2003 | Kollias et al. | 6,620,379 B1 | 9/2003 | Piuk et al. |
| 6,506,594 B1 | 1/2003 | Barany et al. | 6,623,698 B2 | 9/2003 | Kuo |
| 6,508,788 B2 | 1/2003 | Preuthun | 6,626,644 B2 | 9/2003 | Ozaki |
| 6,511,435 B1 | 1/2003 | Bluth et al. | 6,629,934 B2 | 10/2003 | Mault et al. |
| 6,512,949 B1 | 1/2003 | Combs et al. | 6,629,938 B1 | 10/2003 | Engvall et al. |
| 6,514,689 B2 | 2/2003 | Han et al. | 6,629,949 B1 | 10/2003 | Douglas |
| 6,517,482 B1 | 2/2003 | Elden et al. | 6,634,939 B2 | 10/2003 | Johnson |
| 6,522,980 B1 | 2/2003 | Arnold | 6,635,014 B2 | 10/2003 | Starkweather et al. |
| 6,530,900 B1 | 3/2003 | Daily et al. | 6,636,796 B2 | 10/2003 | Kolmanovsky et al. |
| 6,533,183 B2 | 3/2003 | Aasmul et al. | 6,639,381 B2 | 10/2003 | Tamura et al. |
| 6,537,241 B1 | 3/2003 | Odland | 6,641,533 B2 | 11/2003 | Causey et al. |
| 6,537,251 B2 | 3/2003 | Kiltmose | 6,641,562 B1 | 11/2003 | Peterson et al. |
| 6,537,272 B2 | 3/2003 | Christopherson et al. | 6,641,565 B1 | 11/2003 | Lavi et al. |
| 6,540,006 B2 | 4/2003 | Kono | 6,641,566 B2 | 11/2003 | Douglas et al. |
| 6,540,161 B1 | 4/2003 | Gordon | 6,642,019 B1 | 11/2003 | Anderson et al. |
| 6,540,727 B2 | 4/2003 | Harper et al. | 6,645,181 B1 | 11/2003 | Lavi et al. |

| | | | | | | |
|---|---|---|---|---|---|---|
| 6,648,821 | B2 | 11/2003 | Lebel et al. | 6,780,836 | B2 | 8/2004 | Unemori |
| 6,648,859 | B2 | 11/2003 | Bitdinger et al. | 6,783,107 | B2 | 8/2004 | Chatufale |
| 6,648,861 | B2 | 11/2003 | Platt et al. | 6,783,328 | B2 | 8/2004 | Lucke et al. |
| 6,649,403 | B1 | 11/2003 | McDevitt et al. | 6,786,246 | B2 | 9/2004 | Ohms et al. |
| 6,650,919 | B2 | 11/2003 | Edelberg et al. | 6,790,670 | B2 | 9/2004 | Munagavalasa et al. |
| 6,651,546 | B2 | 11/2003 | Sandlin | 6,796,956 | B2 | 9/2004 | Hartlaub et al. |
| 6,656,148 | B2 | 12/2003 | Das et al. | 6,801,420 | B2 | 10/2004 | Talbot et al. |
| 6,656,158 | B2 | 12/2003 | Mahoney et al. | 6,804,002 | B2 | 10/2004 | Fine et al. |
| 6,656,159 | B2 | 12/2003 | Flaherty et al. | 6,804,555 | B2 | 10/2004 | Warkentin |
| 6,663,359 | B2 | 12/2003 | Gray | 6,805,122 | B2 | 10/2004 | Richey, II et al. |
| 6,666,821 | B2 | 12/2003 | Keimel | 6,805,687 | B2 | 10/2004 | Dextradeur et al. |
| 6,668,701 | B1 | 12/2003 | Everitt | 6,808,506 | B2 | 10/2004 | Lastovich et al. |
| 6,669,663 | B1 | 12/2003 | Thompson | 6,810,290 | B2 | 10/2004 | Lebel et al. |
| 6,669,669 | B2 | 12/2003 | Flaherty et al. | RE38,654 | E | 11/2004 | Hill et al. |
| 6,677,320 | B2 | 1/2004 | Diederich et al. | 6,811,534 | B2 | 11/2004 | Bowman, IV et al. |
| 6,682,497 | B2 | 1/2004 | Jensen et al. | 6,811,792 | B2 | 11/2004 | Roser et al. |
| 6,683,690 | B1 | 1/2004 | Tobias | 6,813,519 | B2 | 11/2004 | Lebel et al. |
| 6,689,100 | B2 | 2/2004 | Connelly et al. | 6,813,964 | B1 | 11/2004 | Clark et al. |
| 6,689,108 | B2 | 2/2004 | Lavi et al. | 6,821,249 | B2 | 11/2004 | Casscells, III et al. |
| 6,689,118 | B2 | 2/2004 | Alchas et al. | 6,821,484 | B1 | 11/2004 | Gregersen |
| 6,689,373 | B2 | 2/2004 | Johnson et al. | 6,824,529 | B2 | 11/2004 | Gross et al. |
| 6,692,456 | B1 | 2/2004 | Eppstein et al. | 6,827,524 | B2 | 12/2004 | Starry, Jr. et al. |
| 6,692,457 | B2 | 2/2004 | Flaherty et al. | 6,827,702 | B2 | 12/2004 | Lebel et al. |
| 6,694,191 | B2 | 2/2004 | Starkweather et al. | 6,827,710 | B1 | 12/2004 | Mooney et al. |
| 6,695,011 | B2 | 2/2004 | Sochtig | 6,827,898 | B1 | 12/2004 | Fausset et al. |
| 6,696,090 | B1 | 2/2004 | Nilsson et al. | 6,828,552 | B2 | 12/2004 | Hartley |
| 6,696,493 | B2 | 2/2004 | Cavazza | 6,830,558 | B2 | 12/2004 | Flaherty et al. |
| 6,699,218 | B2 | 3/2004 | Flaherty et al. | 6,830,560 | B1 | 12/2004 | Gross et al. |
| 6,699,234 | B2 | 3/2004 | Yeh et al. | 6,835,175 | B1 | 12/2004 | Porumbescu |
| 6,699,885 | B2 | 3/2004 | Phillips | 6,835,194 | B2 | 12/2004 | Johnson et al. |
| 6,702,779 | B2 | 3/2004 | Connelly et al. | 6,842,642 | B2 | 1/2005 | Vanhout |
| 6,702,857 | B2 | 3/2004 | Brauker et al. | 6,843,782 | B2 | 1/2005 | Gross et al. |
| 6,705,845 | B2 | 3/2004 | Krieger et al. | 6,847,898 | B1 | 1/2005 | Chen et al. |
| 6,706,008 | B2 | 3/2004 | Vishnoi et al. | 6,851,449 | B2 | 2/2005 | Kleibrink |
| 6,706,009 | B2 | 3/2004 | Diermann et al. | 6,852,104 | B2 | 2/2005 | Blomquist |
| 6,706,689 | B2 | 3/2004 | Coolidge et al. | 6,852,487 | B1 | 2/2005 | Barany et al. |
| 6,710,051 | B1 | 3/2004 | Trier | 6,854,432 | B2 | 2/2005 | Hirano |
| 6,711,489 | B2 | 3/2004 | Haskara et al. | 6,854,620 | B2 | 2/2005 | Ramey |
| 6,712,095 | B2 | 3/2004 | Williamson et al. | 6,858,011 | B2 | 2/2005 | Sehgal |
| 6,715,516 | B2 | 4/2004 | Ohms et al. | 6,858,403 | B2 | 2/2005 | Han et al. |
| 6,716,190 | B1 | 4/2004 | Glines et al. | 6,864,101 | B1 | 3/2005 | Winkler et al. |
| 6,718,206 | B2 | 4/2004 | Casavante | 6,867,196 | B1 | 3/2005 | Wolff et al. |
| 6,719,302 | B2 | 4/2004 | Andrick | 6,868,358 | B2 | 3/2005 | Brown, Jr. |
| 6,723,068 | B2 | 4/2004 | Lavi et al. | 6,872,200 | B2 | 3/2005 | Mann et al. |
| 6,723,072 | B2 | 4/2004 | Flaherty et al. | 6,873,268 | B2 | 3/2005 | Lebel et al. |
| 6,726,920 | B1 | 4/2004 | Theeuwes et al. | 6,876,885 | B2 | 4/2005 | Swoyer et al. |
| 6,732,573 | B2 | 5/2004 | Shin et al. | 6,877,713 | B1 | 4/2005 | Gray et al. |
| 6,733,446 | B2 | 5/2004 | Lebel et al. | 6,880,564 | B2 | 4/2005 | Erickson |
| 6,734,186 | B1 | 5/2004 | Maw et al. | 6,884,122 | B2 | 4/2005 | Robinson et al. |
| 6,736,796 | B2 | 5/2004 | Shekalim et al. | 6,884,228 | B2 | 4/2005 | Brown et al. |
| 6,738,663 | B2 | 5/2004 | Schroppel et al. | 6,885,881 | B2 | 4/2005 | Leonhardt |
| 6,738,707 | B2 | 5/2004 | Kotwicki et al. | 6,885,888 | B2 | 4/2005 | Rezai |
| 6,740,059 | B2 | 5/2004 | Flaherty et al. | 6,886,556 | B2 | 5/2005 | Fuchs |
| 6,740,072 | B2 | 5/2004 | Starkweather et al. | 6,892,755 | B2 | 5/2005 | Black |
| 6,740,075 | B2 | 5/2004 | Lebel et al. | 6,892,900 | B2 * | 5/2005 | Drechsel ........................ 222/55 |
| 6,743,201 | B1 | 6/2004 | Donig et al. | 6,894,024 | B2 | 5/2005 | Coolidge et al. |
| 6,744,152 | B2 | 6/2004 | Kroll | 6,896,666 | B2 | 5/2005 | Kochamba |
| 6,745,079 | B2 | 6/2004 | King | 6,899,699 | B2 | 5/2005 | Enggaard |
| 6,746,438 | B1 | 6/2004 | Arnissolle | RE38,749 | E | 6/2005 | Dardik |
| 6,748,930 | B2 | 6/2004 | Bofinger et al. | 6,905,479 | B1 | 6/2005 | Bouchard et al. |
| 6,749,403 | B2 | 6/2004 | Bryant et al. | 6,906,028 | B2 | 6/2005 | Defelippis et al. |
| 6,749,587 | B2 | 6/2004 | Flaherty et al. | 6,908,591 | B2 | 6/2005 | MacPhee et al. |
| 6,752,785 | B2 | 6/2004 | Van Antwerp et al. | 6,909,840 | B2 | 6/2005 | Harwig et al. |
| 6,752,787 | B1 | 6/2004 | Causey, III et al. | 6,912,425 | B2 | 6/2005 | Nova et al. |
| 6,755,628 | B1 | 6/2004 | Howell | 6,913,933 | B2 | 7/2005 | Jacobs et al. |
| 6,758,593 | B1 | 7/2004 | Terentiev | 6,914,076 | B2 | 7/2005 | Cavazza |
| 6,759,386 | B2 | 7/2004 | Franco | 6,916,159 | B2 | 7/2005 | Rush et al. |
| 6,767,188 | B2 | 7/2004 | Vrane et al. | 6,918,542 | B2 | 7/2005 | Silverbrook et al. |
| 6,767,896 | B1 | 7/2004 | McIntosh et al. | 6,923,180 | B2 | 8/2005 | Richey, II et al. |
| 6,768,425 | B2 | 7/2004 | Flaherty et al. | 6,923,764 | B2 | 8/2005 | Aceti et al. |
| 6,769,384 | B2 | 8/2004 | Dougherty | 6,926,694 | B2 | 8/2005 | Marano-Ford et al. |
| 6,770,054 | B1 | 8/2004 | Smolyarov et al. | 6,930,093 | B2 | 8/2005 | Brantl |
| 6,773,669 | B1 | 8/2004 | Holaday et al. | 6,931,845 | B2 | 8/2005 | Schaeffer |
| 6,773,739 | B2 | 8/2004 | Hauck et al. | 6,931,925 | B2 | 8/2005 | Huemer et al. |
| 6,776,776 | B2 | 8/2004 | Alchas et al. | 6,932,114 | B2 | 8/2005 | Sparks |
| 6,780,156 | B2 | 8/2004 | Haueter et al. | 6,932,796 | B2 | 8/2005 | Sage et al. |
| 6,780,171 | B2 | 8/2004 | Gabel et al. | 6,935,531 | B1 | 8/2005 | Clayton |
| 6,780,426 | B2 | 8/2004 | Zhang et al. | 6,935,539 | B2 | 8/2005 | Krieger et al. |
| 6,780,770 | B2 | 8/2004 | Larson | 6,936,026 | B2 | 8/2005 | Diermann et al. |

| Patent | Type | Date | Inventor |
|---|---|---|---|
| 6,936,029 | B2 | 8/2005 | Mann et al. |
| 6,936,046 | B2 | 8/2005 | Hissong et al. |
| 6,939,323 | B2 | 9/2005 | Angel et al. |
| 6,939,324 | B2 | 9/2005 | Gonneli et al. |
| 6,942,636 | B2 | 9/2005 | Holst et al. |
| 6,943,034 | B1 | 9/2005 | Winkler et al. |
| 6,946,117 | B1 | 9/2005 | Schutt et al. |
| 6,948,918 | B2 | 9/2005 | Hansen |
| 6,949,081 | B1 | 9/2005 | Chance |
| 6,950,708 | B2 | 9/2005 | Bowman, IV et al. |
| 6,951,165 | B2 | 10/2005 | Kuhn et al. |
| 6,951,553 | B2 | 10/2005 | Bubb et al. |
| 6,952,604 | B2 | 10/2005 | DeNuzzio et al. |
| 6,952,963 | B2 | 10/2005 | Delnevo |
| 6,955,819 | B2 | 10/2005 | Zhang et al. |
| 6,955,915 | B2 | 10/2005 | Fodor et al. |
| 6,956,204 | B2 | 10/2005 | Dong et al. |
| 6,957,655 | B2 | 10/2005 | Erickson et al. |
| 6,957,924 | B1 | 10/2005 | McMeekin et al. |
| 6,958,073 | B2 | 10/2005 | Rogers et al. |
| 6,958,705 | B2 | 10/2005 | Lebel et al. |
| 6,960,184 | B2 | 11/2005 | Willis et al. |
| 6,960,192 | B1 | 11/2005 | Flaherty et al. |
| 6,962,103 | B2 | 11/2005 | Sandlin |
| 6,962,151 | B1 | 11/2005 | Knoch et al. |
| 6,963,770 | B2 | 11/2005 | Scarantino et al. |
| 6,966,325 | B2 | 11/2005 | Erickson |
| 6,969,369 | B2 | 11/2005 | Struble |
| 6,970,741 | B1 | 11/2005 | Whitehurst et al. |
| 6,970,742 | B2 | 11/2005 | Mann et al. |
| 6,971,999 | B2 | 12/2005 | Py et al. |
| 6,974,055 | B2 | 12/2005 | Moore et al. |
| 6,974,115 | B2 | 12/2005 | Silva |
| 6,974,437 | B2 | 12/2005 | Lebel et al. |
| 6,974,588 | B1 | 12/2005 | Miranda et al. |
| 6,979,308 | B1 | 12/2005 | MacDonald et al. |
| 6,979,316 | B1 | 12/2005 | Rubin et al. |
| 6,979,326 | B2 | 12/2005 | Mann et al. |
| 6,980,855 | B2 | 12/2005 | Cho |
| 6,981,499 | B2 | 1/2006 | Anderson |
| 6,981,967 | B2 | 1/2006 | Massengale et al. |
| 6,982,248 | B2 | 1/2006 | Coolidge et al. |
| 6,983,209 | B2 | 1/2006 | Jaynes |
| 6,985,770 | B2 | 1/2006 | Nyhart, Jr. |
| 6,985,771 | B2 | 1/2006 | Fischell et al. |
| 6,986,867 | B2 | 1/2006 | Hanley et al. |
| 6,987,129 | B2 | 1/2006 | Mak et al. |
| 6,990,809 | B2 | 1/2006 | Abouraphael |
| 6,991,619 | B2 | 1/2006 | Marano-Ford et al. |
| 6,991,620 | B2 | 1/2006 | Marano-Ford et al. |
| 6,993,795 | B2 | 2/2006 | Prineppi |
| 6,994,700 | B2 | 2/2006 | Elkins et al. |
| 6,997,202 | B2 | 2/2006 | Olander |
| 6,997,911 | B2 | 2/2006 | Klitmose |
| 6,997,920 | B2 | 2/2006 | Mann et al. |
| 6,998,387 | B1 | 2/2006 | Goke et al. |
| 6,998,404 | B2 | 2/2006 | Moskowitz |
| 6,999,854 | B2 | 2/2006 | Roth |
| 7,004,928 | B2 | 2/2006 | Aceti et al. |
| 7,008,399 | B2 | 3/2006 | Larson et al. |
| 7,008,403 | B1 | 3/2006 | Mallett |
| 7,010,340 | B2 | 3/2006 | Scarantino et al. |
| 7,011,647 | B2 | 3/2006 | Purdy et al. |
| 7,011,682 | B2 | 3/2006 | Lashinski et al. |
| 7,013,727 | B2 | 3/2006 | Delnevo |
| 7,015,782 | B2 | 3/2006 | Kincaid et al. |
| 7,018,360 | B2 | 3/2006 | Flaherty et al. |
| 7,018,361 | B2 | 3/2006 | Gillespie, Jr. et al. |
| 7,018,630 | B2 | 3/2006 | Takaoka |
| 7,022,071 | B2 | 4/2006 | Schaupp et al. |
| 7,022,072 | B2 | 4/2006 | Fox et al. |
| 7,022,087 | B2 | 4/2006 | Dempster et al. |
| 7,022,108 | B2 | 4/2006 | Marano-Ford et al. |
| 7,024,244 | B2 | 4/2006 | Muhlenberg et al. |
| 7,024,245 | B2 | 4/2006 | Lebel et al. |
| 7,025,716 | B1 | 4/2006 | Meloul et al. |
| 7,025,743 | B2 | 4/2006 | Mann et al. |
| 7,027,478 | B2 | 4/2006 | Ackley |
| 7,029,455 | B2 | 4/2006 | Flaherty |
| 7,033,843 | B2 | 4/2006 | Hasegawa et al. |
| 7,047,070 | B2 | 5/2006 | Wilkinson et al. |
| 7,048,193 | B2 | 5/2006 | Tsukada et al. |
| 7,048,951 | B1 | 5/2006 | Seitz et al. |
| 7,052,251 | B2 | 5/2006 | Nason et al. |
| 7,053,761 | B2 | 5/2006 | Schofield et al. |
| 7,056,179 | B2 | 6/2006 | Courtney |
| 7,056,302 | B2 | 6/2006 | Douglas |
| 7,056,494 | B2 | 6/2006 | Adjei et al. |
| 7,056,887 | B2 | 6/2006 | Coolidge et al. |
| 7,058,438 | B2 | 6/2006 | Grace et al. |
| 7,059,348 | B2 | 6/2006 | Nat |
| 7,060,856 | B2 | 6/2006 | Macikenas et al. |
| 7,064,472 | B2 | 6/2006 | Pelrine et al. |
| 7,066,359 | B2 | 6/2006 | Greiner-Perth |
| 7,066,910 | B2 | 6/2006 | Bauhahn et al. |
| 7,066,915 | B2 | 6/2006 | Olsen |
| 7,066,922 | B2 | 6/2006 | Angel et al. |
| 7,069,075 | B2 | 6/2006 | Olson |
| 7,070,577 | B1 | 7/2006 | Haller et al. |
| 7,073,485 | B2 | 7/2006 | Truscott et al. |
| 7,073,713 | B2 | 7/2006 | Silverbrook et al. |
| 7,074,200 | B1 | 7/2006 | Lewis |
| 7,077,822 | B1 | 7/2006 | Howard, III |
| 7,078,163 | B2 | 7/2006 | Torrianni |
| 7,081,105 | B2 | 7/2006 | Reilly et al. |
| 7,082,812 | B2 | 8/2006 | Lenormand et al. |
| 7,083,108 | B2 | 8/2006 | Silverbrook et al. |
| 7,083,592 | B2 | 8/2006 | Lastovich et al. |
| 7,083,599 | B2 | 8/2006 | Alchas et al. |
| 7,089,608 | B2 | 8/2006 | Erb |
| 7,090,648 | B2 | 8/2006 | Sackner et al. |
| 7,091,179 | B2 | 8/2006 | Franco |
| 7,092,011 | B2 | 8/2006 | Silverbrook et al. |
| 7,095,210 | B2 | 8/2006 | Tamura et al. |
| 7,096,889 | B1 | 8/2006 | Roys |
| 7,097,104 | B2 | 8/2006 | Silverbrook et al. |
| 7,098,803 | B2 | 8/2006 | Mann et al. |
| 7,104,973 | B2 | 9/2006 | Woolston et al. |
| 7,104,981 | B2 | 9/2006 | Elkins et al. |
| 7,107,706 | B1 | 9/2006 | Bailey, Sr. et al. |
| 7,108,491 | B2 | 9/2006 | Ganser |
| 7,108,679 | B2 | 9/2006 | Alchas |
| 7,109,878 | B2 | 9/2006 | Mann et al. |
| 7,111,346 | B2 | 9/2006 | Inman et al. |
| 7,115,108 | B2 | 10/2006 | Wilkinson et al. |
| 7,118,351 | B2 | 10/2006 | Effenhauser et al. |
| 7,118,676 | B2 | 10/2006 | Mueth et al. |
| 7,122,151 | B2 | 10/2006 | Reeder et al. |
| 7,127,292 | B2 | 10/2006 | Warman et al. |
| 7,128,727 | B2 | 10/2006 | Flaherty et al. |
| 7,128,730 | B2 | 10/2006 | Marano-Ford et al. |
| 7,133,329 | B2 | 11/2006 | Skyggebjerg et al. |
| 7,136,701 | B2 | 11/2006 | Greatbatch et al. |
| 7,137,951 | B2 | 11/2006 | Pilarski |
| 7,137,964 | B2 | 11/2006 | Flaherty et al. |
| 7,138,141 | B2 | 11/2006 | Platz et al. |
| 7,140,332 | B2 | 11/2006 | Klein et al. |
| 7,141,425 | B2 | 11/2006 | Dzekunov et al. |
| 7,141,812 | B2 | 11/2006 | Appleby et al. |
| 7,144,384 | B2 | 12/2006 | Gorman et al. |
| 7,144,729 | B2 | 12/2006 | Rolland et al. |
| 7,147,386 | B2 | 12/2006 | Zhang et al. |
| 7,147,839 | B2 | 12/2006 | Sampath et al. |
| 7,150,409 | B2 | 12/2006 | Gonneli et al. |
| 7,150,726 | B2 | 12/2006 | Dalton |
| 7,150,737 | B2 | 12/2006 | Purdy et al. |
| 7,150,741 | B2 | 12/2006 | Erickson et al. |
| 7,152,673 | B2 | 12/2006 | Lohbeck |
| 7,153,286 | B2 | 12/2006 | Busby et al. |
| 7,153,823 | B2 | 12/2006 | Franco |
| 7,156,808 | B2 | 1/2007 | Quy |
| 7,156,838 | B2 | 1/2007 | Gabel et al. |
| 7,159,271 | B2 | 1/2007 | Sepke et al. |
| 7,162,303 | B2 | 1/2007 | Levin et al. |
| 7,163,385 | B2 | 1/2007 | Gharib et al. |
| 7,163,520 | B2 | 1/2007 | Bernard et al. |
| 7,166,280 | B2 | 1/2007 | Franco |
| 7,187,404 | B2 | 3/2007 | Silverbrook et al. |

| | | | | | | |
|---|---|---|---|---|---|---|
| 7,187,528 B2 | 3/2007 | Talbot et al. | | 7,323,141 B2 | 1/2008 | Kirchhevel |
| 7,187,969 B2 | 3/2007 | Willis | | 7,323,543 B2 | 1/2008 | Van Antwerp et al. |
| 7,189,352 B2 | 3/2007 | Carpenter et al. | | 7,324,012 B2 | 1/2008 | Mann et al. |
| 7,193,521 B2 | 3/2007 | Moberg et al. | | 7,334,556 B2 | 2/2008 | Wachigai et al. |
| 7,194,890 B2 | 3/2007 | Tanaka et al. | | 7,335,377 B2 | 2/2008 | Stern et al. |
| 7,195,616 B2 | 3/2007 | Diller et al. | | 7,338,464 B2 | 3/2008 | Blischak et al. |
| 7,198,603 B2 | 4/2007 | Penner et al. | | 7,341,577 B2 | 3/2008 | Gill |
| 7,198,637 B2 | 4/2007 | Deshmukh et al. | | 7,341,581 B2 | 3/2008 | Mallett |
| 7,198,751 B2 | 4/2007 | Carpenter et al. | | 7,344,500 B2 | 3/2008 | Talbot et al. |
| 7,198,940 B2 | 4/2007 | Vellinger et al. | | 7,344,507 B2 | 3/2008 | Briggs et al. |
| 7,201,319 B2 | 4/2007 | Silverbrook et al. | | 7,344,894 B2 | 3/2008 | Greenstein et al. |
| 7,201,730 B2 | 4/2007 | Davidner et al. | | 7,347,201 B2 | 3/2008 | Djupesland |
| 7,204,823 B2 | 4/2007 | Estes et al. | | 7,347,836 B2 | 3/2008 | Peterson et al. |
| 7,204,958 B2 | 4/2007 | Olsen et al. | | 7,348,176 B2 | 3/2008 | DiMilla et al. |
| 7,207,952 B2 | 4/2007 | Takinami et al. | | 7,351,239 B2 | 4/2008 | Gill |
| 7,207,964 B2 | 4/2007 | Davidner et al. | | 7,351,411 B2 | 4/2008 | Holash et al. |
| 7,208,120 B2 | 4/2007 | Bitensky et al. | | 7,351,695 B2 | 4/2008 | Almarssoo et al. |
| 7,214,207 B2 | 5/2007 | Lynch et al. | | 7,357,794 B2 | 4/2008 | Makower et al. |
| 7,214,221 B2 | 5/2007 | Fentress et al. | | 7,357,899 B2 | 4/2008 | Gaillard et al. |
| 7,214,658 B2 | 5/2007 | Tobinick | | 7,358,091 B2 | 4/2008 | Phillips et al. |
| 7,217,699 B2 | 5/2007 | Yakubov | | 7,361,155 B2 | 4/2008 | Sage, Jr. et al. |
| 7,217,796 B2 | 5/2007 | Wang et al. | | 7,362,971 B2 | 4/2008 | Silverbrook et al. |
| 7,220,236 B2 | 5/2007 | Pan | | 7,363,072 B2 | 4/2008 | Movahed |
| 7,220,248 B2 | 5/2007 | Mernoe et al. | | 7,363,075 B2 | 4/2008 | Stern et al. |
| 7,220,365 B2 | 5/2007 | Qu et al. | | 7,364,566 B2 | 4/2008 | Elkins et al. |
| 7,225,807 B2 | 6/2007 | Papania et al. | | 7,364,568 B2 | 4/2008 | Angel et al. |
| 7,226,278 B2 | 6/2007 | Nason et al. | | 7,366,925 B2 | 4/2008 | Keely et al. |
| 7,226,910 B2 | 6/2007 | Wilson et al. | | 7,368,003 B2 | 5/2008 | Crapser et al. |
| 7,229,288 B2 | 6/2007 | Stuart et al. | | 7,371,418 B2 | 5/2008 | Sheabar et al. |
| 7,232,423 B2 | 6/2007 | Mernoe et al. | | 7,373,083 B2 | 5/2008 | Silverbrook et al. |
| 7,232,430 B2 | 6/2007 | Carlisle et al. | | 7,373,690 B2 | 5/2008 | Sepke et al. |
| 7,232,435 B2 | 6/2007 | Hildebrand et al. | | 7,374,544 B2 | 5/2008 | Freeman et al. |
| 7,234,645 B2 | 6/2007 | Silverbrook | | 7,374,556 B2 | 5/2008 | Mallett |
| 7,235,164 B2 | 6/2007 | Anex et al. | | 7,377,706 B2 | 5/2008 | Silverbrook et al. |
| 7,235,583 B1 | 6/2007 | Webb et al. | | 7,377,907 B2 | 5/2008 | Shekalim et al. |
| 7,237,694 B2 | 7/2007 | Freudinger | | 7,378,270 B2 | 5/2008 | Azarnia et al. |
| 7,238,165 B2 | 7/2007 | Vincent et al. | | 7,378,443 B2 | 5/2008 | Berge |
| 7,244,225 B2 | 7/2007 | Loeb et al. | | 7,380,447 B2 | 6/2008 | Rollinger et al. |
| 7,244,354 B2 | 7/2007 | Burris et al. | | 7,384,413 B2 | 6/2008 | Gross et al. |
| 7,247,428 B2 | 7/2007 | Makrigiorgos | | 7,384,912 B2 | 6/2008 | Stewart |
| 7,247,702 B2 | 7/2007 | Gardner et al. | | 7,385,443 B1 | 6/2008 | Denison |
| 7,250,037 B2 | 7/2007 | Shermer et al. | | 7,386,346 B2 | 6/2008 | Struble |
| 7,251,516 B2 | 7/2007 | Walker et al. | | 7,390,311 B2 | 6/2008 | Hildebrand et al. |
| 7,252,014 B1 | 8/2007 | Mayer et al. | | 7,390,458 B2 | 6/2008 | Burow et al. |
| 7,252,651 B2 | 8/2007 | Haider et al. | | 7,394,182 B2 | 7/2008 | Pelrine et al. |
| 7,256,824 B2 | 8/2007 | Silverbrook et al. | | 7,399,277 B2 | 7/2008 | Saidara et al. |
| 7,258,864 B2 | 8/2007 | Clark | | 7,399,304 B2 | 7/2008 | Gambale et al. |
| RE39,816 E | 9/2007 | Stanton et al. | | 7,399,401 B2 | 7/2008 | Rush |
| 7,265,091 B2 | 9/2007 | Lue et al. | | 7,399,772 B2 | 7/2008 | Phillips |
| 7,267,665 B2 | 9/2007 | Steil et al. | | 7,402,153 B2 | 7/2008 | Steil et al. |
| 7,267,753 B2 | 9/2007 | Anex et al. | | 7,402,154 B2 | 7/2008 | Holst et al. |
| 7,267,771 B2 | 9/2007 | Gorsuch et al. | | 7,407,489 B2 | 8/2008 | Holst et al. |
| 7,268,859 B2 | 9/2007 | Sage, Jr. et al. | | 7,407,490 B2 | 8/2008 | Bendsen et al. |
| 7,272,544 B2 | 9/2007 | Gopal et al. | | 7,410,468 B2 | 8/2008 | Freeman et al. |
| 7,276,027 B2 | 10/2007 | Haar et al. | | 7,411,204 B2 | 8/2008 | Appleby et al. |
| 7,276,057 B2 | 10/2007 | Gerber | | 7,416,644 B2 | 8/2008 | Bonde |
| 7,278,983 B2 | 10/2007 | Ireland et al. | | 7,421,316 B2 | 9/2008 | Gray et al. |
| 7,281,519 B2 | 10/2007 | Schroeder et al. | | 7,421,882 B2 | 9/2008 | Leddy et al. |
| 7,285,293 B2 | 10/2007 | Castillo et al. | | 7,425,204 B2 | 9/2008 | Angel et al. |
| 7,287,289 B1 | 10/2007 | Hagopian | | 7,426,408 B2 | 9/2008 | DeNuzzio et al. |
| 7,287,485 B2 | 10/2007 | Petrakis | | 7,429,255 B2 | 9/2008 | Thompson |
| 7,288,760 B2 | 10/2007 | Weitz | | 7,429,258 B2 | 9/2008 | Angel et al. |
| 7,289,142 B2 | 10/2007 | Silverbrook | | 7,429,269 B2 | 9/2008 | Schwammenthal et al. |
| 7,291,126 B2 | 11/2007 | Shekalim et al. | | 7,435,250 B2 | 10/2008 | Francischelli et al. |
| 7,291,133 B1 | 11/2007 | Kindler et al. | | 7,435,717 B2 | 10/2008 | Bisgaier et al. |
| 7,297,151 B2 | 11/2007 | Boecker et al. | | 7,440,806 B1 | 10/2008 | Whitehurst et al. |
| 7,302,295 B2 | 11/2007 | Stahmann et al. | | 7,442,682 B2 | 10/2008 | Kitaura et al. |
| 7,303,543 B1 | 12/2007 | Maule et al. | | RE40,570 E | 11/2008 | Carpentier et al. |
| 7,303,549 B2 | 12/2007 | Flaherty et al. | | 7,445,616 B2 | 11/2008 | Petrakis |
| 7,304,033 B2 | 12/2007 | Larsen et al. | | 7,446,091 B2 | 11/2008 | Van Den Berghe |
| 7,305,975 B2 | 12/2007 | Reddy | | 7,449,333 B2 | 11/2008 | Rolland et al. |
| 7,306,555 B2 | 12/2007 | Dolecek et al. | | 7,452,301 B2 | 11/2008 | Yoshioka |
| 7,306,578 B2 | 12/2007 | Gray et al. | | 7,455,835 B2 | 11/2008 | Cohen et al. |
| 7,311,693 B2 | 12/2007 | Shekalim et al. | | 7,459,305 B2 | 12/2008 | Levy |
| 7,316,700 B2 | 1/2008 | Alden et al. | | 7,460,152 B2 | 12/2008 | Silverbrook et al. |
| 7,316,899 B2 | 1/2008 | McDevitt et al. | | 7,460,350 B2 | 12/2008 | Talbot et al. |
| 7,320,675 B2 | 1/2008 | Pastore et al. | | 7,463,934 B2 | 12/2008 | Tronnes et al. |
| 7,320,677 B2 | 1/2008 | Brouillette et al. | | 7,464,580 B2 | 12/2008 | Zeng et al. |
| 7,322,321 B2 | 1/2008 | Robinson | | 7,464,704 B2 | 12/2008 | Braithwaite |

| Patent | Kind | Date | Inventor |
|---|---|---|---|
| 7,465,285 | B2 | 12/2008 | Hutchinson et al. |
| 7,465,375 | B2 | 12/2008 | Demers et al. |
| 7,467,027 | B2 | 12/2008 | Ding et al. |
| 7,467,613 | B2 | 12/2008 | Taylor, Sr. |
| 7,469,697 | B2 | 12/2008 | Lee et al. |
| 7,469,844 | B2 | 12/2008 | Conway et al. |
| 7,470,246 | B2 | 12/2008 | Mori et al. |
| 7,473,247 | B2 | 1/2009 | Mikszta et al. |
| 7,474,968 | B2 | 1/2009 | Ding et al. |
| 7,475,825 | B2 | 1/2009 | Silverbrook et al. |
| 7,476,200 | B2 | 1/2009 | Tal |
| 7,476,209 | B2 | 1/2009 | Gara et al. |
| 7,479,123 | B2 | 1/2009 | Briggs |
| 7,481,218 | B2 | 1/2009 | Djupesland |
| 7,481,759 | B2 | 1/2009 | Whitehurst et al. |
| 7,481,776 | B2 | 1/2009 | Boecker et al. |
| 7,481,792 | B2 | 1/2009 | Gonnelli et al. |
| 7,483,050 | B2 | 1/2009 | Silverbrook et al. |
| 7,483,743 | B2 | 1/2009 | Mann et al. |
| 7,485,298 | B2 | 2/2009 | Powell |
| 7,491,178 | B2 | 2/2009 | Boecker et al. |
| 7,491,187 | B2 | 2/2009 | Van Den Berghe et al. |
| 7,491,335 | B2 | 2/2009 | Reddy et al. |
| 7,493,154 | B2 | 2/2009 | Bonner et al. |
| 7,493,171 | B1 | 2/2009 | Whitehurst et al. |
| 7,497,841 | B2 | 3/2009 | Alchas |
| 7,503,903 | B2 | 3/2009 | Carlisle et al. |
| 7,507,220 | B2 | 3/2009 | Childers et al. |
| 7,507,235 | B2 | 3/2009 | Keogh et al. |
| 7,509,169 | B2 | 3/2009 | Eigler et al. |
| 7,511,914 | B2 | 3/2009 | Hiller et al. |
| 7,514,075 | B2 | 4/2009 | Hedrick et al. |
| 7,514,401 | B2 | 4/2009 | Franco |
| 7,515,060 | B2 | 4/2009 | Blomquist |
| 7,517,335 | B2 | 4/2009 | Gravesen et al. |
| 7,517,440 | B2 | 4/2009 | Anex et al. |
| 7,517,498 | B2 | 4/2009 | Fredrick |
| 7,517,530 | B2 | 4/2009 | Clark |
| 7,524,045 | B2 | 4/2009 | Silverbrook et al. |
| 7,524,287 | B2 | 4/2009 | Bharmi |
| 7,524,293 | B2 | 4/2009 | Freeman et al. |
| 7,524,304 | B2 | 4/2009 | Genosar |
| 7,530,968 | B2 | 5/2009 | Gonnelli |
| 7,530,975 | B2 | 5/2009 | Hunter |
| 7,534,221 | B2 | 5/2009 | Pile-Spellman |
| 7,534,226 | B2 | 5/2009 | Mernoe et al. |
| 7,536,983 | B2 | 5/2009 | Layher et al. |
| 7,537,571 | B2 | 5/2009 | Freeman et al. |
| 7,540,859 | B2 | 6/2009 | Claude et al. |
| 7,540,880 | B2 | 6/2009 | Nolting |
| 7,543,581 | B2 | 6/2009 | Djupesland |
| 7,547,287 | B2 | 6/2009 | Boecker et al. |
| 7,548,314 | B2 | 6/2009 | Altobelli et al. |
| 7,551,202 | B2 | 6/2009 | Silverbrook |
| 7,553,813 | B2 | 6/2009 | Unemori |
| 7,556,613 | B2 | 7/2009 | Wittmann et al. |
| 7,556,841 | B2 | 7/2009 | Kimball et al. |
| 7,558,629 | B2 | 7/2009 | Keimel et al. |
| 7,559,223 | B2 | 7/2009 | Chen et al. |
| 7,559,524 | B2 | 7/2009 | Gray et al. |
| 7,563,232 | B2 | 7/2009 | Freeman et al. |
| 7,563,255 | B2 | 7/2009 | Adamis et al. |
| 7,572,789 | B2 | 8/2009 | Cowen et al. |
| 7,577,477 | B2 | 8/2009 | Allen et al. |
| 7,582,063 | B2 | 9/2009 | Wurster et al. |
| 7,582,099 | B2 | 9/2009 | Freeman et al. |
| 7,584,846 | B2 | 9/2009 | Senter |
| 7,588,046 | B1 | 9/2009 | Erickson |
| 7,588,550 | B2 | 9/2009 | Leonard et al. |
| 7,588,784 | B2 | 9/2009 | Maday et al. |
| 7,589,059 | B2 | 9/2009 | Wolff et al. |
| 7,590,443 | B2 | 9/2009 | Bharmi |
| 7,591,801 | B2 | 9/2009 | Brauker et al. |
| 7,594,889 | B2 | 9/2009 | St. Ores et al. |
| 7,598,031 | B2 | 10/2009 | Liew |
| 7,602,310 | B2 | 10/2009 | Mann et al. |
| 7,603,174 | B2 | 10/2009 | De Ridder |
| 7,604,592 | B2 | 10/2009 | Freeman et al. |
| 7,604,619 | B2 | 10/2009 | Eich et al. |
| 7,605,710 | B2 | 10/2009 | Crnkovich et al. |
| 7,606,274 | B2 | 10/2009 | Mirov et al. |
| 7,606,615 | B2 | 10/2009 | Makower et al. |
| 7,607,965 | B1 | 10/2009 | Frazier |
| 7,608,640 | B2 | 10/2009 | Messadek |
| 7,615,046 | B2 | 11/2009 | Shehata |
| 7,618,615 | B2 | 11/2009 | Frey, II et al. |
| 7,618,954 | B2 | 11/2009 | Nicolau et al. |
| 7,624,409 | B2 | 11/2009 | Whymark |
| 7,625,369 | B2 | 12/2009 | Abboud et al. |
| 7,628,590 | B2 | 12/2009 | Jacobsen et al. |
| 7,628,772 | B2 | 12/2009 | McConnell et al. |
| 7,632,228 | B2 | 12/2009 | Brauker et al. |
| 7,632,247 | B2 | 12/2009 | Adams |
| 7,632,248 | B2 | 12/2009 | Delk et al. |
| 7,635,575 | B2 | 12/2009 | Scherze et al. |
| 7,637,931 | B2 | 12/2009 | Heaton |
| 7,638,095 | B2 | 12/2009 | Sabol |
| 7,642,232 | B2 | 1/2010 | Green et al. |
| 7,644,203 | B2 | 1/2010 | Ingles |
| 7,645,253 | B2 | 1/2010 | Gura et al. |
| 7,647,107 | B2 | 1/2010 | Warman et al. |
| 7,647,115 | B2 | 1/2010 | Levin et al. |
| 7,647,237 | B2 | 1/2010 | Malave et al. |
| 7,650,181 | B2 | 1/2010 | Freeman et al. |
| 7,650,190 | B2 | 1/2010 | Zhou et al. |
| 7,651,489 | B2 | 1/2010 | Estes et al. |
| 7,651,868 | B2 | 1/2010 | McDevitt et al. |
| 7,653,639 | B2 | 1/2010 | Classen |
| 7,654,127 | B2 | 2/2010 | Krulevitch et al. |
| 7,654,131 | B2 | 2/2010 | Ascheman |
| 7,654,484 | B2 | 2/2010 | Mogensen et al. |
| 7,654,976 | B2 | 2/2010 | Peterson et al. |
| 7,654,982 | B2 | 2/2010 | Carlisle et al. |
| 7,655,221 | B2 | 2/2010 | Rasmussen et al. |
| 7,657,313 | B2 | 2/2010 | Rom |
| 7,662,105 | B2 | 2/2010 | Hatlestad |
| 7,662,140 | B2 | 2/2010 | Heruth et al. |
| 7,662,558 | B2 | 2/2010 | Liew |
| 7,674,243 | B2 | 3/2010 | Dacquay et al. |
| 7,674,485 | B2 | 3/2010 | Bhaskaran et al. |
| 7,676,263 | B2 | 3/2010 | Harris et al. |
| 7,678,071 | B2 | 3/2010 | Lebel et al. |
| 7,678,761 | B2 | 3/2010 | Coleman |
| 7,678,762 | B2 | 3/2010 | Green et al. |
| 7,678,763 | B2 | 3/2010 | Green et al. |
| 7,678,772 | B2 | 3/2010 | Jia et al. |
| 7,678,833 | B2 | 3/2010 | Ott |
| 7,682,430 | B2 | 3/2010 | Kraemer et al. |
| 7,682,563 | B2 | 3/2010 | Carpenter et al. |
| 7,683,029 | B2 | 3/2010 | Hindle et al. |
| 7,685,865 | B2 | 3/2010 | Norenberg |
| 7,687,272 | B2 | 3/2010 | Buchwald et al. |
| RE41,288 | E | 4/2010 | Coolidge et al. |
| 7,691,330 | B1 | 4/2010 | Winkler et al. |
| 7,695,627 | B2 | 4/2010 | Bosch et al. |
| 7,697,995 | B2 | 4/2010 | Cross, Jr. et al. |
| 7,699,767 | B2 | 4/2010 | Mueth et al. |
| 7,699,833 | B2 | 4/2010 | Moberg et al. |
| 7,704,226 | B2 | 4/2010 | Mueller, Jr. et al. |
| 7,704,227 | B2 | 4/2010 | Moberg et al. |
| 7,708,717 | B2 | 5/2010 | Estes et al. |
| 7,708,872 | B2 | 5/2010 | Eidsned et al. |
| 7,708,915 | B2 | 5/2010 | Castor |
| 7,713,240 | B2 | 5/2010 | Istoc et al. |
| 7,713,262 | B2 | 5/2010 | Adams et al. |
| 7,714,757 | B2 | 5/2010 | Denison et al. |
| 7,714,889 | B2 | 5/2010 | Silverbrook |
| 7,715,917 | B2 | 5/2010 | Chinchoy et al. |
| 7,716,964 | B2 | 5/2010 | Kurtz et al. |
| 7,717,856 | B2 | 5/2010 | Chen et al. |
| 7,717,871 | B2 | 5/2010 | Odland |
| 7,717,903 | B2 | 5/2010 | Estes et al. |
| 7,726,955 | B2 | 6/2010 | Ryser et al. |
| 7,727,181 | B2 | 6/2010 | Rush |
| 7,771,414 | B2 | 8/2010 | Trieu |
| 7,811,279 | B2 | 10/2010 | John |
| 7,914,499 | B2 | 3/2011 | Gonneli et al. |
| 7,922,096 | B2 | 4/2011 | Eilersen |

| | | |
|---|---|---|
| 7,931,864 B2 | 4/2011 | Kloepfer et al. |
| 7,935,079 B2 | 5/2011 | Ludin et al. |
| 7,955,305 B2 | 6/2011 | Moberg et al. |
| 7,981,076 B2 | 7/2011 | Sullivan et al. |
| 2001/0000282 A1 | 4/2001 | Poleshuk et al. |
| 2002/0004015 A1 | 1/2002 | Carlisle et al. |
| 2002/0018720 A1 | 2/2002 | Carlisle et al. |
| 2002/0019714 A1 | 2/2002 | Carlisle et al. |
| 2002/0040208 A1 | 4/2002 | Flaherty et al. |
| 2002/0045265 A1 | 4/2002 | Bergh et al. |
| 2002/0048536 A1 | 4/2002 | Bergh et al. |
| 2002/0055787 A1 | 5/2002 | Lennox et al. |
| 2002/0059959 A1 | 5/2002 | Qatu et al. |
| 2002/0117214 A1 | 8/2002 | Tucker et al. |
| 2002/0120234 A1 | 8/2002 | Kong |
| 2002/0154571 A1 | 10/2002 | Cefai et al. |
| 2003/0014016 A1 | 1/2003 | Purdy |
| 2003/0036725 A1 | 2/2003 | Lavi et al. |
| 2003/0055380 A1 | 3/2003 | Flaherty |
| 2003/0060765 A1 | 3/2003 | Campbell et al. |
| 2003/0093105 A1 | 5/2003 | Huffmaster |
| 2003/0097082 A1 | 5/2003 | Purdy et al. |
| 2003/0130577 A1 | 7/2003 | Purdy et al. |
| 2003/0183289 A1 | 10/2003 | Seuret et al. |
| 2003/0212364 A1 | 11/2003 | Mann et al. |
| 2003/0216683 A1 | 11/2003 | Shekalim |
| 2004/0010207 A1 | 1/2004 | Flaherty et al. |
| 2004/0051368 A1 | 3/2004 | Caputo |
| 2004/0078028 A1 | 4/2004 | Flaherty et al. |
| 2004/0092865 A1 | 5/2004 | Flaherty et al. |
| 2004/0116866 A1 | 6/2004 | Gorman et al. |
| 2004/0116905 A1 | 6/2004 | Pederson et al. |
| 2004/0133220 A1 | 7/2004 | Lashinski et al. |
| 2004/0138744 A1 | 7/2004 | Lashinski et al. |
| 2004/0153146 A1 | 8/2004 | Lashinski et al. |
| 2004/0167478 A1 | 8/2004 | Mooney et al. |
| 2004/0171987 A1 | 9/2004 | Bridle et al. |
| 2004/0193090 A1 | 9/2004 | Lebel et al. |
| 2004/0204673 A1 | 10/2004 | Flaherty |
| 2004/0220551 A1 | 11/2004 | Flaherty et al. |
| 2004/0225252 A1 | 11/2004 | Gillespie et al. |
| 2004/0235446 A1 | 11/2004 | Flaherty et al. |
| 2004/0260233 A1 | 12/2004 | Garibotto et al. |
| 2005/0020980 A1 | 1/2005 | Inoue et al. |
| 2005/0022274 A1 | 1/2005 | Campbell et al. |
| 2005/0038379 A1 | 2/2005 | Beebe et al. |
| 2005/0043710 A1 | 2/2005 | Hadzic et al. |
| 2005/0054994 A1 | 3/2005 | Cioanta et al. |
| 2005/0060030 A1 | 3/2005 | Lashinski et al. |
| 2005/0115622 A1 | 6/2005 | Bennett et al. |
| 2005/0137530 A1 | 6/2005 | Campbell et al. |
| 2005/0137578 A1 | 6/2005 | Heruth et al. |
| 2005/0171512 A1 | 8/2005 | Flaherty |
| 2005/0171513 A1 | 8/2005 | Mann et al. |
| 2005/0171569 A1 | 8/2005 | Girard et al. |
| 2005/0182366 A1 | 8/2005 | Vogt et al. |
| 2005/0211322 A1 | 9/2005 | Lohbeck |
| 2005/0238507 A1 | 10/2005 | DiIanni et al. |
| 2005/0240119 A1 | 10/2005 | Draudt et al. |
| 2005/0245867 A1 | 11/2005 | Olsen et al. |
| 2006/0041229 A1 | 2/2006 | Garibotto et al. |
| 2006/0042695 A1 | 3/2006 | Gonia |
| 2006/0116757 A1 | 6/2006 | Lashinski et al. |
| 2006/0139354 A1 | 6/2006 | Suma |
| 2006/0149214 A1 | 7/2006 | Breiter et al. |
| 2006/0150747 A1 | 7/2006 | Mallett |
| 2006/0178633 A1 | 8/2006 | Garibotto et al. |
| 2006/0189895 A1 | 8/2006 | Neel et al. |
| 2006/0206029 A1 | 9/2006 | Yair |
| 2006/0206054 A1 | 9/2006 | Shekalim et al. |
| 2006/0243804 A1 | 11/2006 | Cristoffersen et al. |
| 2006/0264835 A1 | 11/2006 | Nielson et al. |
| 2006/0282290 A1 | 12/2006 | Flaherty et al. |
| 2007/0000337 A1 | 1/2007 | Gross |
| 2007/0033074 A1 | 2/2007 | Nitzan et al. |
| 2007/0100235 A1 | 5/2007 | Kennedy |
| 2007/0118405 A1 | 5/2007 | Campbell et al. |
| 2007/0123819 A1 | 5/2007 | Mernoe et al. |
| 2007/0124002 A1 | 5/2007 | Estes et al. |
| 2007/0142822 A1 | 6/2007 | Remde |
| 2007/0149926 A1 | 6/2007 | Moberg et al. |
| 2007/0150019 A1 | 6/2007 | Youker et al. |
| 2007/0156092 A1 | 7/2007 | Estes et al. |
| 2007/0161955 A1 | 7/2007 | Bynum et al. |
| 2007/0167905 A1 | 7/2007 | Estes et al. |
| 2007/0167912 A1 | 7/2007 | Causey et al. |
| 2007/0173762 A1 | 7/2007 | Estes et al. |
| 2007/0179444 A1 | 8/2007 | Causey et al. |
| 2007/0201992 A1 | 8/2007 | Mernoe et al. |
| 2007/0203459 A1 | 8/2007 | Mernoe et al. |
| 2007/0219496 A1 | 9/2007 | Kamen et al. |
| 2007/0250007 A1 | 10/2007 | Shekalim et al. |
| 2007/0264130 A1 | 11/2007 | Mallett |
| 2007/0287985 A1 | 12/2007 | Estes et al. |
| 2007/0288176 A1 | 12/2007 | Carlisle et al. |
| 2008/0004601 A1 | 1/2008 | Jennewine et al. |
| 2008/0015510 A1 | 1/2008 | Sandoz et al. |
| 2008/0029173 A1 | 2/2008 | DiPerna |
| 2008/0033357 A1 | 2/2008 | Mann et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0082040 A1 | 4/2008 | Kubler et al. |
| 2008/0092969 A1 | 4/2008 | DiPerna |
| 2008/0097291 A1 | 4/2008 | Hanson et al. |
| 2008/0097375 A1 | 4/2008 | Bikovsky |
| 2008/0114228 A1 | 5/2008 | McCloskey et al. |
| 2008/0116647 A1 | 5/2008 | Anderson et al. |
| 2008/0147004 A1 | 6/2008 | Mann et al. |
| 2008/0147050 A1 | 6/2008 | Mann et al. |
| 2008/0160492 A1 | 7/2008 | Campbell et al. |
| 2008/0196762 A1 | 8/2008 | Mallett et al. |
| 2008/0197801 A1 | 8/2008 | Manor et al. |
| 2008/0281276 A1 | 11/2008 | Shekalim |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0304365 A1 | 12/2008 | Jarvis et al. |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0088701 A1 | 4/2009 | Larsen |
| 2009/0131863 A1 | 5/2009 | Carlisle et al. |
| 2009/0143732 A1 | 6/2009 | O'Connor et al. |
| 2009/0156990 A1 | 6/2009 | Wenger et al. |
| 2009/0191067 A1 | 7/2009 | DiPerna |
| 2009/0217982 A1 | 9/2009 | DiPerna |
| 2009/0229374 A1 | 9/2009 | Carlisle et al. |
| 2009/0234594 A1 | 9/2009 | Carlisle et al. |
| 2009/0247982 A1 | 10/2009 | Krulevitch et al. |
| 2009/0272928 A1 | 11/2009 | Alvarez et al. |
| 2009/0275887 A1 | 11/2009 | Estes et al. |
| 2009/0287180 A1 | 11/2009 | DiPerna |
| 2009/0292245 A1 | 11/2009 | Basso et al. |
| 2009/0321675 A1 | 12/2009 | Alvarez et al. |
| 2010/0008795 A1 | 1/2010 | DiPerna |
| 2010/0032041 A1 | 2/2010 | DiPerna |
| 2010/0036327 A1 | 2/2010 | DiPerna |
| 2010/0038572 A1 | 2/2010 | Alvarez et al. |
| 2010/0043738 A1 | 2/2010 | Grandvallet et al. |
| 2010/0049164 A1 | 2/2010 | Estes et al. |
| 2010/0063765 A1 | 3/2010 | Carlisle et al. |
| 2010/0065579 A1 | 3/2010 | DiPerna |
| 2010/0069890 A1 | 3/2010 | Graskov et al. |
| 2010/0071446 A1 | 3/2010 | Brown |
| 2010/0081993 A1 | 4/2010 | O'Connor |
| 2010/0094251 A1 | 4/2010 | Estes et al. |
| 2010/0096019 A1 | 4/2010 | DiPerna |
| 2010/0106100 A1 | 4/2010 | Petersen |
| 2010/0121306 A1 | 5/2010 | Yodfat et al. |
| 2010/0137833 A1 | 6/2010 | Glynn |
| 2010/0145303 A1 | 6/2010 | Yodfat et al. |

| | | | |
|---|---|---|---|
| 2010/0165795 | A1 | 7/2010 | Elder et al. |
| 2010/0168711 | A1 | 7/2010 | Bazargan et al. |
| 2010/0198183 | A1 | 8/2010 | Lanigan et al. |
| 2010/0218586 | A1 | 9/2010 | Rosinko |
| 2010/0228186 | A1 | 9/2010 | Estes et al. |
| 2010/0249566 | A1 | 9/2010 | Suess et al. |
| 2011/0009813 | A1 | 1/2011 | Rankers |
| 2011/0033833 | A1 | 2/2011 | Blomquist |
| 2011/0050428 | A1 | 3/2011 | Istoc |
| 2011/0108158 | A1 | 5/2011 | Huwiler et al. |
| 2011/0111794 | A1 | 5/2011 | Bochenko |
| 2011/0124996 | A1 | 5/2011 | Reinke et al. |
| 2011/0152769 | A1 | 6/2011 | Ramey et al. |

FOREIGN PATENT DOCUMENTS

| | | |
|---|---|---|
| CN | 2668847 Y | 1/2005 |
| EP | 0055836 | 7/1982 |
| EP | 0376894 | 12/1988 |
| EP | 0385916 | 5/1990 |
| EP | 0494042 | 7/1992 |
| EP | 0560571 | 9/1993 |
| EP | 1217275 | 12/2000 |
| EP | 1938750 | 7/2008 |
| JP | 06-016165 | 4/1994 |
| JP | 08-312820 | 11/1996 |
| JP | 2952037 | 9/1999 |
| JP | 2002-143293 | 5/2002 |
| JP | 2006-009944 | 1/2006 |
| JP | 2006-101985 | 4/2009 |
| JP | 2009-148591 | 7/2009 |
| JP | 2010-075736 | 4/2010 |
| KR | 10-2001-0080519 | 8/2001 |
| WO | WO 90/13795 | 11/1990 |
| WO | WO 91/00753 | 1/1991 |
| WO | WO 94/26329 | 11/1994 |
| WO | WO 95/32013 | 11/1995 |
| WO | WO 96/08049 | 3/1996 |
| WO | WO 96/25189 | 8/1996 |
| WO | WO 98/19627 | 5/1998 |
| WO | WO 98/57683 | 12/1998 |
| WO | WO 99/01088 | 1/1999 |
| WO | WO 00/10628 | 3/2000 |
| WO | WO 00/35527 | 6/2000 |
| WO | WO 00/40346 | 7/2000 |
| WO | WO 00/72900 | 12/2000 |
| WO | WO 01/30422 | 5/2001 |
| WO | WO 02/028532 | 10/2001 |
| WO | WO 02/11791 | 2/2002 |
| WO | WO 02/26102 | 4/2002 |
| WO | WO 03/081052 | 3/2003 |
| WO | WO 03/102737 | 6/2003 |
| WO | WO 2004/009152 | 1/2004 |
| WO | WO 2004/088148 | 3/2004 |
| WO | WO 2004/036150 | 4/2004 |
| WO | WO 2004/047677 | 6/2004 |
| WO | WO 2004/060464 | 7/2004 |
| WO | WO 2004/056412 | 12/2004 |
| WO | WO 2005/082450 | 2/2005 |
| WO | WO 2005/018507 | 3/2005 |
| WO | WO 2008/028509 | 9/2006 |
| WO | WO 2008/037270 | 9/2006 |
| WO | WO 2008/037271 | 9/2006 |
| WO | WO 2008/037272 | 9/2006 |
| WO | WO 2008/037273 | 9/2006 |
| WO | WO 2006/108219 | 10/2006 |
| WO | WO 2008/043381 | 10/2006 |
| WO | WO 2007/038059 | 4/2007 |
| WO | WO 2007/038060 | 4/2007 |
| WO | WO 2007/038091 | 4/2007 |
| WO | WO 2007/056504 | 5/2007 |
| WO | WO 2007/056592 | 5/2007 |
| WO | WO 2007/089983 | 8/2007 |
| WO | WO 2007/098265 | 8/2007 |
| WO | WO 2007/098287 | 8/2007 |
| WO | WO 2007/106232 | 9/2007 |
| WO | WO 2007/119149 | 10/2007 |
| WO | WO 2008/050126 | 10/2007 |
| WO | WO 2008/050128 | 10/2007 |
| WO | WO 2008/071220 | 3/2008 |
| WO | WO 2008/144693 | 5/2008 |
| WO | WO 2008/144695 | 5/2008 |
| WO | WO 2008/144697 | 5/2008 |
| WO | WO 2008/144698 | 5/2008 |
| WO | WO 2009/032402 | 7/2008 |
| WO | WO 2009/035759 | 7/2008 |
| WO | WO 2009/035761 | 7/2008 |
| WO | WO 2009/035762 | 7/2008 |
| WO | WO 2008/103175 | 8/2008 |
| WO | WO 2008/121599 | 10/2008 |
| WO | WO 2009/032399 | 10/2008 |
| WO | WO 2009/032400 | 10/2008 |
| WO | WO 2009/035753 | 10/2008 |
| WO | WO 2009/106233 | 2/2009 |
| WO | WO 2009/094590 | 7/2009 |
| WO | WO 2009/108639 | 9/2009 |
| WO | WO 2009/143188 | 11/2009 |
| WO | WO 2010/016977 | 2/2010 |
| WO | WO 2010/016978 | 2/2010 |
| WO | WO 2010/033634 | 3/2010 |
| WO | WO 2010/033878 | 3/2010 |
| WO | WO 2010/038031 | 4/2010 |
| WO | WO 2010/096449 | 8/2010 |
| WO | WO 2010/099490 | 9/2010 |
| WO | WO 2011/017667 | 2/2011 |

OTHER PUBLICATIONS

International Search Report and Written Opinion mailed on Sep. 10, 2004 in International Application: PCT/US2003/022703 filed on Jul. 15, 2003 and published as: WO 04/009152 on Jan. 29, 2004.
International Search Report and Written Opinion mailed on: Jul. 23, 2007 in International Application: PCT/2007/060633 filed on: Jan. 17, 2007 and published as: WO 07/089983 on: Aug. 9, 2007.
International Preliminary Report on Patentability mailed on: Jul. 29, 2008 in International Application: PCT/2007/060633 filed on: Jan. 17, 2007 and published as: WO 07/089983 on: Aug. 9, 2007.
International Search Report and Written Opinion mailed on: May 29, 2009 in International Application: PCT/US2009/035022 filed on: Jan. 23, 2009 and published as: WO 09/108639 on: Sep. 3, 2009.
International Preliminary Report on Patentability mailed on: Sep. 10, 2010 in International Application: PCT/US2009/035022 filed on: Jan. 23, 2009 and published as: WO 09/108639 on: Sep. 3, 2009.
International Preliminary Report on Patentability mailed on: Oct. 6, 2009 in International Application: PCT/US2008/058044 filed on: Mar. 24, 2008 and published as: WO 08/121599 on: Oct. 9, 2009
Written Opinion of the International Searching Authority of Aug. 11, 2008 in International Application: PCT/US2008/058044 filed on: Mar. 24, 2008 and published as: WO 08/121599 on: Oct. 9, 2009.
International Search Report and Written Opinion mailed on: Feb. 17, 2011 in International Application: PCT/US2009/049110 filed on: Jun. 29, 2009 and published as: WO 10/016977 on: Feb. 11, 2010.
International Search Report and Written Opinion mailed on: Jan. 27, 2010 in International Application: PCT/US2009/049110 filed on: Jun. 29, 2009 and published as: WO 10/016977 on: Feb. 11, 2010.
International Search Report and Written Opinion mailed on: Feb. 17, 2011 in International Application: PCT/2009/049166 filed on: Jun. 29, 2009 and published as: WO 10/016978 on: Feb. 11, 2010.
International Search Report and Written Opinion mailed on: Feb. 4, 2010 in International Application: PCT/2009/049166 filed on: Jun. 29, 2009 and published as: WO 10/016978 on: Feb. 11, 2010.
International Preliminary Report on Patentability mailed on Aug. 5, 2010 in International Application: PCT/US2009/031906 filed on Jan. 23, 2009 and published as: WO 09/094590 on Jul. 30, 2009.
International Search Report and Written Opinion mailed on Jul. 28, 2009 in International Application: PCT/US2009/031906 filed on Jan. 23, 2009 and published as: WO 09/094590 on Jul. 30, 2009.
International Search Report and Written Opinion mailed on: Apr. 27, 2011 in International Application: PCT/US2010/044789 filed on Aug. 6, 2011 and published as: WOo 11/017667 on Feb. 10, 2011.
A1868. International Search Report and Written Opinion mailed on: Jan. 4, 2010 in International Application: PCT/US2009/044569 filed on: May 19, 2009 and published as: WO 09/143188 on: Nov. 26, 2009.

International Preliminary Report on Patentability mailed: Dec. 2, 2010, in International Patent Application No. PCT/US2009/044569 filed on: May 19, 2009 and published as Wo 2009/143188 on: Nov. 26, 2009.
International Preliminary Report on Patentability mailed on Mar. 31, 2011 in International Application: PCT/2009/057208 filed on: Sep. 16, 2009 and published as: WO 10/033634 on: Mar. 25, 2010.
International Search Report and Written Opinion mailed on Apr. 1, 2010 in International Application: PCT/2009/057208 filed on: Sep. 16, 2009 and published as: WO 10/033634 on: Mar. 25, 2010.
International Search Report and Written Opinion mailed on: Sep. 30, 2010 in International Application: PCT/2010/025663 filed on: Feb. 26, 2010 and published as: WO 10/099490 on: Sep. 2, 2010.
International Preliminary Report on Patentability mailed on Mar. 31, 2011 in International Application: PCT/2009/57591 filed on: Sep. 18, 2009 and published as: WO 10/033878 on: Mar. 25, 2010.
International Search Report and Written Opinion mailed on Apr. 12, 2010 in International Application: PCT/2009/57591 filed on: Sep. 18, 2009 and published as: WO 10/033878 on: Mar. 25, 2010.
International Search Report and Written Opinion mailed on Apr. 11, 2011 in International Application: PCT/2010/034789 filed on: Jul. 29, 2010 and publishedas: WO 11/014704 on: Feb. 3, 2011.
Office Action mailed on: Dec. 15, 2005 in U.S. Appl. No. 10/200,109, filed May 4, 2007 and issued as: 7,008,403 on: Mar. 7, 2007.
Office Action mailed on: Apr. 14, 2005 in U.S. Appl. No. 10/200,109, filed May 4, 2007 and issued as: 7,008,403 on: Mar. 7, 2007.
Office Action mailed on: Oct. 4, 2004 in U.S. Appl. No. 10/200,109, filed May 4, 2007 and issued as: 7,008,403 on: Mar. 7, 2007.
Office Action mailed on: Jun. 23, 2004 in U.S. Appl. No. 10/200,109, filed May 4, 2007 and issued as: 7,008,403 on: Mar. 7, 2007.
A1880. Office Action mailed on: May 29, 2009 in U.S. Appl. No. 11/744,819, filed May 4, 2007 and published as: US-2007-0264130 on Nov. 15, 2007.
Office Action mailed on: Aug. 5, 2009 in U.S. Appl. No. 11/744,819, filed May 4, 2007 and published as: US-2007-0264130 on Nov. 15, 2007.
Office Action mailed on: Mar. 9, 2010 in U.S. Appl. No. 11/744,819, filed May 4, 2007 and published as: US-2007-0264130 on Nov. 15, 2007.
Office Action mailed on: Jan. 8, 2008 in U.S. Appl. No. 11/342,015, filed Jan. 27, 2006 and published as: US-2006-0150747 on: Jul. 13, 2006 and issued as: 7,341,581 on: Mar. 11,2008.
Office Action mailed on: Jun. 8, 2007 in U.S. Appl. No. 11/343,817, filed Jan. 31, 2006 and published as: US-2006-0150748 on: Jul. 13, 2006 and issued as: 7,374,556 on: May 20, 2008.
Office Action mailed on: Mar. 11, 2008 in U.S. Appl. No. 11/343,817, filed Jan. 31, 2006 and published as: US-2006-0150748 on: Jul. 13, 2006 and issued as: 7,374,556 on: May 20, 2008.
Office Action mailed on: Mar. 3, 2011 in U.S. Appl. No. 12/020,498, filed Jan. 25, 2008 and published as: US-2009-0191067 on: Jul. 30, 2009.
Office Action mailed on: Jul. 18, 2011 in U.S. Appl. No. 12/108,462, filed Apr. 23, 2008 and published as: US-2008-0196762 on: Aug. 21, 2008.
Office Action mailed on: Mar. 21, 2011 in U.S. Appl. No. 12/108,462, filed Apr. 23, 2008 and published as: US-2008-0196762 on: Aug. 21, 2008.
Office Action mailed on: Oct. 6, 2010 in U.S. Appl. No. 12/108,462, filed Apr. 23, 2008 and published as: US-2008-0196762 on: Aug. 21, 2008.
Office Action mailed on Dec. 29, 2009 in U.S. Appl. No. 12/486,795, filed May 19, 2009 and published as US 2009/0287180 on Nov. 19, 2009.
Office Action mailed on May 27, 2010 in U.S. Appl. No. 12/486,795, filed May 19, 2009 and published as US 2009/0287180 on Nov. 19, 2009.

* cited by examiner

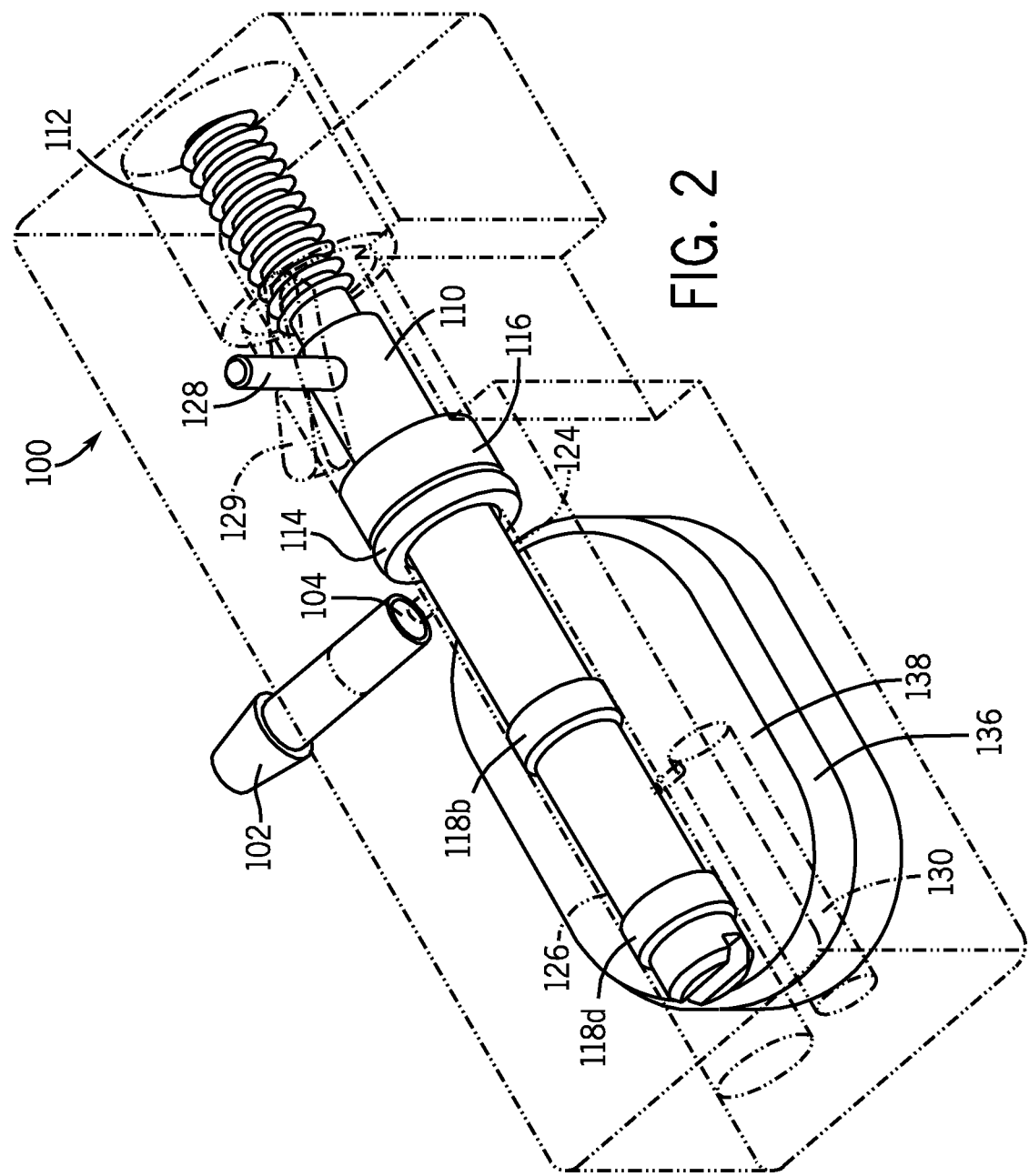

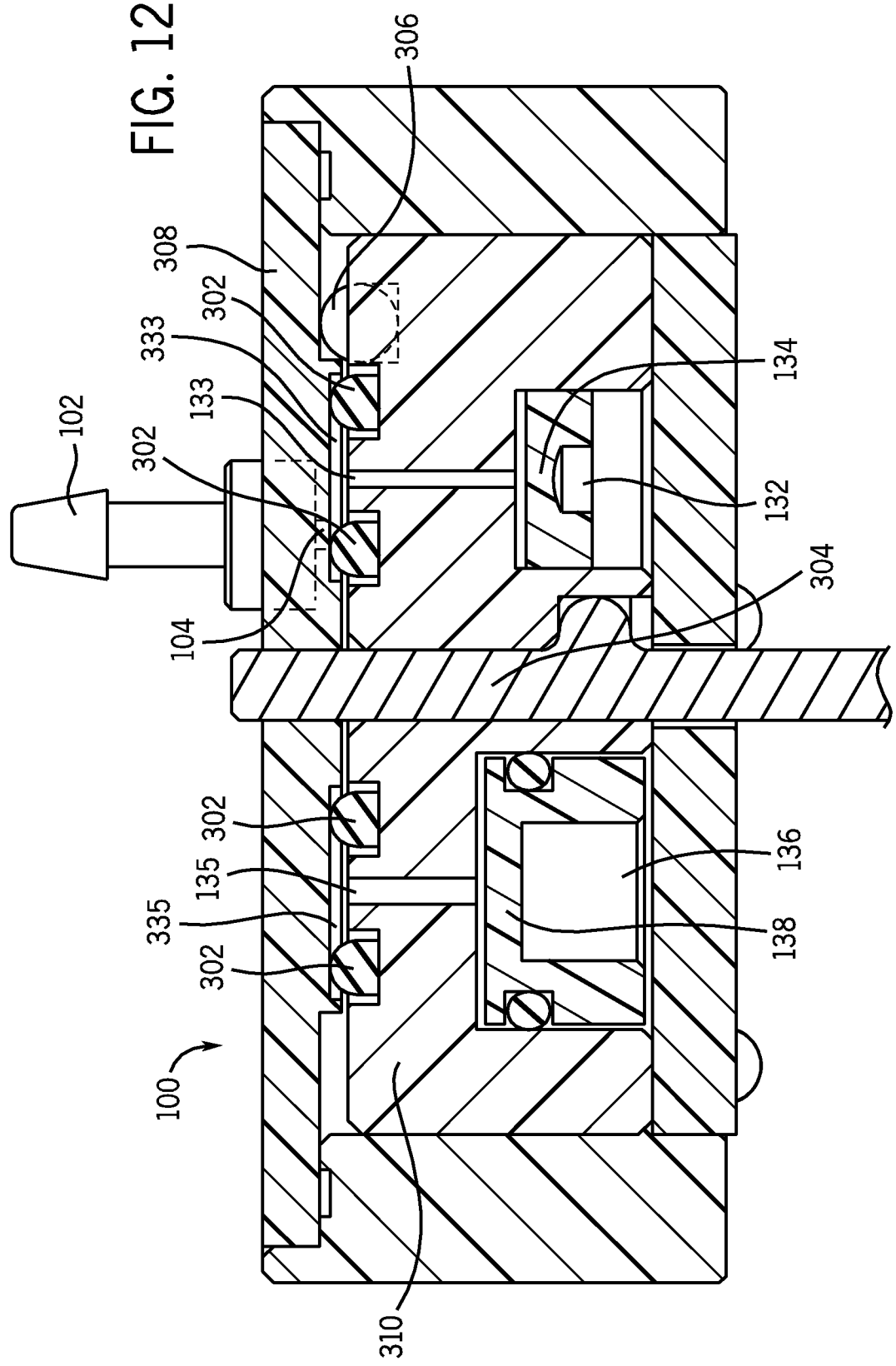

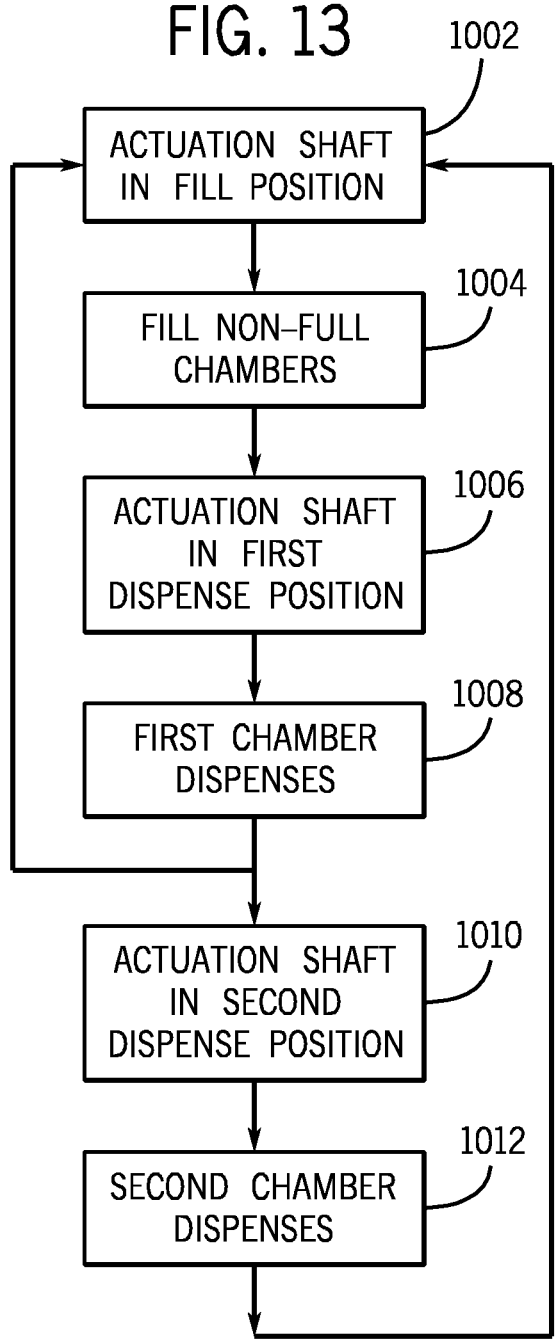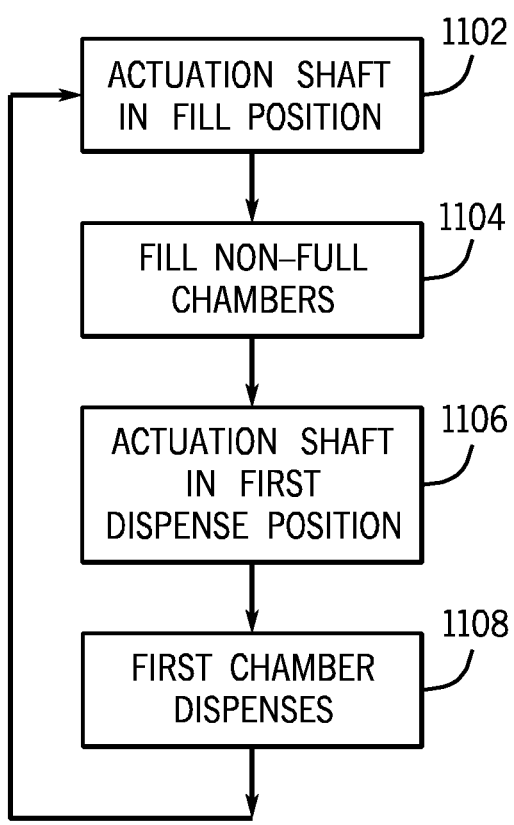

SLIDEABLE FLOW METERING DEVICES AND RELATED METHODS

RELATED APPLICATIONS

This application claims the Paris Convention priority and incorporates by reference U.S. Provisional Patent Application Ser. No. 61/097,492, filed Sep. 16, 2008, and entitled "Flow Regulating Stopcocks and Related Methods."

BACKGROUND

This disclosure relates to devices and methods for the regulation of the flow of flow materials, as well as features to prevent undesired flow.

SUMMARY

A novel enhanced flow metering device is disclosed, as well as related methods, that safely controls and meters the flow of a flow material. A pump fills a flow metering device with a flow material, which then dispenses the flow material to a target. The flow material charges the device by moving into at least one chamber when an actuation shaft is in a charging position. Flow materials are dispensed from the chambers of the flow metering device when the actuation shaft is moved into at least one dispensing positions.

According to a feature of the present disclosure, a device is disclosed comprising an actuation shaft disposed in a cavity of the device having at least one movable seal defining at least one flow space; an input port; an outlet port; and at least one chamber having a compressible member for holding a flow material. Only one of the inlet port and outlet port are in fluid communication with each chamber at a time.

According to a feature of the present disclosure, a method is disclosed comprising providing a device having an actuation shaft disposed in a cavity of the device having at least one movable seal defining at least one flow space; an input port; an outlet port; and at least one chamber having a compressible member. Only one of the inlet port and outlet port are in fluid communication with each chamber at a time.

According to a feature of the present disclosure, a method is disclosed comprising positioning an actuation shaft of a flow metering device into a first position whereby at least one chamber, a proximal flow space, and an input conduit are in fluid communication; and positioning the actuation shaft into a second position whereby the chamber is in fluid communication with a distal flow space and an output conduit. The proximal flow space and the input conduit are never in fluid communication with the distal flow space and the output conduit.

DRAWINGS

The above-mentioned features and objects of the present disclosure will become more apparent with reference to the following description taken in conjunction with the accompanying drawings wherein like reference numerals denote like elements and in which:

FIG. 2 is a perspective view of an embodiment of the flow metering device of the present disclosure having one chamber;

FIG. 12 is an elevation view in section of an embodiment of the flow metering device of the present disclosure having two chambers and rotating about an axis;

FIG. 13 is a flow diagram of embodiments of a method for dispensing a flow material through the stopcock devices of the present disclosure; and FIG. 14 is a flow diagram of embodiments of a method for dispensing a flow material through the stopcock devices of the present disclosure.

DETAILED DESCRIPTION

Figure 1A:
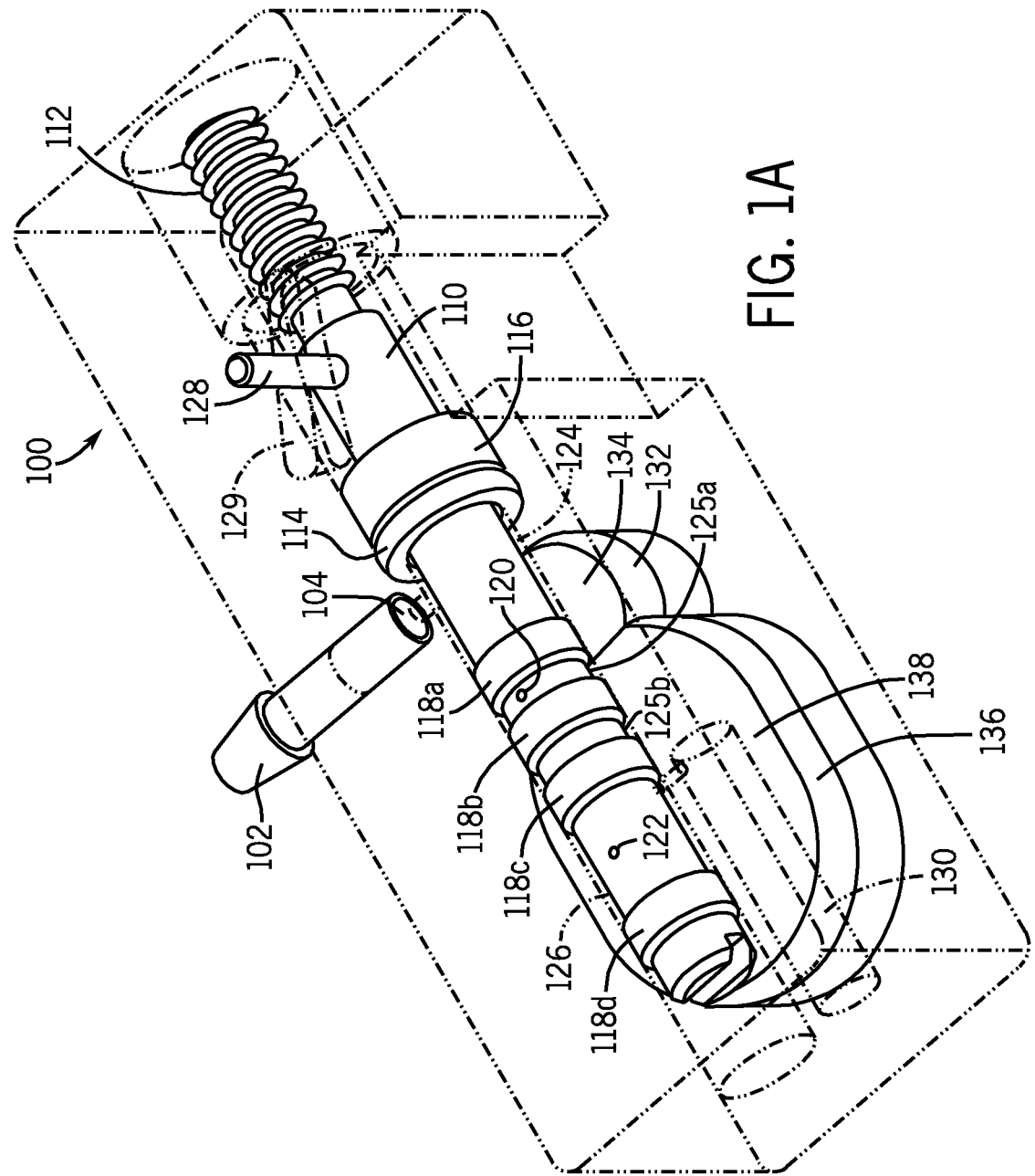
FIG. 1A is a perspective view of an embodiment of the flow metering device of the present disclosure having two chambers actuated by a threaded device.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

As used herein, the term "real time" shall be understood to mean the instantaneous moment of an event or condition, or the instantaneous moment of an event or condition plus short period of elapsed time used to make relevant measurements, optional computations, etc., and communicate the measurement, computation, or etc., wherein the state of an event or condition being measured is substantially the same as that of the instantaneous moment irrespective of the elapsed time interval. Used in this context "substantially the same" shall be understood to mean that the data for the event or condition remains useful for the purpose for which it is being gathered after the elapsed time period.

As used herein, the term "compressible member" shall be understood to mean devices that cause a gas or fluid to be compressed when a gas or fluid is placed into a chamber where the compressible member is disposed. Examples of compressible members include, for example, closed cell foams, elastomeric membranes and diaphragms, pistons, and secondary chambers and devices charged with a fixed volume of gas or fluid, wherein when a gas or fluid is placed into the chamber in which the compressible member is disposed, the gas or fluid in the compressible member compresses.

The inventor discovered a device and method for preventing inadvertent flow of flow materials from a pump to a target. The device comprises a flow metering device having at least one chamber built in that is charged with aliquots of flow material. The flow metering device comprises an actuation shaft that is moved to a charging position that is used for charging (filling) the chamber(s) of flow metering device into at least a first dispense position (or a plurality of dispense positions) that is configured for dispensing the aliquots of charged flow material stored in one or more of the chambers.

According to embodiments, at least one pressure sensor is optionally disposed to measure, in real time, the pressure in the flow metering device to derive the volume of flow material in the at least one chamber or dispensed from the flow metering device. Because flow volumes and the elapsed time are also known, the flow rate of the dispensed flow material may be calculated, according to embodiments. Temperature sensors may similarly be disposed to improve the accuracy of the calculations used to measure the flow volume or rate. Where a pressure sensor is used, a computer that receives the pressure sensor data performs the relevant calculations to measure volumes or flow rates. The computer comprises at least a timing device for measuring elapsed time, which may comprise a clock or a timer, for example; devices to receive input from the pressure sensors, temperature sensors, and users; and a processor for performing the calculations disclosed herein.

According to embodiments, and as well known and understood by artisans, other methods for determination of the volume of are expressly contemplated in the instant application. For example, acoustic sensors, including a loud speaker and one or more microphones may be used to accurately determine the volume of first chamber 136 or second chamber 132, thereby allowing for calculation of the volume of flow material in the chambers. Acoustic volume determination technology is disclosed in U.S. Pat. Nos. 5,575,310 and 5,755,683, which are incorporated by reference; and U.S. Provisional Application Ser. No. 60/789,243, which is incorporated by reference. U.S. Pat Application Publication No. 2007/0219496, which is incorporated by reference, discloses still further methods for the determination of the volume of first chamber 136 or second chamber 132, including via optical, capacitive, deflection measure methods (detecting deflection of a membrane as pressure changes), thermal time of flight methods, or other methods for measuring the volume of a chamber.

According to embodiments illustrated in FIG. 1A, flow metering device 100 is shown. Flow metering device 100 comprises cavity 109 in which actuation shaft 110 is disposed. Actuation shaft 110 has a proximal end terminating with actuation device 112 and a distal end. Actuation shaft 110 further comprises optional actuation guide 128 and at least one movable seal 118. According to some embodiments, actuation shaft also comprises at least one shaft channel 121 being defined at the ends by at least one proximal shaft opening 120 and at least one distal shaft opening 122. Flow metering device 100 also comprises at least first chamber 136 having first compressible member 138. According to embodiments, flow metering device 100 also comprises additional chambers, for example second chamber 132 having second compressible member 134, as illustrated in FIG. 1A.

According to embodiments, FIG. 1A illustrates a two-chamber version of flow metering device 100, whereby two chambers of varying size are charged with a flow material and one or both chambers are used to discharge flow material to a target. According to the detail shown in FIG. 1A, flow metering device 100 generally comprises a housing holding first chamber 136, second chamber 132, and actuation shaft 110.

Flow material is charged into first chamber 136 and second chamber 132 through input conduit 104, which is a conduit through input device 102 terminating at proximal flow space 124 for moving flow materials from a flow material source to first chamber 136 or second chamber 132. According to embodiments, input device 102 is a connector or valve designed to be connected with tubing, conduit, piping, or other devices used to transport flow materials, such as gas or fluid.

Flow material is discharged from flow metering device 100 through output conduit 130. Output conduit 130 is a conduit formed in flow metering device 100 that allows flow material to move from first chamber 136 or second chamber 132 to a target. Output conduit 130, according to embodiments, may terminate in a connector, for example a luer connector or other industry standard connector, that connects to devices for delivery to the target. For example, if flow metering device 100 is delivering a pharmaceutical, the connector might be a luer device connected to a length of tubing ending in a hypodermic needle for injection of the pharmaceutical.

Actuation shaft 110 controls the charge and discharge of first chamber 136 and second chamber 132, depending of the position of actuation shaft 110. According to embodiments, actuation shaft 110 disposed in flow metering device cavity 109. Actuation shaft 110 terminates on the proximal end with actuation device 112. Actuation device 112 articulates with an actuator that effects movement of actuation shaft 110.

For example, actuation device 112 is a series of screw-like threads that articulate with mated screw threads in a motor. Depending on the direction the motor rotates the mated screw threads, actuation shaft 110 is moved towards the distal end or towards the proximal end of flow metering device 100.

Figure 1B:
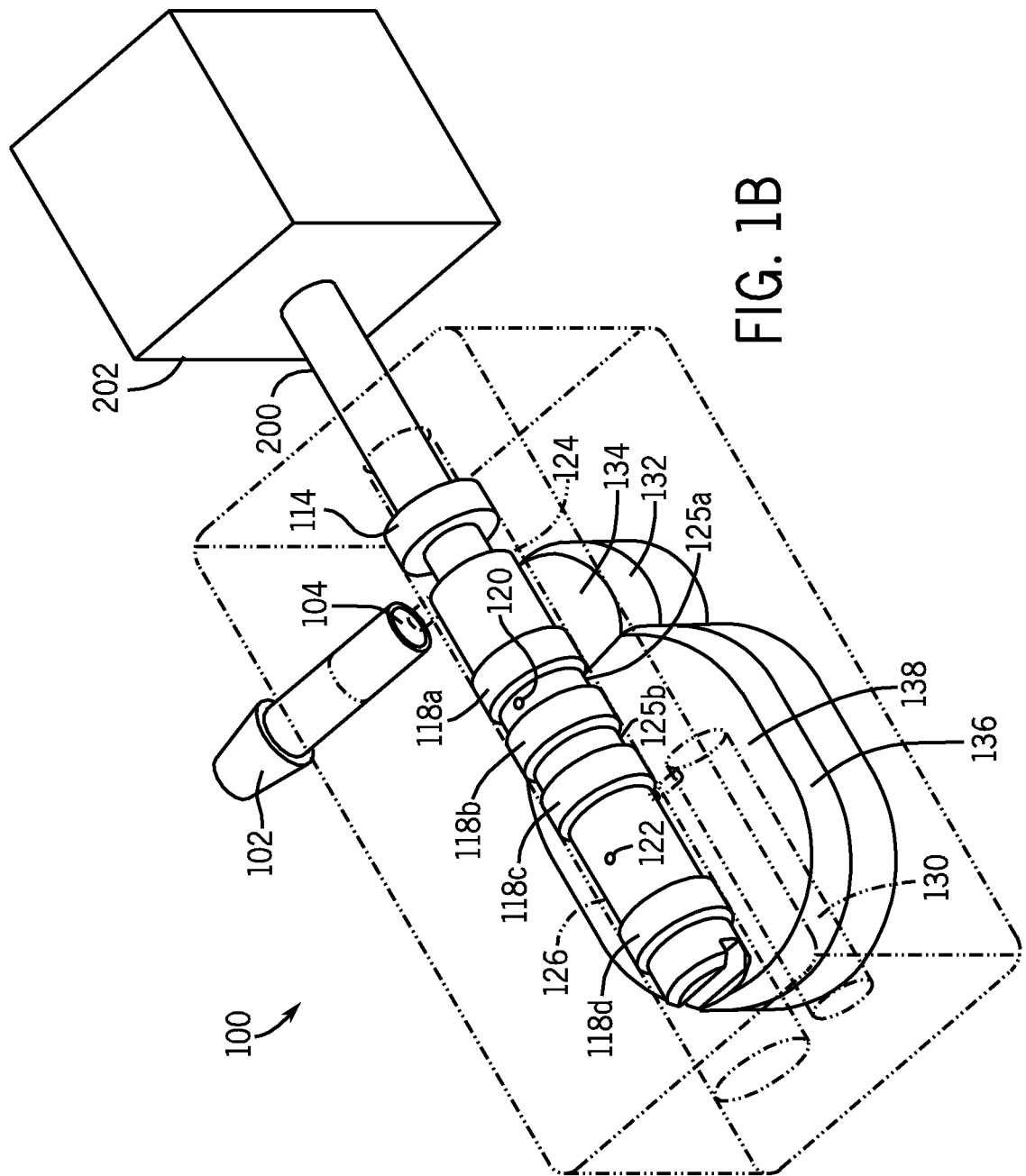
FIG. 1B is a perspective view of an embodiment of the flow metering device of the present disclosure having two chambers actuated by a wire.
Figure 1C:
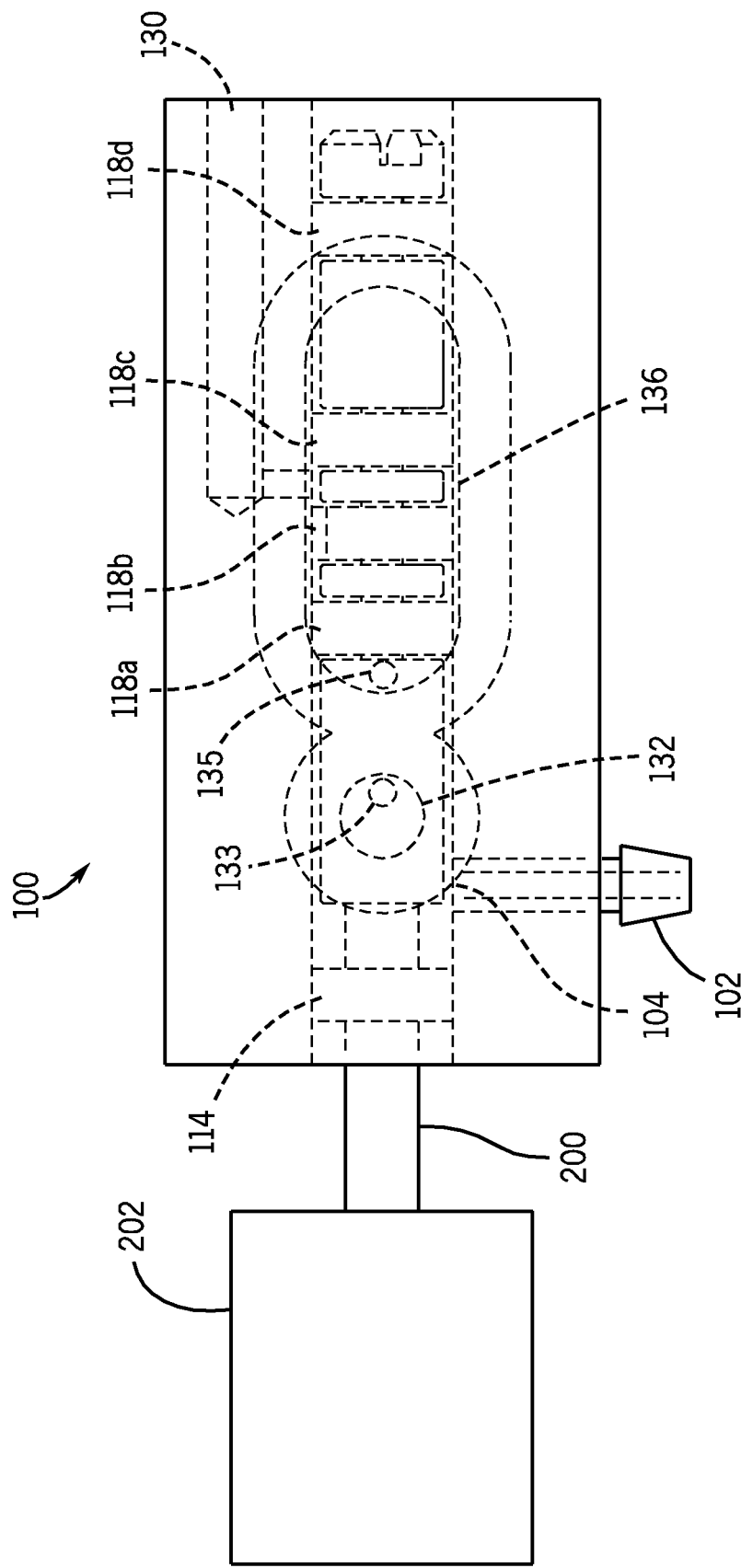
FIG. 1C shows an embodiment of the flow metering device of the present disclosure.
Figure 3:
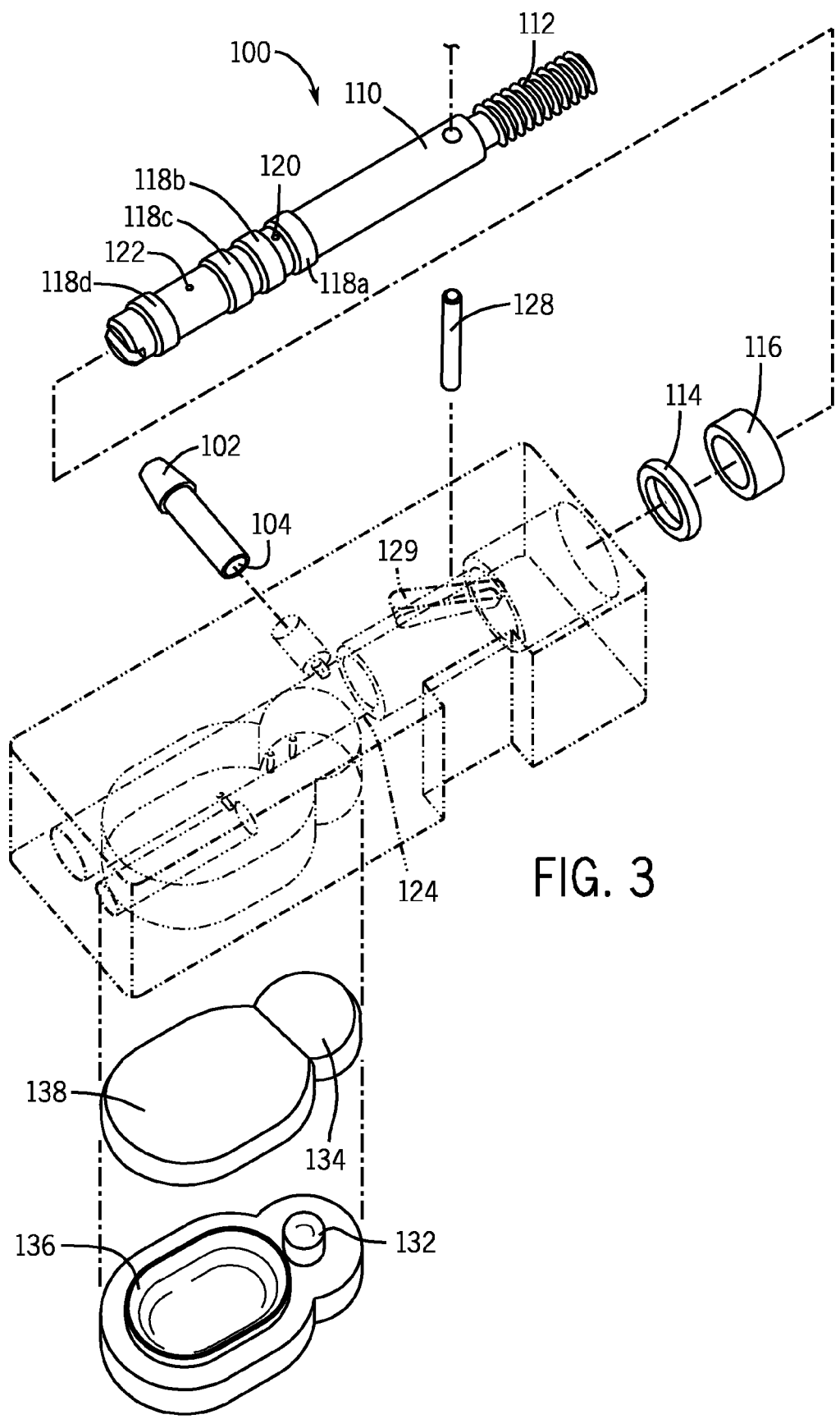
FIG. 3 is an exploded view of an embodiment of the flow metering device of the present disclosure having two chambers.
Figure 4:
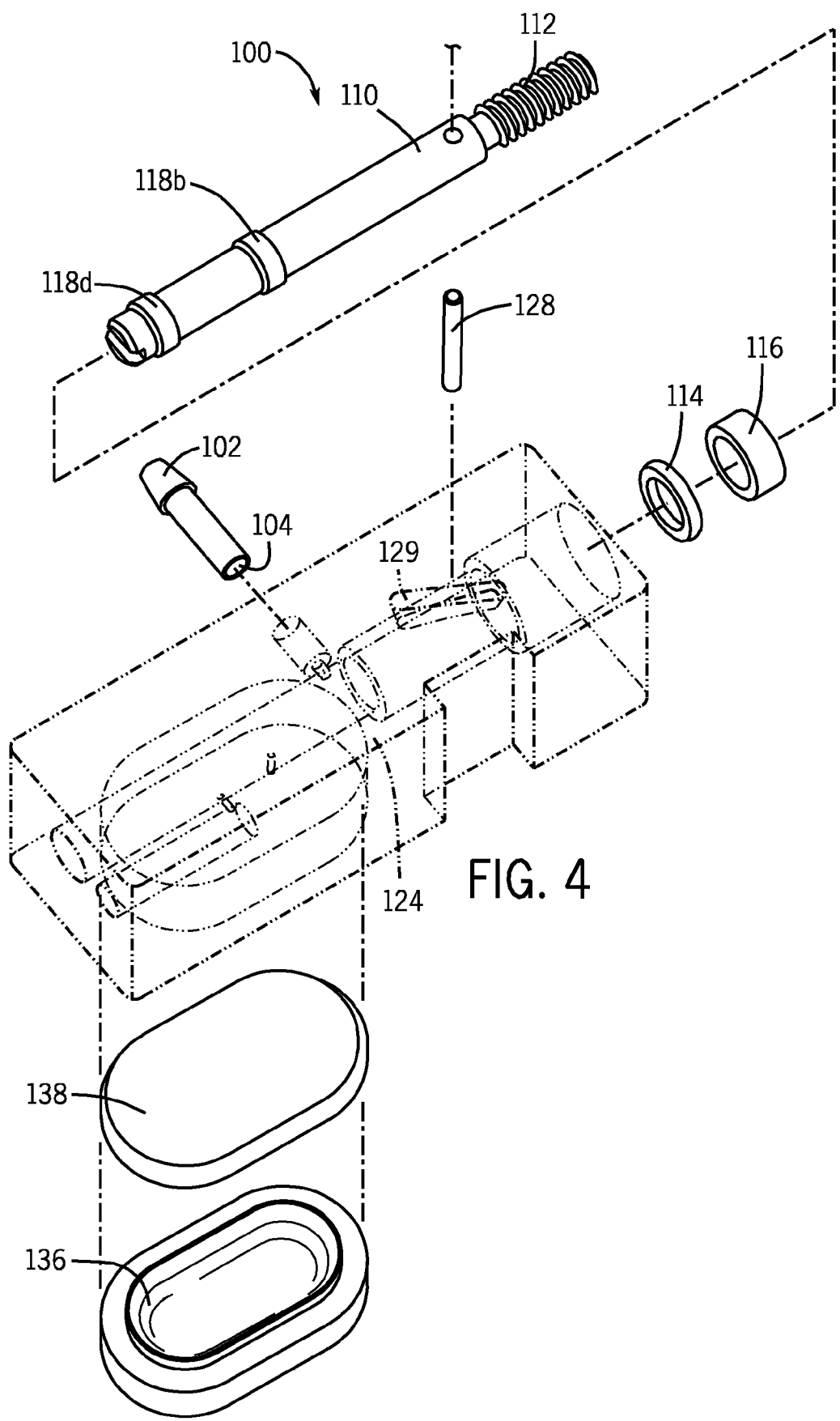
FIG. 4 is an exploded view of an embodiment of the flow metering device of the present disclosure having one chamber.

According to embodiments, actuation device 200 comprises a Nitinol or other shape memory or non-shape memory alloy wire actuator connected to an actuator 202, as shown in FIG. 1B. Similarly, other rigid or semi-rigid materials, such as plastics may by used as the wire actuator. According to these embodiments, the wire moves is pulled and pushed to effect movement of actuation shaft 110. Actuation device 112, irrespective of the mechanical design, effects movement of actuation shaft 110 both proximally and distally along flow metering device cavity 109, as desired.

According to embodiments, actuation shaft 110 moves along its long axis. According to embodiments, rotational movement is also contemplated around the long axis of actuation shaft 110. For example and as illustrated in FIG. 1A, actuation guide 128 is disposed in actuation rotation channel 129. As actuation shaft 110 moves proximal or distal, actuation guide 128 is forced by the walls of actuation rotation channel 129 to shift position in perpendicular to the long axis of actuation shaft 110, thereby causing rotation of actuation shaft 110 around the long axis of actuation shaft 110. Rotating actuation shaft 110 causes movement of actuation shaft 110 to rotate with less friction in along the long axis of actuation shaft 110.

Movable seals 118a-d sealably prevent movement of flow materials around them. Movable seals 118a-d are disposed around actuation shaft 110 and move with actuation shaft 110. Articulation of movable seals 118a-d with actuation shaft 110 the walls of flow metering device cavity 109 forms at least one sealed space. Thus, flow materials cannot pass around movable seals 118a-d. Movable seals may be O-rings, quad-rings, or other similar devices that form sealed barriers to the flow of flow material. According to embodiments, movable seals 118a-d (shown in FIG. 5) are disposed along the length of actuation shaft 110.

Figure 5:
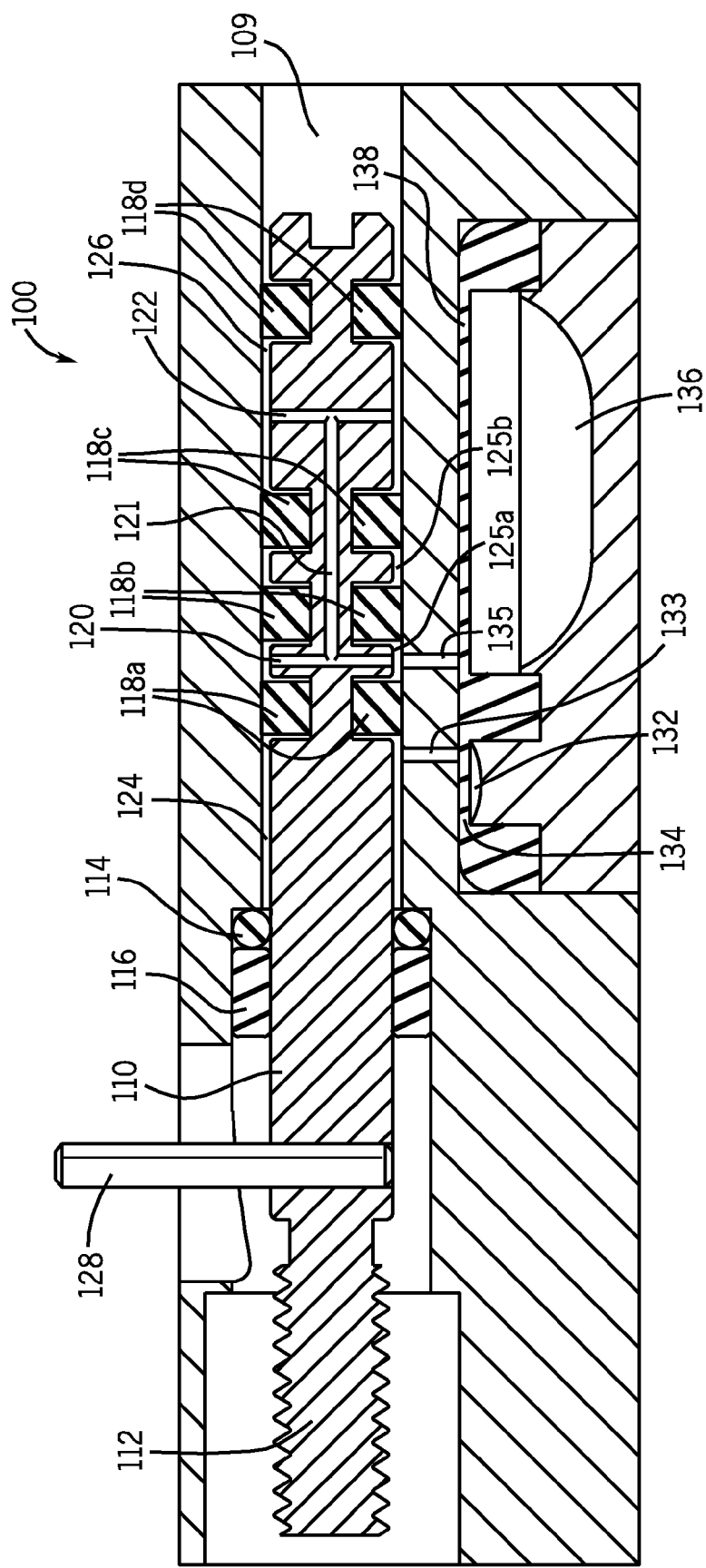
FIG. 5 is a cross-sectional side view of an embodiment of the flow metering device of the present disclosure having two chambers.

An additional seal, fixed seal 114, is disposed towards the proximal end of actuation shaft 110. Fixed seal 114 does not move with actuation shaft 110. It is held in place with friction and seal retainer 116. As illustrated in FIG. 5 and according to embodiments, fixed seal 114 articulates with flow metering device cavity 109 where flow metering device cavity 109 is flanged to accommodate fixed seal 114 and seal retainer 116.

According to embodiments, movable seals 118a-d and fixed seal 114 form a plurality of flow spaces: proximal flow space 124, output flow space 125a, sealed flow space 125b, and distal flow space 126. Each flow space is sealably defined by the walls of flow metering device cavity 109, movable seals 118a-d (or in the case of proximal flow space 124 by movable seal 118a and fixed seal 114), and by the outer surface of actuation shaft 110. Each space is configured to accommodate the flow of flow material.

Devices that have greater than one chamber utilize the multiple movable seals 118a-d to selectively allow flow to and from desired chambers. According to embodiments, shaft channel 121 forms a channel in actuation shaft allowing flow of material flow. The endpoints of shaft channel 121 are proximal shaft opening 120 and distal shaft opening 122. According to embodiments, multiple shaft channels 121 are contemplated, as well as embodiments having a single shaft channel 121. As illustrated in FIG. 5, there may exist multiple distal shaft openings 122, as well as multiple proximal shaft openings 120 to facilitate the desired flow rate through shaft channel 121. Artisans will recognize the considerations that go into deciding the number of openings to use for each shaft channel 121.

As illustrated, shaft channels are used to bypass movable seals 118, thereby defining flow paths. As shown in FIG. 5, shaft channel 121 bypasses movable seals 118b-c and thereby effects flow from one flow space to another flow space. Shaft channel 121 opens into output flow space 125a and distal flow space 126, bypassing sealed flow space 125b. Thus, sealed flow space 125b may be positioned over the conduits leading into the chambers to prevent flow in or out of the chamber over which sealed flow space 125b is positioned, as described in more detail below.

Depending on where shaft channel 121 opens on the proximal end, various flow paths are defined. For example, as shown in FIG. 5, proximal shaft openings 120 put shaft channel 121 into fluid communication with output flow space 125a and bypass sealed flow space 125b. Thus, as shown in FIG. 5, first chamber 136 discharges before second chamber 132. However, if discharge of second chamber 132 were desired prior to discharge of first chamber 136, a different flow path could be created, for example by causing proximal shaft opening 120 to be in fluid communication with sealed flow space 125b and sealing output flow space 125a (configuration not shown).

According to embodiments having more than one chamber, first chamber 136 and second chamber 132 (collectively chambers 132, 136), are disposed to be in fluid communication with the flow spaces via first chamber conduit 135 and second chamber conduit 133.

Associated with each chamber are compressible members, first compressible member 138 associated with first chamber 136 and second compressible member 134 associated with second chamber 132. According to embodiments, compressible member comprises an elastomeric membrane disposed over each chamber 136, 132. As shown in FIG. 5, first compressible member 138 is an elastomeric membrane that covers first chamber 136; second compressible member 134 is an elastomeric membrane that covers second chamber 132. As flow material enters each chamber 136, 132 through chamber conduits, for example first chamber conduit 135 or second chamber conduit 133, the flow material contacts first compressible member 138 or second compressible member 134, respectively, causing each compressible member 138, 134 to distend into first chamber 136 or second chamber 132, respectively.

Compressible members 138, 134, according to embodiments, may comprise other devices and materials as well. According to some embodiments, the compressible member comprise closed cell foam. According to other embodiments, the compressible member comprises other elastomeric materials. According to still other embodiments, compressible members 138, 134 comprise pockets of air contained within a compressible bag or "pillow," or separated by a mechanical device such as a piston or movable barrier. According to still other embodiments, compressible members 138, 134 comprise pneumatic chambers that are controlled via movement of air or vented outside of flow metering device 100.

According to embodiments as illustrated in FIG. 5, flow metering device 100 comprises two chambers, first chamber 136 and second chamber 132. Each chamber 132, 136 is associated with compressible member 138, 134, respectively. First compressible member 138 is associated with first chamber 136 and second compressible member 134 is associated with second chamber 132. As illustrated in FIG. 5, first chamber 136 has a significantly larger volume than second chamber 132. Having variable size chambers allows for variable aliquot sizes of flow material to be delivered to a target and adds a degree of fine tuning to applications having sensitivity to the volume of flow material delivered, for example in dosing patients with a pharmaceutical.

Figure 6:
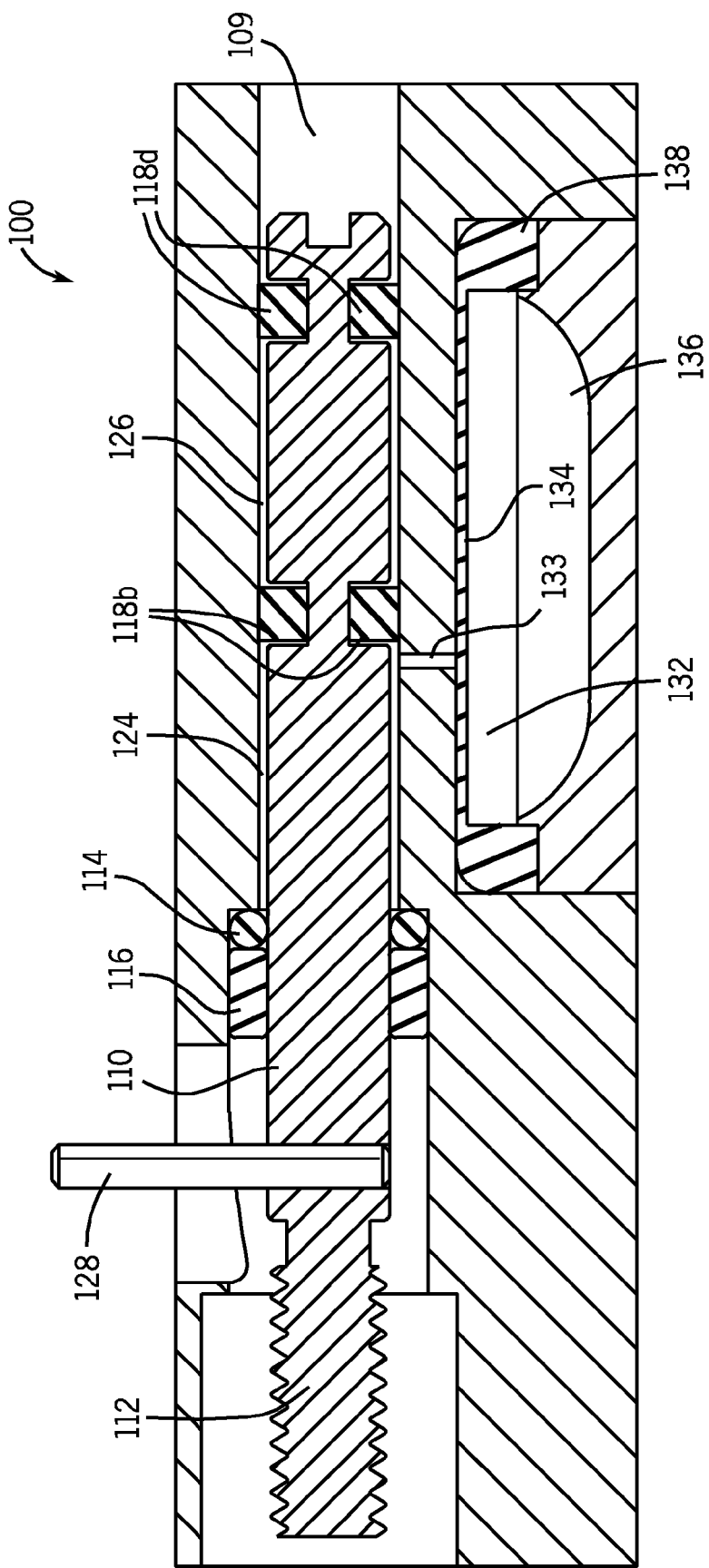
FIG. 6 is a cross-sectional side view of an embodiment of the flow metering device of the present disclosure having one chamber.

According to embodiments, devices of the present disclosure having only a single chamber are contemplated. As illustrated in FIG. 6, single chamber 136 associated with compressible member 138 is shown. Chamber conduit 135 allows chamber 136 to be in fluid communication with proximal flow space 124 and distal flow space 126. Note that according to the embodiment shown in FIG. 6, proximal shaft opening 120, shaft channel 121, and distal shaft opening 122 are omitted. Artisans will readily appreciate that a shaft channel may be used in a one chamber version of the devices of the present disclosure depending on a desired flow channel, for example to transport flow material to a specialize output space.

As shown according to embodiments and as exemplified in FIG. 6, one chamber versions of the devices of the present disclosure need only two movable seals 118b, 118d, which are disposed along actuation shaft 110. Thus, only two flow spaces are defined: proximal flow space 124, defined by fixed seal 114 and movable seal 118b, and distal flow space 126, defined by movable seals 118b and 118d. However, single chamber devices may also be designed with shaft channel 121 in actuation shaft 110, as described above.

According to embodiments, pressure sensors may be disposed within flow metering device 100, for example in the chambers 132, 136 below compressible member to measure pressure and thereby calculate the volume of fluid charging and dispensing from flow metering device 100. Generally, pressure sensors must be disposed in a chamber of known volume with a fixed volume of gas or fluid contacting the pressures sensor. Temperature sensors may be likewise disposed to increase the accuracy of the calculations.

According to other embodiments, no pressure sensors need be disposed in flow metering device 100. Rather, calculation of volume and overall flow rate are calculated at the source. For example, the pumps disclosed in U.S. Pat. Nos. 7,008, 403, 7,341,581, and 7,374,556; U.S. Utility patent application Ser. No. 11/744,819, filed May 4, 2007; and Ser. No. 12/020,498, filed Jan. 25, 2008 (the contents of each above listed patent and patent application are incorporated by reference) may be used as the source of the flow material and the volume dispensed from the source calculated as disclosed therein.

According to embodiments, flow metering device 100 is a disposable device. Indeed, flow metering device 100 may be pre-charged with a flow material in a factory or related setting. In other words, the chambers of flow metering device 100 would be charged with a flow material as a step in the manufacturing process, or in a separate step after manufacturing, but before it is offered to users of the device.

According to embodiments of disposable versions of flow metering device 100, input device 102 is omitted from the device and input conduit 104 sealed after the chambers of flow metering device 100 are charged with the flow material. To use, users insert the disposable into a reusable device configured to receive and actuate flow metering device 100. The reusable device comprises at least an actuation device 112 that can articulate with actuation device 112, and actuates actuation shaft 110 to effect output of the flow material from the chambers of flow metering device 100 as described below.

According to alternate embodiments, flow metering device 100 is a reusable device that is refilled by recharging the chambers. Indeed, according to embodiments, flow metering device 100 is disposed downstream from a pump or other source and is used as a flow material flow rate regulator and safety device. As a flow regulator, it meters the rate at which flow material is delivered to a target because the input and output conduits are never in fluid communication simultaneously. As a safety device, if a pump or flow metering device 100 itself malfunctions, actuation shaft 110 is immediately arrested and the maximum additional flow material that can be delivered is the aliquot of flow material held in the chambers.

Figure 7:
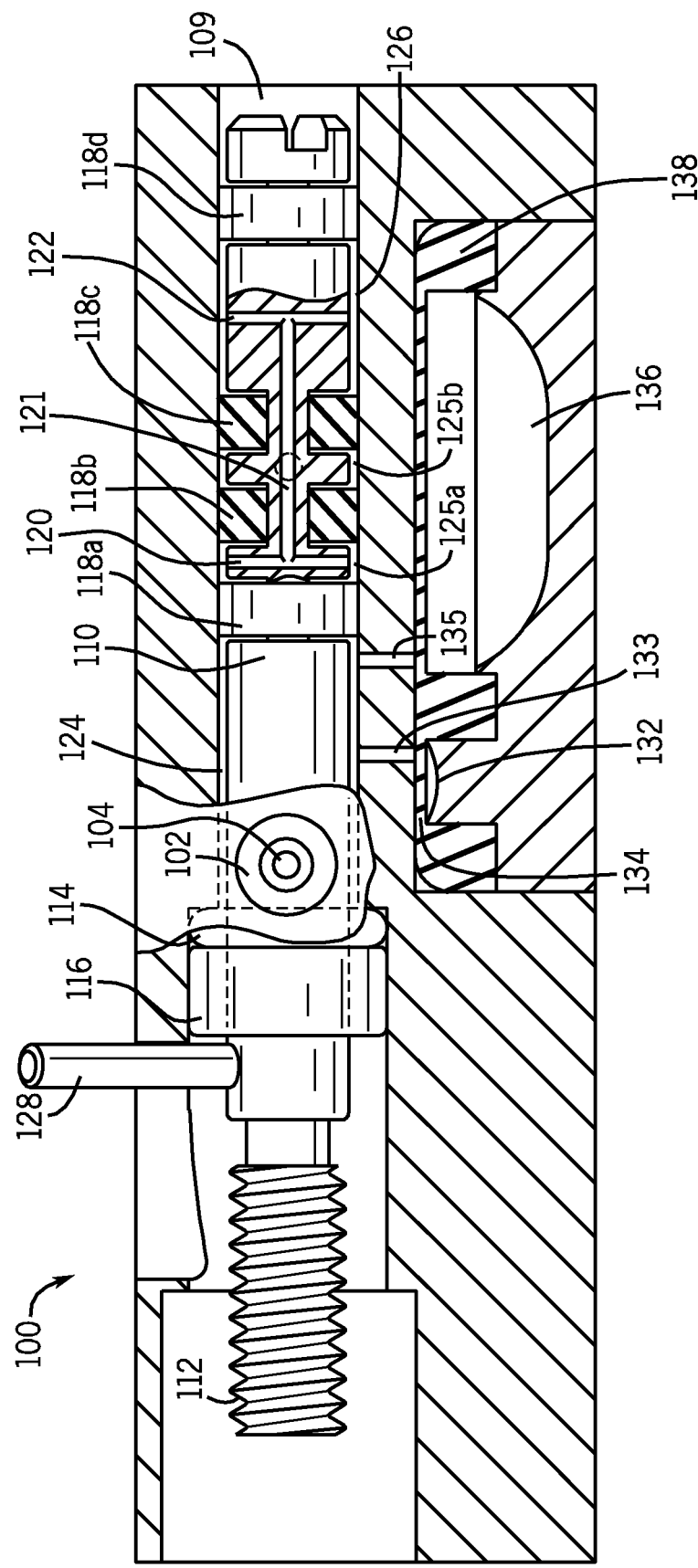
FIG. 7 is a cross-sectional side view of an embodiment of the flow metering device of the present disclosure having two chambers in a charging position.

According to embodiments, the chambers in flow metering device 100 are charged with a flow material when flow metering device 100 has actuation shaft 110 positioned in a charging position, illustrated for a multichamber flow metering device 100 in FIG. 7. According to embodiments, the charging position occurs when the chambers, in this case first chamber 136 and second chamber 132 are put into fluid communication proximal flow space 124 via first chamber conduit 135 and second chamber conduit 133. Artisans will recognize the same principles in one chamber versions, and versions with greater than two chambers without undue experimentation.

FIG. 7 illustrates a two chamber flow metering device 100 where actuation shaft 110 is in a charging position. In the charging position, actuation shaft 110 is moved so that moveable seal 118a is distal to first chamber conduit 135 and second chamber conduit 133. To effect moveable seal 118a being in a position distal of first chamber conduit 135 and second chamber conduit 133, actuation shaft 110 is moved distally, thereby causing movable seals 118a-d to move distally with it. As illustrated in FIG. 7, in this position, actuation shaft connector 112 is in a distal position relative to its outer flow material discharge positions described below.

As actuation shaft 110 moves, actuation guide 128 imparts rotational motion to actuation shaft 110 around the long axis of actuation shaft 110, which also causes moveable seals 118a-d to rotate as well, according to embodiments. Embodiments are expressly contemplated that do not have actuation guide 128 or actuation rotation channel 129, and therefore do not rotate around the long axis of actuation shaft 110. A small degree of rotation reduces friction as actuation shaft 118a-d moves distal and proximal in flow metering device cavity 109.

In the charging position, flow metering device 100 chambers 132, 136 are filled with a flow material that flows in through input conduit 104 of input device 102. When flow metering device 100 is in the charging position, first chamber 136 and second chamber 132 are in fluid communication with input conduit 104 via proximal flow space 124 and first chamber conduit 135 and second chamber conduit 133, respectively, as illustrated in FIG. 7.

Flow material that is flowing into first chamber 136 and second chamber 132 is pressurized, according to embodiments. Thus, as the flow material flows into each of first chamber 136 and second chamber 132, first compressible member 134 and second compressible member 134 are compressed, thereby storing the energy of the pressurized flow material when input conduit 104 is no longer in fluid communication with first chamber 136 and second chamber 132. Flow material may also enter unpressurized and compress compressible members 136, 134 as addition flow material is pumped into each chamber.

As illustrated by the embodiment shown in FIG. 7, compressible members 138, 134 comprise an elastomeric membrane. Indeed, according to the embodiment shown in FIG. 7 and related embodiments, flow material never actually enters the chamber, but rather contacts compressible members 138, 134, which distend into each of first chamber 136 and second chamber 132 respectively. According to embodiments, however, flow material may directly enter the chambers. For example, if compressible members 138, 134 comprise a closed cell foam disposed in each chamber 136, 132 or if each compressible member 138, 134 is a mechanical device, for example a piston.

According to embodiments, charging is completed when the flow material pressure at the source (or at a pumping pressure) and the compressible members 138, 134 come into equilibrium. According to other embodiments, charging is completed prior to an equilibrium state when actuation shaft 110 is moved whereby input conduit 104 is no longer in fluid communication with first chamber 136 or second chamber 132. Artisans will note that it is possible that one chamber is charged to an equilibrium state and the other chamber is charged to a non-equilibrium state due to movement of actuation shaft 110.

Figure 8:
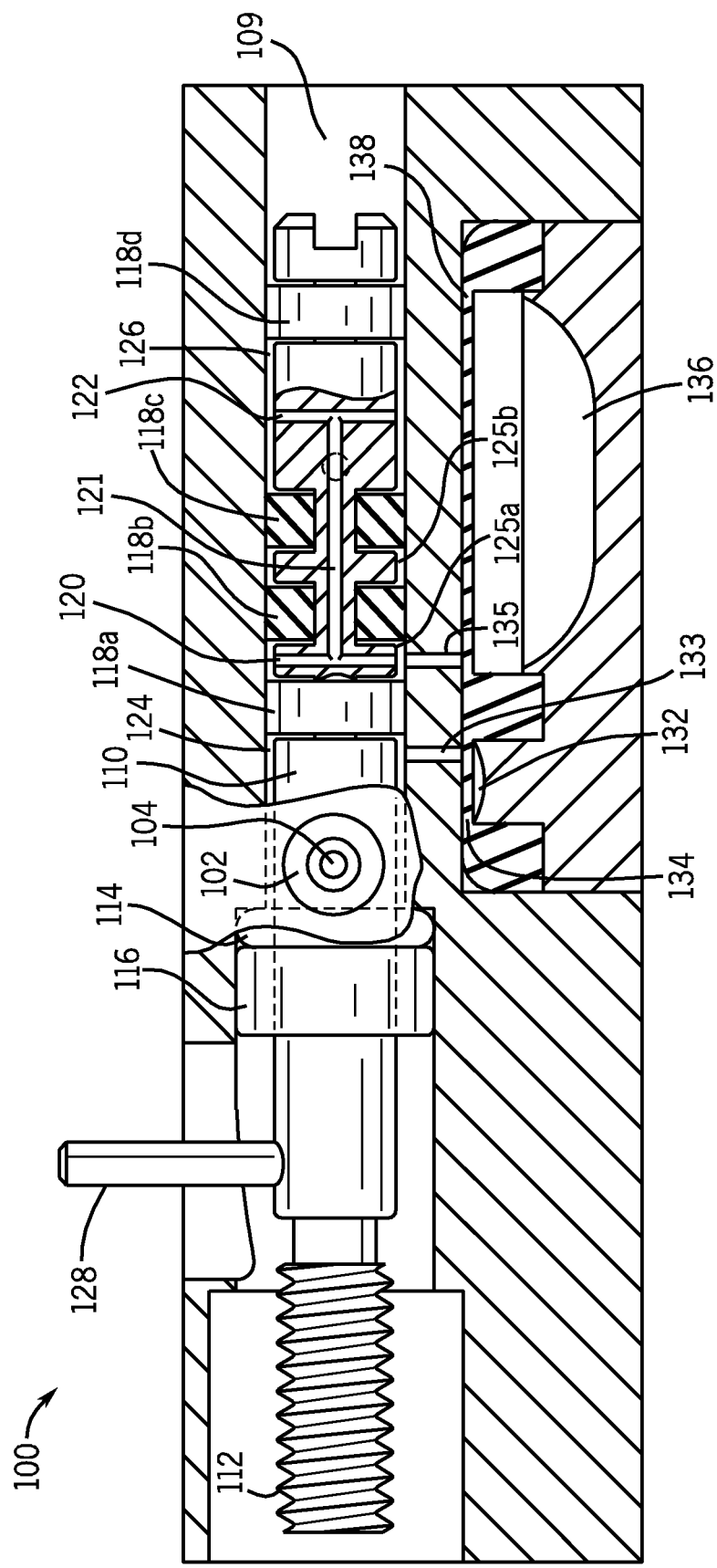
FIG. 8 is a cross-sectional side view of an embodiment of the flow metering device of the present disclosure having two chambers in a first dispense position.

According to embodiments and as illustrated in FIG. 8, after first chamber 136 is charged to the desired volume, actuation shaft 110 is moved proximally to a first dispense position whereby first chamber 136 is no longer in fluid communication with input conduit 104. According to the embodiments shown in FIG. 8, second chamber 132 remains in fluid communication with input conduit 104 via proximal flow space 124 and second chamber conduit 133. Artisans will readily understand that varying the geometry or number of movable seals 118, embodiments can be created whereby no output of flow material from occurs until both first chamber 136 and second chamber 132 are no longer in fluid communication with input conduit 104.

As shown according to the embodiment illustrated in FIG. 8, first chamber 136 is in fluid communication with output flow space 125a. The energy stored in first compressible member 138 causes flow material to flow into output flow space 125a, into shaft channel 121 via proximal shaft opening 120, and from shaft channel 121 through distal shaft opening 122 into distal flow space 126.

Distal flow space 126 comprises the space between actuation shaft 110 and the walls of flow metering device cavity 109 at the distal end of flow metering device 100. Distal flow space 126 is in fluid communication with output conduit 130, from which flow material is delivered to a target. Flow of flow material is effected via the energy stored in compressible member 138 to the target.

According to embodiments, output conduit 130 forms a conduit from connectors well known and understood by artisans for connecting tubes, piping, or other flow facilitation devices. For example, in a medical context, output conduit 130 may comprise, in part, the conduit of a luer connector or hypodermic needle, according to exemplary embodiments.

According to embodiments of one chamber versions of flow metering device 100 (see FIG. 2, for example) and as disclosed above, shaft channel 121, proximal shaft opening 120, distal shaft opening 122 are omitted. Thus, chamber 138 is either in fluid communication with input conduit 104 via proximal flow space 124, in fluid communication with output conduit 130 via distal flow space 126, or not in fluid communication with either proximal flow space 124 or distal flow space 126 when moveable seal covers chamber conduit 135. Embodiments of one chamber versions of flow metering device 100 having shaft channel 121 are, however, contemplated and would operate according to the principles of flow through shaft channel 121 disclosed above.

Figure 9:
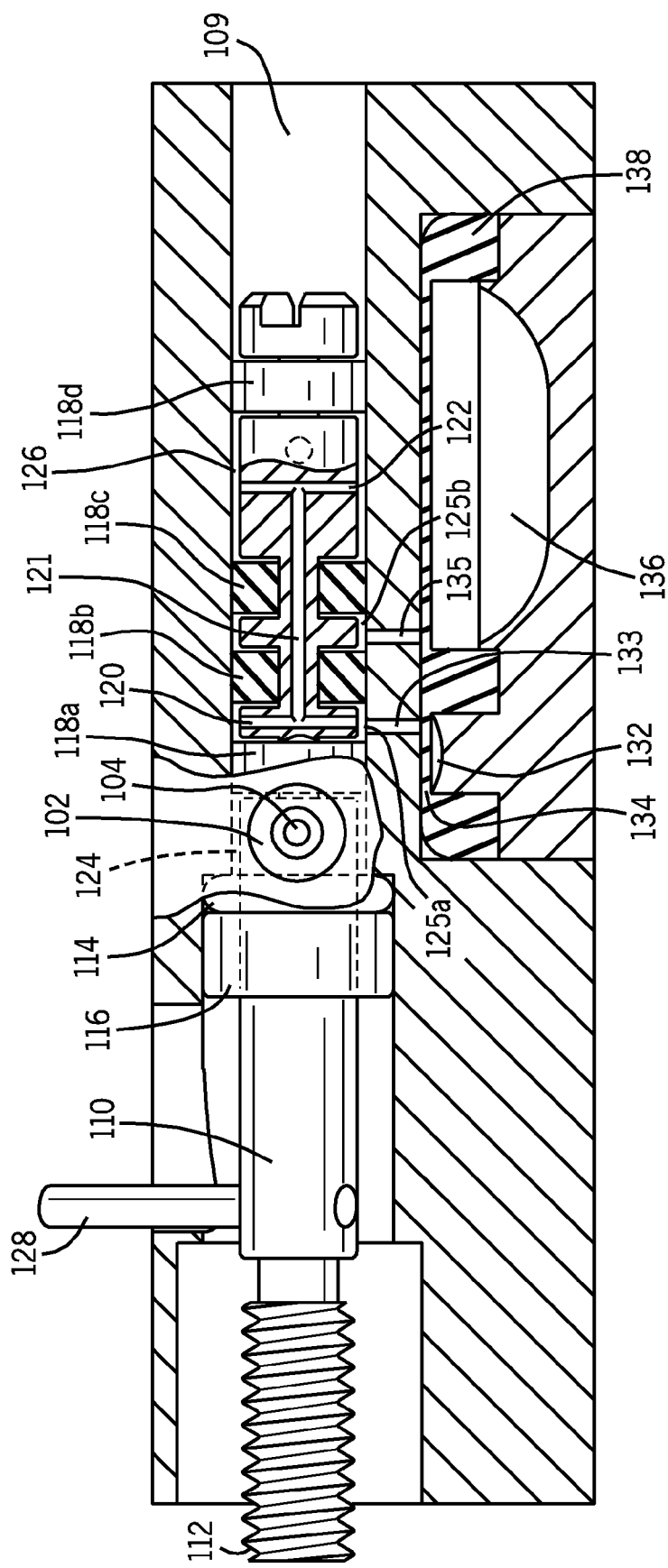
FIG. 9 is a cross-sectional side view of an embodiment of the flow metering device of the present disclosure having two chambers in a second dispense position.

Referring again to a two chamber embodiment of flow metering device 100 illustrated in FIGS. 7-9, and referring specifically to the embodiment illustrated in FIG. 9 in which actuation shaft 110 has been moved fully proximal into a second dispense position. In this position, as illustrated, input conduit 104 is no longer in fluid communication with any chamber 136, 132. As shown, second chamber 132 is in fluid communication with output conduit 130 via output flow space 125a, shaft channel 121, and distal flow space 124. According to the embodiment shown, first chamber 136 is in fluid communication only with sealed flow space 125b. As sealed flow space 125b is not in fluid communication with any other space or conduit, sealed flow space 125b prevents flow of the flow material contained in first chamber 136.

Artisans will readily observe that various permutations may be made to the positioning and placement of moveable seals 118, as well as shaft channel 121, proximal shaft opening 120, and distal shaft opening 122. Indeed, configurations are possible whereby both first chamber 136 and second chamber 132 are in fluid communication with output conduit 130, where second chamber 132 is in fluid communication with output conduit 130 prior to first chamber 136 being in fluid communication with output conduit 130, and many other permutations depending on the configuration of the chambers and the objectives of the design.

Figure 10:
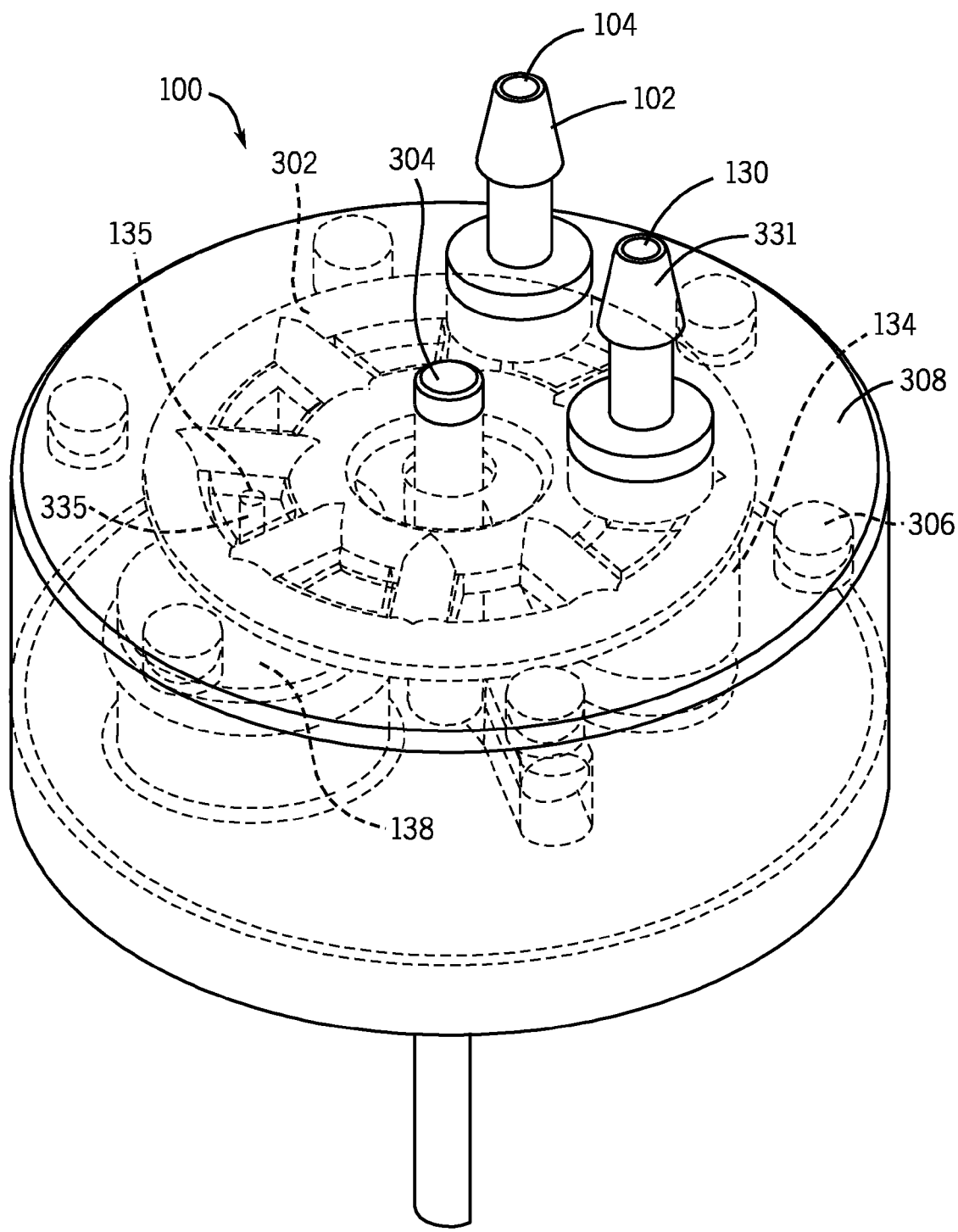
FIG. 10 is a cross-sectional side view of an embodiment of the flow metering device of the present disclosure having two chambers and rotating about an axis.
Figure 11:
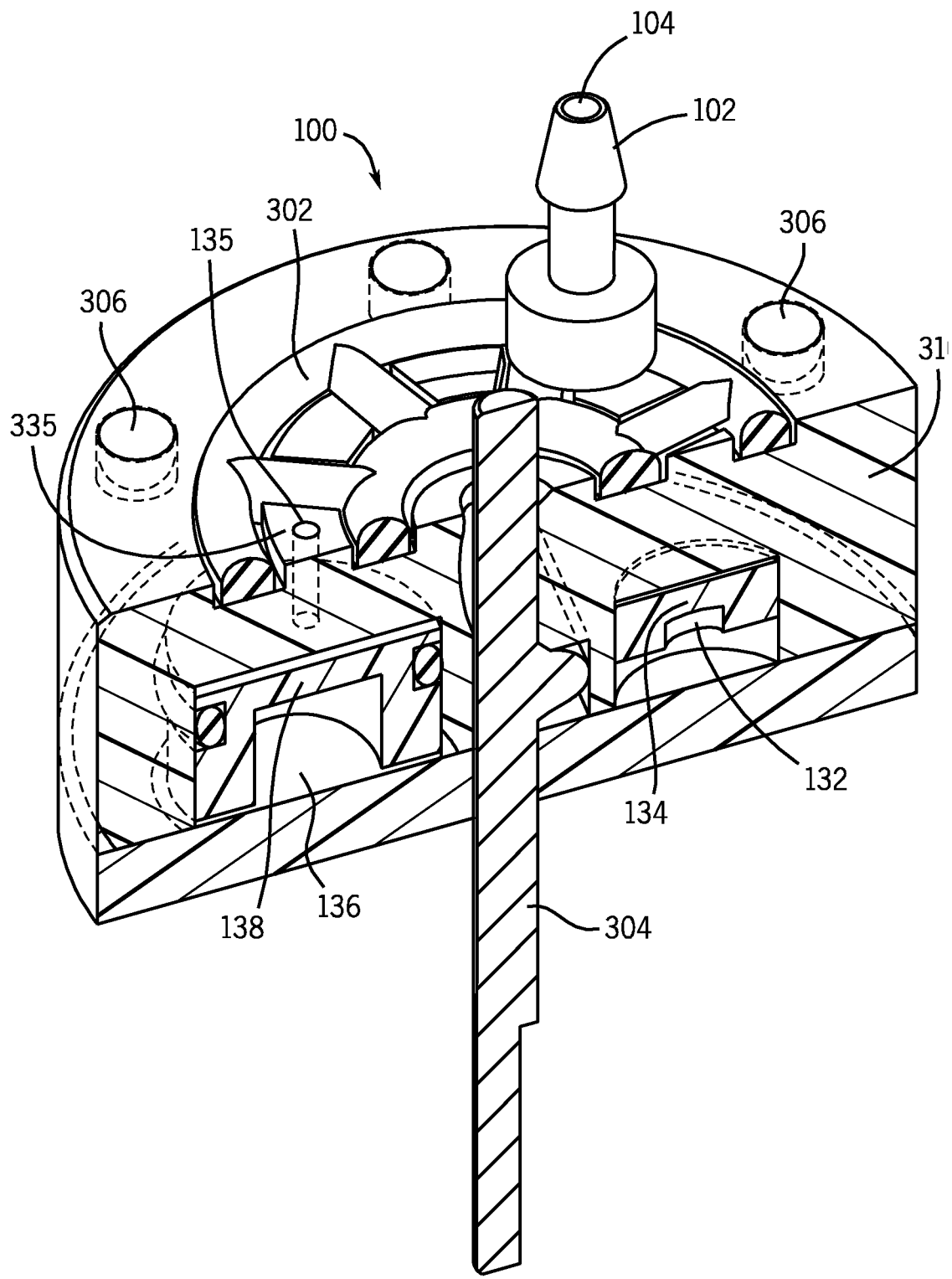
FIG. 11 is a cross-sectional perspective view of an embodiment of the flow metering device of the present disclosure having two chambers and rotating about an axis.

FIGS. 10-12 illustrate embodiments of rotating flow metering device 100. Indeed, the principles used for charging and dispensing flow materials from rotating flow metering device 100 are the same as the principles used to operate the "linear" flow metering devices disclosed and equivalent to those disclosed in the present disclosure.

As illustrated in FIG. 10, there is shown flow metering device 100 that operates by rotating around axis 304. As illustrated, flow metering device 100 comprises two chambers, 136, 132 (see FIG. 11), compressible members 138, 134, and chamber conduits 135, 133. Additionally, input device 102 having input conduit 104 and output device 131 having output conduit 130. Input conduit 104 and output conduit 130 effects communication between each chamber 136, 132 and locations external to flow metering device 100 via chamber conduits 135, 133. Input conduit 104 and output conduit 130, however, are never directly in communication. As will be understood by artisans, flow metering devices may comprises a single chamber, according to embodiments.

Operation of "rotary" versions flow metering device 100 occurs differently than the "linear" version. Nevertheless the principles of operation are the same as will readily be recognized by a person of ordinary skill in the art. As illustrated in FIG. 10, input device 102 and output device 131 are each disposed on upper surface 308 which is disposed above rotation seal 302. Rotation seal 302 is disposed between upper surface 308, upon which input device 102 and output device 131 are mounted, and lower surface 310. Lower surface 310 comprises, according to embodiments, a housing for chambers 136, 132, ball bearings 306, and chamber conduits 135, 133. Ball bearings 306 rest between the upper surface and lower surface as well, and are used to help the upper surface rotate around axis 304, according to embodiments. Artisans will readily recognize that ball bearings are an optional component and may be substituted or left off depending on the specifications of each given embodiment.

According to embodiments, input conduit 104 and output conduit 130 comprise a channel through input device 102 and output device 131, respectively, and also form an opening through upper surface 308. Rotation seal 302, as illustrated in FIG. 11, forms a plurality of transfer chambers (including transfer chamber 333 and transfer chamber 335 as shown if FIG. 12) defined on the sides by rotation seal 302, on the top by upper surface 308, and on the bottom by lower surface 310. According to embodiments, the chambers so defined are suitably small to prevent large volumes of flow material from accumulating within them. Keeping the chambers defined by rotation seal 302 ensures the majority of flow material being metered by flow metering device 100 is delivered rather than retained within the device.

According to embodiments, and as shown in FIG. 10, chamber conduit 135 (and chamber conduit 133, which is not shown), forms a channel through lower surface 310 bringing second chamber 138 into communication with transfer chamber 333. The same is true for first chamber 132, as shown in detail in FIG. 12.

Operation of the rotating flow metering device 100 occurs by rotating input device 102 and input conduit 104 over transfer chamber 333. For example, first chamber 132 is charged with a flow material and the flow material is subsequently delivered from first chamber 132 and delivered to a target via output conduit 130 of output device 131. Flow of flow material is effect via the principles disclosed above through input conduit 104, into transfer chamber 333, through first chamber conduit 133, and into first chamber 132. The same process occurs for second chamber by rotating upper surface 308 so that input conduit is in communication with transfer chamber 335.

After the charging process is complete, upper surface 308 is rotated relative to lower surface 310 and rotation seal 302, which do not rotate with upper surface 308. Eventually, input conduit 104 is rotated whereby it is no longer in communication with transfer chamber 333. According to embodiments, input conduit 104 and output conduit 130 reside on the same line of circumference on upper surface 308, but spaced whereby input conduit 104 and output conduit 130 are never in communication with transfer chamber 333 concurrently.

To dispense flow material from first chamber 332, upper surface 308 is rotated until output conduit is in communication with transfer chamber 333. Once communication is established, delivery of flow material is effected as disclosed herein according to the general principles disclosed for delivery for flow material from first chamber 132 or second chamber 136. Once first chamber 132 is in communication with output conduit 130 via first chamber conduit 133 and transfer chamber 333, flow material flows through the conduits and chambers and is thereby delivered.

According to embodiments of methods of the present disclosure, and as illustrated in FIG. 13, flow metering device 100 of FIGS. 7-9 is operated by actuating actuation shaft 110 proximally and distally. In operation 1002, actuation shaft 110 is positioned in a charging position whereby first chamber 136 and second chamber 132 are charged with a flow material in operation 1004. After charging, actuation shaft 110 is positioned in a first dispense position in operation 1006, whereby first chamber 136 dispenses flow material contained therein into output conduit 130 and in operation 1008 thereafter to a target. Finally, in operation 1010, actuation shaft 110 is positioned in a second dispense position in operation 1010 whereby flow material contained therein is dispensed into output conduit 130 in operation 1012 and thereafter to a target.

Similarly, and as illustrated in FIG. 14, the operation of a one chamber embodiment of flow metering device 100 is illustrated. In operation 1102, actuation shaft 110 is positioned in a charging position whereby chamber 136 is charged with a flow material in operation 1104, provided it is not already filled. Once filled, actuation shaft 110 is positioned in a dispense position 1106 whereby flow material is dispensed into output conduit in operation 1108.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A flow metering device comprising:
a housing including a cavity;
an input conduit in fluid communication with the cavity;
an output conduit in fluid communication with the cavity;
a chamber which is in fluid communication with the cavity and which includes a compressible member comprising an elastomeric membrane configured to store energy; and
an actuation shaft disposed in the cavity, the actuation shaft including at least one moveable seal defining at least one flow space within the cavity and configured such that when the actuation shaft is disposed in a charging position the input conduit is in fluid communication with the chamber through a flow space, when the actuation shaft is disposed in a dispense position the chamber is in fluid communication with the output conduit through a flow space and the input conduit is never in fluid communication with the output conduit, and wherein the elastomeric membrane is disposed over the chamber and is configured to distend into the chamber as flow material enters the chamber.

2. The device of claim 1, wherein the chamber comprises a first chamber and further comprising a second chamber in fluid communication with the cavity.

3. The device of claim 2, wherein the actuation shaft comprises four movable seals which define a proximal flow space, an output flow space, a sealed flow space, and a distal flow space, and the actuation shaft further comprises at least a shaft channel defined at the ends by at least one proximal shaft opening and at least one distal shaft opening.

4. The device of claim 2, wherein the first chamber has a volume which is different from a volume of the second chamber.

5. The device of claim 1, further comprising a pressure sensor disposed in the chamber.

6. The device of claim 1, wherein the volume of a flow material in the device at the time when the device is fully charged with the flow material is determined at a source of the flow material.

7. The device of claim 1 further comprising an actuator coupled to the actuation shaft for effecting movement of the actuation shaft.

8. The device of claim 1 wherein the actuation shaft comprises a plurality of moveable seals defining a proximal flow space and a distal flow space and wherein the flow spaces are configured such that when the actuation shaft is in the charging position the input conduit is in fluid communication with the chamber through the proximal flow space and when the actuation shaft if in the dispense position the chamber is in fluid communication with the output conduit through the distal flow space.

9. A method of flow metering comprising:
positioning an actuation shaft of a flow metering device into a charging position such that a chamber, a proximal flow space formed by at least one moveable seal of the actuation shaft, and an input conduit of the flow metering device are in fluid communication and the chamber and an output conduit are not in fluid communication;
charging the chamber with pressurized flow material through the input conduit such that a compressible member comprising an elastomeric membrane in the chamber compresses and stores energy, wherein the elastomeric membrane is disposed over the chamber such that it distends into the chamber as flow material enters the chamber;
positioning the actuation shaft into a dispense position such that the chamber, a distal flow space and the output conduit are in fluid communication and the chamber and input conduit are not in fluid communication; and
dispensing flow material from the chamber effected by the energy stored in the compressible member;
wherein the proximal flow space and the input conduit are never in fluid communication with the distal flow space and the output conduit.

10. The method of claim 9, further comprising:
measuring a pressure within the chamber at intervals; and
calculating a flow rate of flow material from the chamber in about real time.

11. The method of claim 9 wherein the flow metering device contains more than one chamber and further comprising positioning the actuation shaft in a position whereby at least one chamber is in fluid communication with the distal flow space and the output conduit and at least one other chamber is either sealed or in fluid communication with the input conduit and proximal flow space.

12. A flow metering device comprising:
a housing including a cavity;
an input conduit in fluid communication with the cavity;
an output conduit in fluid communication with the cavity;
a chamber which is in fluid communication with the cavity and which includes a compressible member configured to store energy; and
an actuation shaft disposed in the cavity, the actuation shaft including at least one moveable seal defining at least one flow space within the cavity and configured such that when the actuation shaft is disposed in a charging position the input conduit is in fluid communication with the chamber through a flow space, when the actuation shaft is disposed in a dispense position the chamber is in fluid communication with the output conduit through a flow space and the input conduit is never in fluid communication with the output conduit; and
wherein the chamber comprises a first chamber and further comprising a second chamber in fluid communication with the cavity, and the actuation shaft comprises four movable seals which define a proximal flow space, an output flow space, a sealed flow space, and a distal flow space, and the actuation shaft further comprises at least a shaft channel defined at the ends by at least one proximal shaft opening and at least one distal shaft opening.

13. The device of claim 12, wherein the first chamber has a volume which is different from a volume of the second chamber.

14. The device of claim 12, wherein the compressible member comprises an elastomeric membrane.

15. The device of claim 12, further comprising a pressure sensor disposed in the chamber.

16. The device of claim 12, wherein the volume of a flow material in the device at the time when the device is fully charged with the flow material is determined at a source of the flow material.

17. The device of claim 12, further comprising an actuator coupled to the actuation shaft for effecting movement of the actuation shaft.

18. The device of claim 14, wherein the elastomeric membrane is disposed over the chamber and is configured to distend into the chamber as flow material enters the chamber.

* * * * *